(12) United States Patent
Farmer et al.

(10) Patent No.: US 10,576,519 B2
(45) Date of Patent: Mar. 3, 2020

(54) ENHANCED MICROBIAL PRODUCTION OF BIOSURFACTANTS AND OTHER PRODUCTS, AND USES THEREOF

(71) Applicant: LOCUS OIL IP COMPANY, LLC, Solon, OH (US)

(72) Inventors: Sean Farmer, North Miami Beach, FL (US); Xiaozhou Zhang, Solon, OH (US); Sharmistha Mazumder, Copley, OH (US); Maja Milovanovic, North Royalton, OH (US)

(73) Assignee: LOCUS OIL IP COMPANY, LLC, Solon, OH (US)

( * ) Notice: Subject to any disclaimer, the term of this patent is extended or adjusted under 35 U.S.C. 154(b) by 0 days.

(21) Appl. No.: 15/512,549

(22) PCT Filed: Sep. 12, 2016

(86) PCT No.: PCT/US2016/051327
§ 371 (c)(1),
(2) Date: Mar. 18, 2017

(87) PCT Pub. No.: WO2017/044953
PCT Pub. Date: Mar. 16, 2017

(65) Prior Publication Data
US 2018/0272396 A1    Sep. 27, 2018

Related U.S. Application Data

(60) Provisional application No. 62/216,934, filed on Sep. 10, 2015.

(51) Int. Cl.
*A61K 35/742* (2015.01)
*B09C 1/10* (2006.01)
(Continued)

(52) U.S. Cl.
CPC ............... *B09C 1/10* (2013.01); *A01N 63/00* (2013.01); *A01N 63/02* (2013.01); *C07K 14/32* (2013.01);
(Continued)

(58) Field of Classification Search
None
See application file for complete search history.

(56) References Cited

U.S. PATENT DOCUMENTS

| 4,332,904 A | 6/1982 | Kurane et al. |
| 4,450,908 A | 5/1984 | Hitzman |

(Continued)

FOREIGN PATENT DOCUMENTS

| CN | 102352227 A | 2/2012 |
| CN | 105753283 A | 7/2016 |

(Continued)

OTHER PUBLICATIONS

Nitschke et al. "Production and properties of a surfactant obtained from Bacillus subtilis grown on cassava wastewater". Bioresource Technology 97 (2006) 336-341. (Year: 2006).*

(Continued)

*Primary Examiner* — Blaine Lankford
*Assistant Examiner* — Lauren K Van Buren
(74) *Attorney, Agent, or Firm* — Saliwanchik, Lloyd & Eisenschenk

(57) ABSTRACT

This present invention relates to compositions and methods of microbial enhanced oil recovery using *Bacillus subtilis* strains. The invention also relates to compositions and methods for performing oil degradation with *Bacillus subtilis* strains. The compositions and methods of the present invention are also used for enhanced commercial biosurfactant and enzyme production.

4 Claims, 14 Drawing Sheets

Specification includes a Sequence Listing.

(51) Int. Cl.
| | |
|---|---|
| *A01N 63/02* | (2006.01) |
| *C07K 14/32* | (2006.01) |
| *C12P 1/04* | (2006.01) |
| *C12Q 1/689* | (2018.01) |
| *C12R 1/125* | (2006.01) |
| *C12N 1/20* | (2006.01) |
| *C12N 1/38* | (2006.01) |
| *A01N 63/00* | (2020.01) |
| *C12N 9/00* | (2006.01) |

(52) U.S. Cl.
CPC .................. *C12N 1/20* (2013.01); *C12N 1/38* (2013.01); *C12P 1/04* (2013.01); *C12Q 1/689* (2013.01); *C12R 1/125* (2013.01); *B09C 2101/00* (2013.01); *C12N 9/00* (2013.01); *C12Q 2600/158* (2013.01); *Y02W 10/45* (2015.05)

(56) References Cited

U.S. PATENT DOCUMENTS

| | | | |
|---|---|---|---|
| 4,522,261 | A | 6/1985 | McInerney et al. |
| 4,905,761 | A | 3/1990 | Bryant |
| 6,033,901 | A | 3/2000 | Powell, Jr. |
| 7,556,654 | B1 | 7/2009 | Nero |
| 2005/0266036 | A1 | 12/2005 | Awada et al. |
| 2009/0029879 | A1 | 1/2009 | Soni et al. |
| 2010/0044031 | A1 | 2/2010 | Fallon et al. |
| 2012/0021505 | A1 | 1/2012 | Kim et al. |
| 2012/0122740 | A1 | 5/2012 | Roldan Carrillo et al. |
| 2012/0220464 | A1 | 8/2012 | Giessler-Blank et al. |
| 2012/0292022 | A1 | 11/2012 | Choban et al. |
| 2013/0062053 | A1 | 3/2013 | Kohr et al. |
| 2013/0324406 | A1 | 12/2013 | Chisholm et al. |
| 2014/0273150 | A1 | 9/2014 | Angel |
| 2014/0315765 | A1 | 10/2014 | McDaniel |
| 2014/0323757 | A1 | 10/2014 | Kim |
| 2015/0037302 | A1 | 2/2015 | Bralkowski et al. |
| 2015/0044356 | A1 | 2/2015 | Bootsma et al. |
| 2015/0045290 | A1 | 2/2015 | Coutte et al. |
| 2015/0118203 | A1 | 4/2015 | Boyette et al. |
| 2015/0300139 | A1 | 10/2015 | Armstrong et al. |
| 2015/0305347 | A1 | 10/2015 | Wicks et al. |
| 2016/0040119 | A1 | 2/2016 | Hashman |
| 2016/0083757 | A1 | 3/2016 | Fonseca et al. |
| 2016/0222280 | A1 | 8/2016 | Kohr et al. |

FOREIGN PATENT DOCUMENTS

| | | | |
|---|---|---|---|
| EP | 0540074 | A1 | 5/1993 |
| JP | 5724089 | B2 | 5/2015 |
| WO | 2012010407 | A1 | 1/2012 |
| WO | 2017043058 | A1 | 3/2014 |
| WO | 2014152350 | A1 | 9/2014 |
| WO | 2015089183 | A2 | 6/2015 |

OTHER PUBLICATIONS

Sharma et al. "A Study on biosurfactant production in Lactobacillus and Bacillus" Int. J. Microbio. App. Sci (2014) 3(11) 723-733. (Year: 2014).*
Ghojavand et al. "Isolation of thermotolerant, halotolerant, facultative, biosurfactant-producing bacteria" Appl Microbiol Biotechnol (2008) 80: 1073-1085 (Year: 2008).*
Morikawa et al. "Beneficial Biofilm Formation by Industrial Bacteria *Bacillus subtilis* and Related Species" Journal of Bioscience and Bioengineering, vol. 101, No. 1, 1-8, 2006. (Year: 2006).*
2014 Interim Eligibility Guidance Quick Reference Sheet (USPTO) (Year: 2014).*
Alias, N. et al., "*Saccgaromyces cerevisiae* from Baker's Yeast for Lower Oil Viscosity and Beneficial Metabolite to Improve Oil Recovery: An Overview." Applied Mechanics and Materials, 2014, 625: 522-525.
Amani, H., et al., "Comparative study of biosurfactant producing bacteria in MEOR applications." Journal of Petroleum Science and Engineering, 2010, 75: 209-214.
Brito, D., Biosurfactants from renewable raw materials, Universidade do Minho Departamento de Engenharia Biologica, Nov. 2013, pp. 1-93.
De Almeida, D., et al., "Biosurfactants: Promising Molecules for Petroleum Biotechnology Advances." Frontiers in Microbiology, Oct. 2016, 7(1718): 1-14.
Gudina, E., et al., "Biosurfactant-producing and oil-degrading Bacillus subtilis strains enhance oil recovery in laboratory sand-pack columns." Journal of Hazardous Materials, 2013, 261: 106-113.
Oliveira, M., et al., "Review: Sophorolipids a Promising Biosurfactant and it's Applications." International Journal of Advanced Biotechnology and Research, 2015, 6(2): 161-174.
Silva, R., et al., "Applications of Biosurfactants in the Petroleum Industry and the Remediation of Oil Spills." International Journal of Molecular Sciences, 2014, 15: 12523-12542.
Ghojavand, H. et al., "Isolation of thermotolerant, halotolerant, facultative biosurfactant-producing bacteria." *Appl. Microbiol. Biotechnol*, Oct. 2008, 80(6): Abstract, doi: 10,1007/s00253-008-1570-7.
Sharma, A. et al., "A study on biosurfactant production in *Lactobacillus* and *Bacillus sp.*" Int. J. Curr. Microbiol. App. Sci., 2014, 3(11): 723-733.
E Silva, F.C.P.R. et al., "Yeasts and bacterial biosurfactants as demulsifiers for petroleum derivative in seawater emulsions." AMB Expr., 2017, 7(202): 1-13.
Pacwa-Plociniczak, M. et al., "Review: Environmental Applications of Biosurfactants: Recent Advances." Int. J. Mol. Sci., 2011, 12: 633-654.

\* cited by examiner

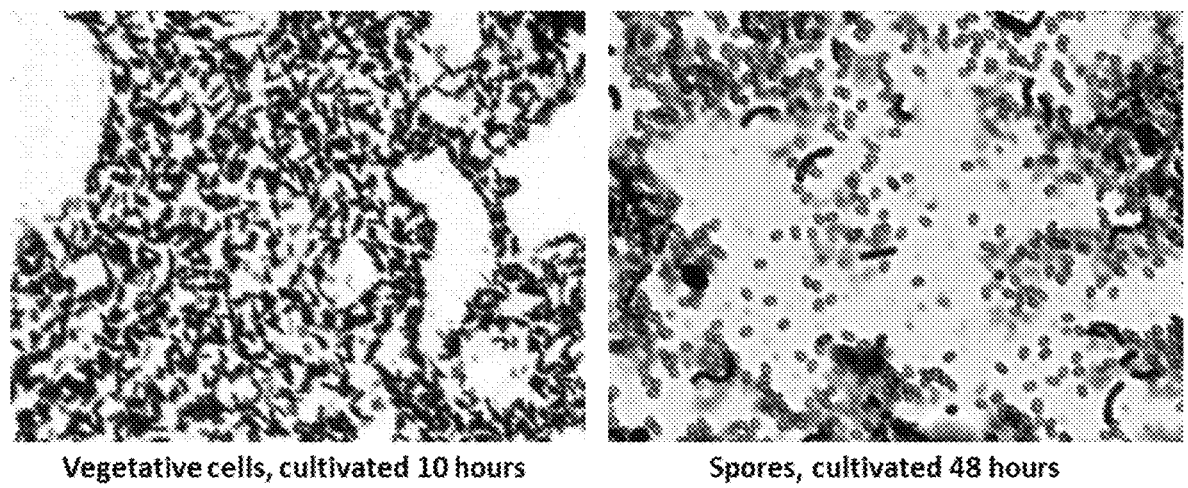
Vegetative cells, cultivated 10 hours
Spores, cultivated 48 hours
FIG. 3A
FIG. 3B
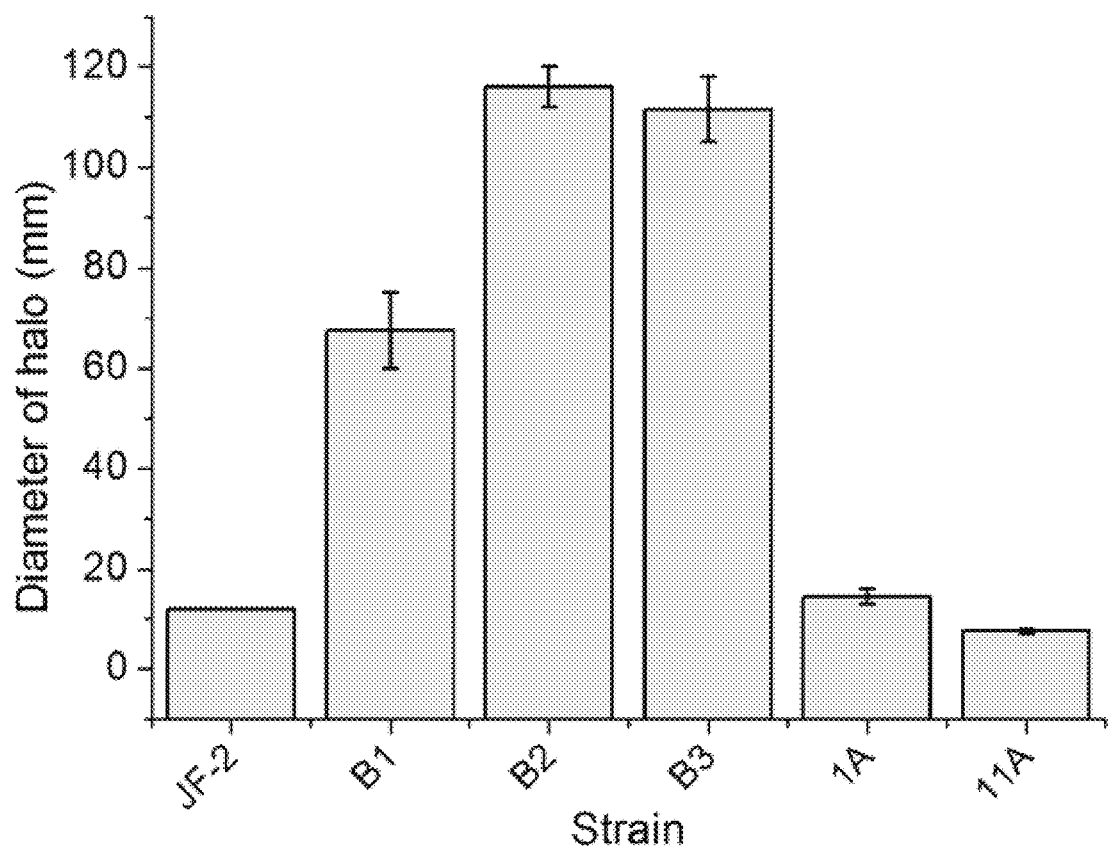
FIG. 4

ENHANCED MICROBIAL PRODUCTION OF BIOSURFACTANTS AND OTHER PRODUCTS, AND USES THEREOF

CROSS-REFERENCE TO A RELATED APPLICATION

This application is a National Stage Application of International Application No. PCT/US2016/051327, filed Sep. 12, 2016; which claims the benefit of U.S. provisional application Ser. No. 62/216,934, filed Sep. 10, 2015, both of which are incorporated herein by reference in its their entirety.

The Sequence Listing for this application is labeled "SeqList-12Sep16-ST25.txt", which was created on Sep. 12, 2016, and is 65 KB. The entire content is incorporated herein by reference in its entirety.

BACKGROUND OF THE INVENTION

Microorganisms, such as bacteria, are important for the production of a wide variety of useful bio-preparations. These microorganisms play crucial roles in, for example, the food industry, pharmaceuticals, agriculture, mining, oil production, environmental clean-up, and waste management.

The high demand for fossil fuels necessitates efficient production of oil. As oil wells mature, it becomes more difficult and costly to continue to pump oil at an economically viable rate. Therefore, there is a need to develop improved methods of oil recovery. One such mechanism utilizes microbes and their by-products.

Oil exists in small pores and narrow fissures within the body of reservoir rocks underneath the surface of the earth. Natural pressure of the reservoir causes the oil to flow up to the surface, thereby providing primary production; however as oil production progresses, the reservoir pressure is depleted to a point at which artificial lift or pumping is required to maintain an economical oil production rate.

When it is necessary to provide external energy for the reservoir to achieve additional oil recovery (secondary recovery), the extra energy can be introduced by injecting gas (gas injection) and/or water (water flooding). After some years of operation in a field, the injected fluids flow preferentially along high permeable layers that cause these fluids to by-pass oil saturated areas in the reservoir. Therefore, an increasing quantity of water (or gas) rises with the oil and, by decreasing the ratio of oil to water, eventually it becomes uneconomic to continue the process and the field must be abandoned. In this situation, a third stage of oil recovery, so-called tertiary production or Enhanced Oil Recovery (EOR) can be considered.

At this tertiary stage, technically advanced methods are employed to either modify the properties of reservoir fluids or the reservoir rock characteristics. In general, the methods can be classified into four main categories as thermal methods, chemical methods, miscible or solvent injection, and microbial methods.

Microbial Enhanced Oil Recovery (MEOR) is a multi-disciplinary field incorporating, among others: geology, chemistry, microbiology, fluid mechanics, petroleum engineering, environmental engineering and chemical engineering. The microbial processes proceeding in MEOR can be classified according to the oil production problem in the field: well bore clean-up removes mud and other debris blocking the channels where oil flows; well stimulation improves the flow of oil from the drainage area into the well bore; and enhanced water floods increase microbial activity by injecting selected microbes and sometimes nutrients.

Thus, MEOR uses microorganisms and/or their metabolites to enhance the recovery of residual oil. In this method, nutrients and suitable bacteria, which preferably grow under the anaerobic reservoir conditions, are injected into the reservoir. Microbial by-products that can include biosurfactants, biopolymers, acids, solvents, gases, and enzymes modify the properties of the oil and the interactions between oil, water, and the porous media, thereby increasing the mobility, and consequently the recovery, of oil.

Microorganisms also play critical roles in agriculture. A plant's nutrition, growth, and proper functioning are dependent on the quantity and distribution of robust populations of natural microflora that in turn, are influenced by soil fertility, tillage, moisture, temperature, aeration, organic matter, and many other factors. Prolonged drought, variable rainfall, and other environmental variations, including the proliferation of nematodes and other pests, and weeds influence those factors and affect soil microflora diversity and plant health.

As synthetic contact pesticide chemistry and soil fumigants face greater scrutiny, and as new nematicide, herbicide, plant growth regulator, insecticide, bactericide, and fungicide and other crop input chemistry pipelines shrink due to increasing regulatory thresholds, sustainable biological pesticides, growth promoting microbes, microbes that increase the nutritional content of soils and help manage water use efficiency are becoming more important alternatives, particularly those that give similar levels of efficacy as the conventional pesticides, fumigants, plant growth regulators, surfactants and fertilizers.

Nematodes are pests known to infect plants and animals. These microscopic worms can be found in almost every type of environment. When residing in soil, nematodes feed on the roots of the plant, causing significant damage to the root structure and improper development of plants. The damage is generally manifested by the growth of galls, root knots, and other abnormalities. Gall formation leads to reduced root size and ineffectiveness of the root system, which in turn seriously affects other parts of the plant. As a result, the weakened plant becomes vulnerable to attacks by other pathogens. Without proper treatment, the plant dies. Nematodes cause millions of dollars of damage each year to turf grasses, ornamental plants, and food crops.

Chemical nematicides have been widely used to combat and control nematodes. These nematicides range from gas and liquid fumigation, such as methyl bromide and chloropicrin, to application of organophosphates and carbamates, such as thionazin and oxamyl. Despite the widespread use of chemical nematicide in controlling nematodes, there exist serious drawbacks of these methods. First, chemical nematicides exhibit low efficacy against nematodes, in particular, against final instar larvae. Second, they are highly toxic and can harm non-target organisms such as humans, domestic animals, beneficial insects, and wildlife. In addition, their residues may remain on the crop and accumulate in the soil, water, or air. Another concern is the development of resistance to pesticides by the targeted organisms.

Due to the disadvantages of chemical pesticides, the demand for safer pesticides and alternate pest control strategies is increasing. In recent years, biological control of nematodes has received considerable attention. This method utilizes biological agents such as live microbes, and bio-products derived from these microbes. These biological pesticides have important advantages over conventional pesticides. For example, they are less harmful compared to the conventional chemical pesticides. They are more efficient and specific. They often biodegrade quickly, leading to less environmental pollution.

Microbes and their by-products are useful in many settings in addition to oil production and agriculture. These other uses include, but are not limited to, in remediation of soils, water and other natural resources; mining; animal feed; waste treatment and disposal; food and beverage preparation and processing; and human health.

Interest in microbial surfactants has been steadily increasing in recent years due to their diversity, environmentally friendly nature, possibility of large-scale production, selectivity, performance under extreme conditions, and potential applications in environmental protection. Microbially produced surfactants, i.e., biosurfactants reduce the interfacial tension between water and oil and, therefore, a lower hydrostatic pressure is required to move the liquid entrapped in the pores to overcome the capillary effect. Secondly, biosurfactants contribute to the formation of micelles providing a physical mechanism to mobilize oil in a moving aqueous phase.

Biosurfactants enhance the emulsification of hydrocarbons, have the potential to solubilize hydrocarbon contaminants and increase their availability for microbial degradation. The use of chemicals for the treatment of a hydrocarbon polluted site may contaminate the environment with their by-products, whereas biological treatment may efficiently destroy pollutants, while being biodegradable themselves. Hence, biosurfactant-producing microorganisms may play an important role in the accelerated bioremediation of hydrocarbon-contaminated sites. These compounds can also be used in enhanced oil recovery as well as for other applications including herbicides and pesticides formulations, detergents, healthcare and cosmetics, pulp and paper, coal, textiles, ceramic processing and food industries, uranium ore-processing, and mechanical dewatering of peat.

BRIEF SUMMARY OF THE INVENTION

The subject invention provides advantageous microbes, as well as by-products of their growth, such as biosurfacants. The subject invention also provides advantageous methods of using these microbes and their by-products.

In certain embodiments, the subject invention provides microbe-based products, as well as their uses in a variety of settings including, for example, improved oil production, bioremediation and mining; waste disposal and treatment; enhancing livestock and other animal health; and promoting plant health and productivity.

In certain embodiments, the subject invention provides materials and methods for improving oil production by treating drilling sites with microorganisms and/or their by-products in order to enhance recovery of oil. In additional embodiments, microorganisms and/or their by-products can be used in remediation processes to degrade oil from spills and/or contamination.

In some embodiments, the present invention provides salt-tolerant, surfactant over-producing *Bacillus subtilis* strains and by-products thereof. These by-products can include, for example, metabolites, polymers, biosurfactants, enzymes, carbon dioxide, organic acids, and solvents. In preferred embodiments, such strains are characterized by enhanced biosurfactant production compared to wild type *Bacillus subtilis* strains. In certain embodiments, the *Bacillus subtilis* strains have increased enzyme production.

In some embodiments, the *Bacillus subtilis* strains are capable of thriving under low oxygen conditions. In some embodiments, the *Bacillus subtilis* strain is grown under anaerobic conditions. For example, in an oil well treatment system, aerobic fermentation is done first to create a high density of cells and a high concentration of biosurfactants. After being injected into the oil well, the strain will grow under aerobic conditions first, then micro-aerobic, and then followed by complete anaerobic conditions. Under anaerobic conditions, nitrate salts can be added as the electron acceptor to support the anaerobic respiration.

In preferred embodiments, the *Bacillus subtilis* strains have mutations in the comK gene and/or the srfA gene.

In one embodiment the subject invention provides a method for improving oil recovery by applying to an oil drilling site one or more *Bacillus subtilis* strains of the subject invention. The method optionally includes adding nutrients and/or other agents to the site.

The method may also comprise applying the *Bacillus subtilis* strain with one or more alkaline compounds. The alkaline compounds can be selected from, for example, sodium hydroxide, sodium carbonate, sodium hydrogen carbonate, sodium silicate, sodium orthosilicate and combinations thereof.

In some embodiments, the method may also comprise applying *Bacillus subtilis* strains with one or more polymer compounds. The polymer compounds can be selected from, for example, hydrogels, acrylic acid, acrylamide, polyacrylamide, hydrolyzed polyacrylamide (HPAM), polysaccharide, xanthan gum, guar gum, and cellulose polymers.

In some embodiments, the method may also comprise applying the *Bacillus subtilis* strain with one or more surfactants. The surfactants may be, for example, anionic, cationic, or zwitterionic.

In one embodiment, the subject invention provides methods of producing a surfactant by cultivating a microbe strain of the subject invention under conditions appropriate for growth and surfactant production; and purifying the surfactant. The subject invention also provides methods of producing enzymes or other proteins by cultivating a microbe strain of the subject invention under conditions appropriate for growth and protein expression; and purifying the enzyme or other protein.

The subject invention further provides microbes and their by-products for use in, for example, settings including, but not limited to, crops, livestock, forestry, turf management, pastures, aquaculture, mining, waste disposal and treatment, environmental remediation, and human health.

In a specific embodiment, the subject invention provides materials and methods for controlling pests. In one embodiment the pests are nematodes. In one embodiment, biosurfactant-producing microorganisms and/or biosurfactants may be added to the soil, plants' growing medium, plants, aquatic medium, or any area to be treated and to prevent pest damage. The microorganisms can grow in situ and produce the biosurfactants onsite to control nematodes and other pests. Consequently, a high concentration of biosurfactant and biosurfactant-producing microorganisms at a treatment site (e.g., soil) can be achieved easily and continuously.

BRIEF DESCRIPTION OF THE DRAWINGS

FIGS. 3A-3B show microscopic photos of vegetative cells and spores of *Bacillus subtilis* B1. Samples were withdrawn at 10 hours (FIG. 3A) and 48 hours (FIG. 3B) of cultivation. The magnification is 1000 fold.

FIG. 4 shows comparison of biosurfactant activity of different bacteria strains. Different bacteria strains were inoculated and cultivated in modified minimal salt M9Y10 medium at 40° C. for 39 hours, aerobically. For comparison purpose, the performance of typical successful *Bacillus* strains used in MEOR for decades (*Bacillus mojavensis* JF-2, *Bacillus subtilis* 1A and *Bacillus subtilis* 11A) were also tested. As shown in the figure, performance of *Bacillus subtilis* B1, B2 and B3 strains are superior and they have 10-12 fold higher biosurfactant activity than these well-known strains.

BRIEF DESCRIPTION OF THE SEQUENCES

Figure 1:
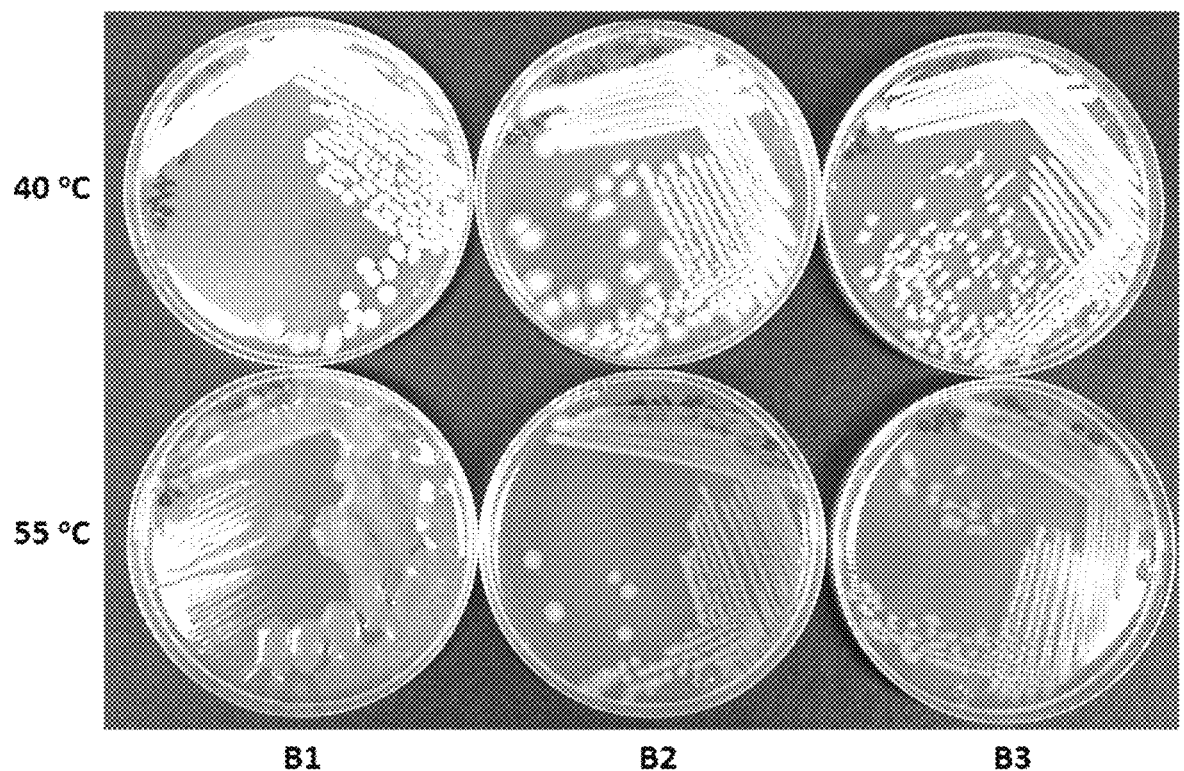
FIG. 1 show colony morphology of *Bacillus subtilis* strains B1, B2 and B3. Strains were streaked on nutrient broth agar plates and cultivated for 15 hours at 40° C. and 55° C. Colony morphology is completely different between the parental strain B1 and its derivate strains B2 and B3. B1 produces biopolymer at both 40° C. and 55° C. B1 produces more biopolymer at 55° C. than at 40° C. B2 and B3 lose the ability to produce biopolymer.

SEQ ID NOs:1-25 is a primer useful according to the subject invention.

SEQ ID NO: 26 is the rrnA-16S sequence.
SEQ ID NO: 27 is the SpoOA sequence.
SEQ ID NO: 28 is the gyrB sequence.
SEQ ID NO: 29 is the comK sequence
SEQ ID NOs: 30-42 is a sequence of an amplicon useful according to the subject invention.
SEQ ID NO: 43 is the srfA operon.
SEQ ID NO:44 is a primer useful according to the subject invention.

DETAILED DESCRIPTION

The subject invention provides advantageous microbes, as well as by-products of their growth, such as biosurfacants. The subject invention also provides advantageous methods of using these microbes and their by-products.

In certain embodiments, the subject invention provides microbe-based products, as well as their uses in a variety of settings including, for example, improved oil production, bioremediation and mining; waste disposal and treatment; enhancing livestock and other animal health; and promoting plant health and productivity.

In specific embodiments, the methods and compositions described herein utilize microorganisms to enhance recovery of oil. The microorganisms improve the quality of oil recovered from mature oil reservoirs. The microorganisms can also be used to degrade oil from spills and/or contamination. Furthermore, the microorganisms remove toxic substances from oil sites.

In one embodiment the subject invention provides a method for performing oil recovery that comprises applying to an oil drilling extraction site a composition of *Bacillus subtilis* strains capable of producing more biosurfactant than other *Bacillus* species, while thriving in a high salt environment that is often encountered at an oil extraction or recovery site.

In some embodiments, the present invention provides salt-tolerant, surfactant over-producing *Bacillus subtilis* strains and by-products thereof. These by-products can include, for example, metabolites, polymers, biosurfactants, enzymes, carbon dioxide, organic acids, and solvents. In preferred embodiments, such strains are characterized by enhanced biosurfactant production compared to wild type *Bacillus subtilis* strains. In certain embodiments, the *Bacillus subtilis* strains also have increased enzyme production.

In preferred embodiments, the *Bacillus subtilis* strains of the subject invention have mutations in the comK gene and/or the srfA gene.

In some embodiments, the *Bacillus subtilis* strains are capable of thriving under low oxygen conditions. In some embodiments, the *Bacillus subtilis* strain is grown under anaerobic conditions. For example in an oil well treatment system, aerobic fermentation is done first to create a high density of cells and a high concentration of biosurfactants. After injection into the oil well, the strain first grows under aerobic conditions, then micro-aerobic, and then followed by complete anaerobic conditions. Under anaerobic conditions, nitrate salts can be added as the electron acceptor to support the anaerobic respiration.

In one embodiment the subject invention provides a method for improving oil recovery by applying to an oil drilling site one or more *Bacillus subtilis* strains of the subject invention. The method optionally includes adding nutrients and/or other agents to the site.

The method may also comprise applying the *Bacillus subtilis* strain with one or more alkaline compounds. The alkaline compounds can be selected from, for example, sodium hydroxide, sodium carbonate, sodium hydrogen carbonate, sodium silicate, sodium orthosilicate and combinations thereof.

In some embodiments, the method may also comprise applying *Bacillus subtilis* strains with one or more polymer compounds. The polymer compounds can be selected from, for example, hydrogels, acrylic acid, acrylamide, polyacrylamide, hydrolyzed polyacrylamide (HPAM), polysaccharide, xanthan gum, guar gum, and cellulose polymers.

In some embodiments, the method may also comprise applying the *Bacillus subtilis* strain with one or more surfactants. The surfactants may be, for example, anionic, cationic, or zwitterionic.

Salt tolerance can be with respect to any one or more of a variety of salts. For example, the salt can be a monovalent salt such as a sodium or potassium salt, e.g., NaCl or KCl, or a divalent salt such as a magnesium or calcium salt, e.g., $MgCl_2$ or $CaCl_2$, or a trivalent salt. Given geographic sites to be treated, zinc, bromium, iron, or lithium salts are present in the composition or site. In preferred embodiments, the bacteria described herein are tolerant to NaCl as well as others of the aforementioned salts and are, therefore, widely useful for oil recovery. For example in Texas, zinc and/or bromium salts are also present; in Colorado, lithium salts are also present; and in Ohio and Pennsylvania, iron salts, e.g., Ferric hydroxide ($Fe(OH)_3$), Ferrous hydroxide ($Fe(OH)_2$), Iron sulfide forms: pyrite ($FeS_2$), troilite (FeS), pyrrhotite (Fe7S8), mackinawite (Fe9S8), and marcasite ($FeS2$), Iron (II) carbonate: $FeCO_3$; Iron (III) oxide: $Fe2O_3$ are present.

The bacteria of the subject invention are "surfactant over-producing." For example, the strain may produce at least 0.1-10 g/L, e.g., 0.5-1 g/L surfactant. For example, the bacteria produce at least 10%, 25%, 50%, 100%, 2-fold, 5-fold, 7.5 fold, 10-fold, 12-fold, 15-fold or more compared to other *B. subtilis* bacteria or other oil-recovery microbial strains. Specifically, ATCC 39307 is used herein as a reference strain.

In certain embodiments, the *Bacillus subtilis* strains comprise one or more mutations in comK gene and/or srfA gene.

The composition includes a *Bacillus subtilis* capable of producing more biosurfactant than other *Bacillus* species while thriving under high salt conditions. For example, a salt-tolerant *Bacillus subtilis* strain proliferates under conditions of 1-15% or higher salt concentration, e.g., at least 5%, 10%, 12%, 15% or more. For example, the strains proliferate and produce oil-recovering metabolites in that range, e.g., 12% or greater salt solutions, e.g., under salt conditions under which *Bacillus mojavensis* JF-2 (ATCC 39307), *Bacillus subtilis* NIPER 1A and *Bacillus subtilis* NIPER 11A do not proliferate and/or perform substantive oil recovery functions.

In one embodiment, the composition according to the subject invention is obtained through cultivation processes ranging from small to large scales. These cultivation processes include, but are not limited to, submerged cultivation/fermentation, surface cultivation, solid state fermentation (SSF), and combinations thereof.

In one embodiment, the subject invention provides methods of producing a surfactant by cultivating a microbe strain of the subject invention under conditions appropriate for growth and surfactant production; and purifying the surfactant. The subject invention also provides methods of producing enzymes or other proteins by cultivating a microbe strain of the subject invention under conditions appropriate for growth and protein expression; and purifying the enzyme or other protein.

The subject invention further provides microbes and their by-products for use in, for example, settings including, but not limited to, crops, livestock, forestry, turf management, pastures, aquaculture, mining, waste disposal and treatment, environmental remediation, and human health.

In a specific embodiment, the subject invention provides materials and methods for controlling pests. In one embodiment the pests are nematodes. In one embodiment, biosurfactant-producing microorganisms and/or biosurfactants may be added to the soil, plants' growing medium, plants, aquatic medium, or any area to be treated and to prevent pest damage. The microorganisms can grow in situ and produce the biosurfactants onsite to control nematodes and other pests. Consequently, a high concentration of biosurfactant and biosurfactant-producing microorganisms at a treatment site (e.g., soil) can be achieved easily and continuously.

Definitions

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The cells may be in a vegetative state or in spore form, or a mixture of both. The cells may be planktonic or in a biofilm form, or a mixture of both. The by-products of growth may be, for example, metabolites, cell membrane components, expressed proteins, and/or other cellular components. The cells may be intact or lysed. In preferred embodiments, the cells are in the vegetative state and are present, with broth in which they were grown, in the microbe-based composition. The cells may be present at, for example, a concentration of $1 \times 10^4$, $1 \times 10^5$, $1 \times 10^6$, $1 \times 10^7$, $1 \times 10^8$, $1 \times 10^9$, $1 \times 10^{10}$, or $1 \times 10^{11}$ or more cells per milliliter of the composition The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, buffers, appropriate carriers, such as water, added nutrients to support further microbial growth, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, an "isolated" or "purified" nucleic acid molecule, polynucleotide, polypeptide, protein or organic compound such as a small molecule (e.g., those described below), is substantially free of other compounds, such as cellular material, with which it is associated in nature. As used herein, reference to "isolated" means that the strain is removed from the environment in which it exists in nature. Thus, the isolated strain may exist as, for example, a biologically pure culture, or as spores (or other forms of the strain) in association with an agricultural carrier.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "*Bacillus subtilis* B series strain" is meant a strain or strains of *Bacillus subtilis* with higher salt tolerance and enhanced biosurfactant production compared to wild type *Bacillus subtilis* strains. *Bacillus subtilis* B series strains are able to grow in anaerobic conditions as well. *Bacillus subtilis* B series strains of the present invention include B1, B2 and B3 strains. The B series strains of *Bacillus subtilis* described herein are characterized by a hight salt tolerance and/or enhanced surfactant production compared to other strains of bacteria used in oil recovery such as *Bacillus mojavensis* JF-2 (ATCC 39307), *Bacillus subtilis* NIPER 1A and *Bacillus subtilis* NIPER 11A.

The term "host cell" refers to a cell that is to be transformed using the methods and compositions of the invention. In general, host cell as used herein means a microorganism cell into which a nucleic acid of interest is to be transformed.

The term "transformation" refers to a permanent or transient genetic change, preferably a permanent genetic change, induced in a cell following incorporation of non-host nucleic acid sequences. Transformation (or transduction, or transfection), can be achieved by any one of a number of means including electroporation, conjugation, microinjection, biolistics (or particle bombardment-mediated delivery), or *agrobacterium* mediated transformation.

The term "vector" generally refers to a polynucleotide that can be propagated and/or transferred between organisms, cells, or cellular components. Vectors include viruses, bacteriophage, pro-viruses, plasmids, phagemids, transposons, and artificial chromosomes, that are able to replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium*.

The term "promoter" refers to a minimal nucleic acid sequence sufficient to direct transcription of a nucleic acid sequence to which it is operably linked. The term "promoter" is also meant to encompass those promoter elements sufficient for promoter-dependent gene expression controllable for cell-type specific expression or inducible by external signals or agents; such elements may be located in the 5' or 3' regions of the naturally-occurring gene.

An engineered or modified microorganism can also include in the alternative or in addition to the introduction of a genetic material into a host or parental microorganism, the disruption, deletion, or knocking out of a gene or polynucleotide to alter the cellular physiology and biochemistry of the microorganism. Through the reduction, disruption or knocking out of a gene or polynucleotide the microorganism acquires new or improved properties (e.g., the ability to produce a new or greater quantities of an intracellular metabolite, improve the flux of a metabolite down a desired pathway, and/or reduce the production of undesirable by-products).

Microorganisms provided herein are modified to produce metabolites in quantities not available in the parental organism. A "metabolite" refers to any substance produced by metabolism or a substance necessary for taking part in a particular metabolic process. A metabolite can be an organic compound that is a starting material (e.g., glucose), an intermediate (e.g., acetyl-CoA) in, or an end product (e.g., n-butanol) of metabolism.

By "biosurfactant" is meant a surface-active substance produced by a living cell. As used herein, Bacillus subtilis strains of the present invention have enhanced biosurfactant producing capabilities over wild type Bacillus subtilis strains.

"Detect" refers to identifying the presence, absence or amount of the analyte to be detected.

By "fragment" is meant a portion of a polypeptide or nucleic acid molecule. This portion contains, preferably, at least 10%, 20%, 30%, 40%, 50%, 60%, 70%, 80%, 90%, 95%, or 99% of the entire length of the reference nucleic acid molecule or polypeptide. A fragment may contain 10, 20, 30, 40, 50, 60, 70, 80, 90, 100, 200, 300, 400, 500, 600, 700, 800, 900, or 1000 nucleotides or amino acids, or more.

By "gene" is meant a locus (or region) of DNA that encodes a functional RNA or protein product.

By "modulate" is meant alter (increase or decrease). Such alterations are detected by standard art known methods such as those described herein.

Nucleic acids include but are not limited to: deoxyribonucleic acid (DNA), ribonucleic acid (RNA), double-stranded DNA (dsDNA), single-stranded DNA (ssDNA), messenger RNA (mRNA), ribosomal RNA (rRNA), transfer RNA (tRNA), micro RNA (miRNA), and small interfering RNA (siRNA).

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 1%, 5%, 10%, 25%, 50%, 75%, or 100%.

By "reference" is meant a standard or control condition.

A "reference sequence" is a defined sequence used as a basis for sequence comparison or a gene expression comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 40 nucleotides, preferably at least about 60 nucleotides, more preferably at least about 75 nucleotides, and even more preferably about 100 nucleotides or about 300 or about 500 nucleotides or any integer thereabout or there between.

As used herein, "obtaining" as in "obtaining an agent" includes synthesizing, purchasing, or otherwise acquiring the agent.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% or more identical at the amino acid level or nucleic acid level to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "salt-tolerant" is meant Bacillus subtilis strains capable of growing in a sodium chloride concentration of fifteen (15) percent or greater. In a specific embodiment, "salt-tolerant" refers to the ability to grow in 150 g/L or more of NaCl.

By "surfactant" is meant compounds that lower the surface tension (or interfacial tension) between two liquids or between a liquid and a solid. Surfactants act as detergents, wetting agents, emulsifiers, foaming agents, and dispersants.

B Series Strains of the Subject Invention

The Bacillus subtilis microorganisms exemplified herein have been characterized and classified as Bacillus subtilis. The vegetative cells of Bacillus subtilis strain B1 are rods that are 0.7 to 0.9 μm wide by 1.6 to 3.3 μm long and occur singly. It is motile, Gram positive and produces biopolymer on nutrient agar and potato dextrose agar. Produces ellipsoidal spores centrally or paracentrally in unswollen sporangia. Size of mature spores are 0.8 to 1.0 μm wide by 1.6 to 1.9 μm long. Agar colonies are cream/beige in color, raised, mucous, circular, entire, smooth, shiny and 3.0 to 7.0 mm in diameter after 16 hours at 40° C. on nutrient agar plate. It is facultative aerobic with a growth temperature range of 25-55° C. with optimal growth temperature at 35° C. It hydrolyze starch, is positive on Voges-Proskauer test, can utilize citrate and grow with 15% NaCl.

A culture of the *B. subtilis* B1 microbe has been deposited with the American Type Culture Collection (ATCC), 10801 University Blvd., Manassas, Va. 20110-2209 USA. The deposit has been assigned accession number ATCC No. PTA-123459 by the depository and was deposited on Aug. 30, 2016.

The subject culture has been deposited under conditions that assure that access to the culture will be available during the pendency of this patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

Strains B2 and B3 are mutants from strain B1, which was confirmed by whole genome sequencing and de novo assembly. Both strain B2 and B3 have 14 mutations on their genomes compared with the genome sequence of B1. There are approximately 1-2 mutations or alterations between B2 and B3. Both strain B2 and B3 lose the ability to produce biopolymer and compared with the parental strain B1. They all have two different point mutations for their glycogen branching protein.

The B strain series of *Bacillus subtilis* produce more biosurfactant compared to reference strains of *Bacillus subtilis*. Furthermore, the *Bacillus subtilis* strains survive under high salt and anaerobic conditions better than other well-known *Bacillus* strains.

The present invention further provides for *Bacillus subtilis* strains with polymer producing capabilities. The polymer producing ability of the microbe can be controlled by the altering the nutrient composition of the medium.

The present invention provides *Bacillus subtilis* strains with enhanced biosurfactant production compared to wild type *Bacillus subtilis* as well as compared to other microbes used in oil recovery. Such *Bacillus subtilis* have been termed members of the B series, including, but not limited to, B1, B2 and B3.

These *Bacillus subtilis* strains are capable of growing in high salt environments. The strains are also capable of growing under anaerobic conditions. The *Bacillus subtilis* B series strains can also be used for producing enzymes that degrade or metabolize oil or other petroleum products.

The microbes can be grown in planktonic form or as biofilm. In the case of biofilm, the vessel may have within it a substrate upon which the microbes can be grown in a biofilm state. The microbes may be induced into a biofilm state using techniques known in the art. The system may also have, for example, the capacity to apply stimuli (such as shear stress) that encourages and/or improves the biofilm growth characteristics.

In specific embodiments, the subject invention provides bacterial strain ATCC and mutants thereof. Procedures for making mutants are well known in the microbiological art. For example, ultraviolet light and nitrosoguanidine are used extensively toward this end.

B series strains in addition to the exemplified B1, B2, and B3 strains can be readily identified using the teachings provided herein. In addition to the advantageous high salt tolerance and surfactant over-production, the strains typically can grow under anaerobic conditions. B series strains can also be identified using PCR primer pairs as set forth herein.

Genetic Analysis of the B Series Strains

The DNA sequences of 16S rDNA and spo0A genes of the B series strains are 100% identical to *Bacillus subtilis* strain ATCC 23857; however, the B series strains do possess a number of genomic variations compared to other *Bacillus subtilis* strains. There are 15 large contigs assembled with good coverage scores. After a preliminary database BLAST, the results showed the many novel sequences in the genome of the B strains, especially in a ~140 kb region on contig2, compared to wild type *Bacillus subtilis* strains.

In particular, the combination of mutations in the comK gene (encoding competence transcription factor) and srfA operon (encoding surfactin synthetase) were unique among the B series strains (B1, B2, B3) compared to other *Bacillus subtilis* strains.

Based on genome background, the B strains have high complementarity with the following two strains: 1) *Bacillus subtilis* strain TO-A JPC and 2) *Bacillus subtilis* KCTC 1028.

The *Bacillus subtilis* strains described herein have superior oil recover capabilities compared to JF-2.

Table 1 below shows conserved genes used for classification. Notes for genes: rrnA-16S, gene encoding ribosomal RNA-16S; spo0A, gene encoding two-component response regulator which is responsible for stage 0 sporulation; comK, gene encoding competence transcription factor; srfA operon: genes encoding surfactin synthetase complex.

TABLE 1

Identities of conserved genes for B strains' classification and functions

| | *B. Subtilis* 168 | B Series Strains | | |
|---|---|---|---|---|
| Genes | Size (bp) | B1 | B2 | B3 |
| rrnA-16S | 1,553 | 100% | 100% | 100% |
| spo0A | 801 | 100% | 100% | 100% |
| comK | 579 | 575/579, 99%, no gap | | |
| srfAoperon | 31,860 | 31704/31845, 99%, 4 gaps | | |

Reference genome: *Bacillus subtilis* 168 (taxid: 224308)

The list of conserved genes used to classify the strains as *B. subtilis* and their sequences are shown below.

List of conserved genes for classification of *B. subtilis* B1, B2 and B3. All the genes listed in Table 2 are identical in all three strains.

TABLE 2

| Gene Name | Sequence | Size (bp) |
|---|---|---|
| rrnA-16S | tttatcggagagtttgatcctggctcaggacgaacgctggcggcgtgcctaatacatgcaagtcg agcggacagatgggagcttgctccctgatgttagcggcggacgggtgagtaacacgtgggtaa cctgcctgtaagactgggataactccgggaaaccggggctaataccggatggttgtttgaaccg catggttcaaacataaaaggtggcttcggctaccacttacagatggacccgcggcgcattagcta gttggtgaggtaacggctcaccaaggcgacgatgcgtagccgacctgagagggtgatcggcc acactgggactgagacacggcccagactcctacgggaggcagcagtagggaatattccgcaat ggacgaaagtctgacggagcaacgccgcgtgagtgatgaaggttttcggatcgtaaagactgtt gttagggaagaacaagtaccgttcgaataagggcggtaccttgacggtacctaaccagaaagcca cggctaactacgtgccagcagccgcggtaatacgtaggtggcaagcgttgtccggaattattgg gcgtaaagggctcgcaggcggtttcttaagtctgatgtgaaagcccccggctcaaccggggag ggtcattggaaactgggaacttgagtgcagaagaggagagtggaattccacgtgtagcggtg aaatgcgtagagatgtggaggaacaccagtggcgaaggcgactctctggtctgtaactgacgct gaggagcgaaagcgtggggagcgaacaggattagataccctggtagtccacgccgtaaacga tgagtgctaagtgttagggggtttccgccccttagtgctgcagctaacgcattaagcactccgcct ggggagtacggtcgcaagactgaaactcaaaggaattgacggggcccgcacaagcggtgg agcatgtggtttaattcgaagcaacgcgaagaaccttaccaggtcttgacatcctctgacaatcct agagataggacgtccccttcggggcagagtgacaggtggtgcatggttgtcgtcagctcgtgt cgtgagatgttgggttaagtcccgcaacgagcgcaaccccttgatcttagttgccagcattcagttg ggcactctaaggtgactgccggtgacaaaccggaggaaggtggggatgacgtcaaatcatcat gccccttatgacctgggctacacacgtgctacaatggacagaacaaagggcagcgaaaccgcg aggttaagccaatcccacaaatctgttctcagttcggatcgcagtctgcaactcgactgcgtgaag ctggaatcgctagtaatcgcggatcagcatgccgcggtgaatacgttcccgggccttgtacacac cgcccgtcacaccacgagagtttgtaacacccgaagtcggtgaggtaaccttttaggagccagc cgccaaggtgggacagatgattggggtgaagtcgtaacaaggtagccgtatcggaaggtgcg gctggatcacctcctttct (SEQ ID NO: 26) | 1553 |
| spo0A | Gtggagaaaattaaagtttgtgttgctgatgataatcgagagctggtaagcctgttaagtgaatata tagaaggacaggaagacatggaagtgatcggcgttgcttataacggacaggaatgcctgtcgct gtttaaagaaaaagatcccgatgtgctcgtattagatattattatgccgcatctagacggacttgcg gttttagagaggctgagggaatcagatctgaaaaaacagccgaatgtcattatgctgacagccttt gggcaggaagatgtcacgaaaaaggccgtcgatttaggcgcgtcctactttattctcaaaccgttt gatatgtgaaaaccttgtcggccatatccgccaggtcagcggaaatgccagcagtgtgacgcatc gtgcgccatcatcgcaaagcagtattatacgcagcagccagcctgaaccaaagaagaaaaatct cgacgcgagcatcacaagcattatccatgaaatcggcgtcccagcccatattaaaggctatctct atctgcgcgaagcaatctcaatggtatacaatgacatcgaattgctcggcagcattacaaaagtcc tctatccggacatcgccaaaaaattaacacaaccgcaagccgtgtagaaaagagcgatccgcca tgcaattgaagtggcatggagcagaggaaacattgattccatttcctcgttgtttggtatactgtca gcatgacaaaagctaaacctaccaacagtgaattcattgcaatggttgcggataagctgaggtta gagcataaggcttct (SEQ ID NO: 27) | 801 |
| gyrB | atggaacagcagcaaaacagttatgatgaaaatcagatacaggtactagaaggattggaagctg ttcgtaaaagaccggggatgtatatcggttcgacaaacagcaaaggccttcaccacctggtatgg gaaattgtcgacaatagtattgacgaagccctcgccggttattgtacggatatcaatatccaaatcg aaaaagacaacagtatcacggttgtagataatggccgcgttccagtcggtattcatgaaaaa atgggccgtcctgcggtagaagtcattatgacggtacttcatgccggaggaaaatttgacggaag cggctataaagtatccggaggattacacggtgtaggtgcgtctgtcgtaaacgcactatcaacag agcttgatgtgacggttcaccgtgacggtaaaattcaccgccaaacttataaacgcggagttccg gttacagaccttgaaatcattggcgaaacggatcatcaggaacggacacatttttgtccggga ccctgaaanttctcagaaacaaccgagtatgattatgatctgcttgccaaccgcgtacgtgaatta gcctattaacaaaggcgtaaacatcacgattgaggataaacgtgaaggacaagagcgcaaaa atgaataccattacgaaggcggaattaaaagtt atgtagagtatttaaaccgctctaaagaggttgt ccatgaagagccgatttacattgaaggcgaaaaggacggcattacggttgaagtggctttgcaat acaatagacgctacacaagcaacatttactcgtttacaaacaacattaacgactacgaaggcggt acccatgaagctggatcaaaacgggcctgactcgtgttatcaacgattacgccagaaaaaag ggcttattaaagaaaatgatccaaacctaagcggagatgacgtaagggaagggctgacagcga ttatttcaatcaaacaccctgatccgcagtttgagggccaaacgaaaacaaagctgggcaactca gaagcacggacgatcaccgatacgttattttctacggcgatgaaacattttatgctgaaaatcca gatgcagccaaaaaaattgtcgataaaggcttaatggcggcaagagcaagaatggctgcgaaa aaagcccgtgaactaacacgtcgtaagagtgattgaaatttcaaacctgccggtaagtatgc ggactgctatcaaaagatccgagcataccgagttatatcgtagagggtgactctgcggag gatctgctaaacaaggacgcagacatttccaagccattttgccgcttagaggtaaaatcctaa acgttgaaaaggccagactggataaaaatccttctaacaacgaagttcgctctatgatcacagcgc tcggcacaggtattgggaagacttcaaccttgagaaagcccgttaccacaaagttgtcattatga cagatgccgatgttgacggcgcgcacatcagaacactgctgttaacgttatttacagatatatgc gccaaattatcgagaatgctacgtgtacattgcgcagcgcgccgctctacaaggttcaacaggg gaaacgcgttgaatatgcgtacaatgacaaggagcttgaagagagttaaaaactcttcctcaaac ccctaagcctggactgcagcgttacaaaggtcttggtgaaatgaatgccacccagctatgggag acaaccatggatcctagctccagaacacttcttcaggtaactcttgaagatgcaatggatgcggac gagactatgaaatgatatgggcgacaagtagaaccgcgccgaaacttcatagaagcgaatg cgagatacgttaaaaatcttgacatctaa (SEQ ID NO: 28) | 1917 |
| comK | Atgagtcagaaaacagacgcacctttagaatcgtatgaagtgaacggcgcaacaattgcagtgc tgccagaagaaatagacggcaaaatctgttccaaaattattgaaaaagattgcgtgattatgtcaa catgaagccgctgcaaattgtcgacagaagctgccgattntgatcaagctatgcgggaagaa aagcaggaacttatgaagtgacaaaaatttcacacaagccgccgatcatggtggacccttcgaa ccaaatcttatattccctacactttcttcgacaagaccccaatgcggctggatttcccatgtgcatgt aaaagaattcaaagcgactgaatttgacgatacggaagtgacgttttcaaatgggaaaacgatgg agctgccgatctctataattcgttcgagaaccaggtataccgaacagcgtggctcagaaccaaat | 579 |

TABLE 2-continued

| Gene Name | Sequence | Size (bp) |
|---|---|---|
| | tccaagacagaatcgaccaccgcgtgccgaaaagacaggaatttatgctgtacccgaaagaag agcggacgaagatgatttatgattttattttgcgtgagctcggggaacggtattag (SEQ ID NO: 29) | |

The subject invention further comprises the srfA operon, as shown below in Table 3 below. This operon is responsible for biosurfactant biosynthesis in *Bacillus subtilis* B1, B2 and B3 strains.

The operon, which is identical in all three strains, includes genes srfAA, srfAB, srfAC, srfAD and sfp.

TABLE 3

| Gene Name | Sequence | Size (bp) |
|---|---|---|
| | atcgcacattgtcctatcgaacgttacatgagcaatctgcacgcatcgccaatgtgctgaaacagaaaggggttggcccggac | |
| | agtcctgtcgcggttttgattgaacgctctgaacggatgattacagctatcatgggaattttaaaagccggcggagcctatgt | |
| | gccgattgatccgggttttcctgctgagcgcattcaatatattttggaggactgcggggcggatttcatcctgactgaatcga | |
| | aggttgcggcgcctgaagccgatgctgagctgattgacttagatcaggcgattgaggaaggtgcagaagaaagcctgaatgca | |
| | gatgtgaacgctcggaaccttgcctacattatttacacatcgggaacaaccggacgcccgaaaggcgttatgatcgagcatcg | |
| | ccaggttcatcatttggttgaatctctgcagcagacgatttatcaaagcggcagccaaaccctgcggatggcattgcttgcgc | |
| | cgttccactttgatgcgtcagtgaagcagatcttcgcgtcgcttcttttgggccaaacccttatatcgtaccgaagaaaaca | |
| | gtgacgaacggggccgcccttactgcatattatcggaagaacagcattgaggcgacggacggaacaccggctcatttgcaaat | |
| | gctggcagcagcaggcgattttgaaggcctaaaactgaagcacatgctgatcggaggagaaggcctgtcatctgttgttgcgg | |
| | acaagctgctgaagctgttttaaagaagccggcacagcgccgcgtttgactaatgtgtacgggccgactgaaacgtgcgttgac | |
| | gcgtctgttcatccggttatccctgagaatgcagttcaatcagcgtatgtgccgatcgggaaagcgctggggaataaccgctt | |
| | atatattttggatcaaaaaggccggctgcagcctgaaggcgtggcgggtgagctttatatcgcgggagacggtgtgggccgag | |
| | gctatttacatttgcctgaattaacggaagagaagttttttacaagatccattcgtgccgggcgatcgcatgtaccggaccggg | |
| | gacgtggtgcgctggcttccagatggaacaatcgaatatttaggcagagaggatgaccaggtcaaagtccgcggataccggat | |
| | tgagcttggggaaattgaagccgtgattcagcaggcgccagacgttgcaaaagccgttgttttggcacgccctgacgaacagg | |
| | gaaatcttgaggtttgcgcatatgttgtgcagaagcctggaagcgaatttgcgccagccggtttgagggagcatgcggccaga | |
| | cagcttcctgactatatggtgccggcttactttacagaagtgacagaaattccgcttacaccaagcggcaaagtcgaccgccg | |
| | caagctgtttgcactagaggtgaaggctgtcagcggcactgcctatacagcgccgcgaaatgagactgaaaaagcaatcgcag | |
| | ccatttggcaggacgtgctgaacgttgagaaggcggggatctttgacaatttctttgaaactggcggacattcattaaaagcc | |
| | atgacccttttaacaaagattcataaggaaacaggcattgagattccgcttcaatttttgtttgagcatccgacgattacggc | |
| | tcttgcagaggaagctgatcacagagaaagcaaagcttttgcggtgattgaacctgctgaaaaacaggagcattacccgcttt | |
| | cattggcacagcagcgaacatatatcgtcagccagttcgaggatgcgggagtcggctataacatgccagcagcagcaattctg | |
| | gaagggccttagatattcaaaagctggagcgcgcatttcagggattaatccgacgccacgagtcattgagaacatcatttgt | |
| | tcttgaaaacagcacgccgagacagaaaattcacgatagcgttgatttcaacatcgaaatgattgaaagaggcggccgctcag | |
| | atgaggcaattatggcttcattcgttcggacatttgatggcgaaagctccgctgttcagaatcggatgctgggcttgaaga | |
| | gaaccgtcatatgctgctgtttgacatgcaccatttgatttctgacggtgtatccattggcattatgctggaggagttagcac | |
| | gcatttataaaggcgaacagcttcctgatcttcgtctccagtataaggactacgctgtatggcaaagcagacaggctgctgaa | |
| | gggtacaagaaggaccaggcttattggaaggaagtctttgcaggcgagctcccggtgcttcagcttctgtccgattacccaag | |
| | accacctgttcaaagctttgaaggggatcgggtgtcaatcaagctggatgcgggggtaaaggatcgcctcaatcgtttggctg | |
| | aacaaaacggcgccactttatatatggtgatgctttccgcttactatacgcttttgtcaaagtatacggggcaggatgacatc | |

TABLE 3-continued

| Gene Name | Sequence | Size (bp) |
|---|---|---|
| | attgtcgggacaccgtcagcgggcagaaatcactccgatacagagggcattatcgggatgttcgtcaatacgcttgcgattcg | |
| | cagtgaggtgaagcagaatgagacgtttacccaattgatctcgcgtgtccgcaaacgggtgctggatgccttttctcatcagg | |
| | actatccgtttgagtggcttgttgaagatttgaacatcccgcgtgatgttagcaggcatccgctgtttgacacgatgttcagc | |
| | cttcaaaacgcgacagagggcattccggctgtcggcgatcttccttgtctgttcaagagaccaatttcaagattgccaaatt | |
| | tgatttgacggtgcaggcgagagaaaccgatgaaggcattgagattgatgtggattacagcacaaagctgtttaaacaaagca | |
| | cggcagacaggctgcttacgcattttgcgcgtttgcttgaagatgctgcggctgatccagagaagccgatttctgagtataag | |
| | cttctttctgaagaggaggctgcttcgcaaattcagcagtttaacccgggcagaacaccttatccgaaagataaaacaattgt | |
| | tcagctgtttgaggagcaagcggcgaatacgccagaccacactgcgcttcaatatgaaggcgaatcactcacttatcgtgaac | |
| | tgaatgaacgggccaatcgtttagcccgcggcattctttctcttggagctggcgaaggcagaactgcggctgtcttatgcgag | |
| | cggtcaatggatatgattgtgtcgatcttggcagtattaaaatcaggttcggcttatgttccgatcgatccggaacatccgat | |
| | tcagcggatgcagcatttcttccgtgacagcggagcaaaggtgcttctcactcagaggaaattaaaggctttggcggaagaag | |
| | cggaatttaagggcgttatcgtgctagccgatgaggaagaaagctatcatgccgatgcgcgaaatctcgcactgcctcttgat | |
| | tctgcagcaatggccaacctgacgtatacttccggaacgactggaacacctaaggggaatatcgtgacacatgccaatattct | |
| | ccgcacggtgaaggaaacgaattatctcagcattacagaacaggatacgattctcggtctttccaattacgtgtttgacgcgt | |
| | ttatgttcgatatgttcggctctttgttaaacggagccaagctggtgctgataccgaaggaaaccgttttggacatggctcgc | |
| | ctgtcccgcgtcattgaacgggagaacatcagcattctcatgattacaaccgctttgttccacttgcttgtggacttgaatcc | |
| | ggcatgcttgtcaacgcttcgcaagattatgtttggcggggaacgggcttcggttgagcatgtcagaaaagctttgcaaacgg | |
| | ttggaaagggcaagctccttcatatgtatggaccgtctgaaagcacggttttcgcgacgtatcatccggttgatgaattggag | |
| | gagcacacgctgtctgttccgattggaaaaccggtcagcaatacggaagtatacattcttgaccgtacgggacacgtgcagcc | |
| | tgccgggattgccggagagctttgcgtcagcggcaaggactcgtgaaaggctattacaaccgtccagaactgactgaggaga | |
| | aatttgttccccatccgtttacatccggcgaacgcatgtataaaacgggagaccttgcgagatggctgccgaatggcgacatc | |
| | gaatttatcgggcgaatcgaccatcaggtgaagattcgcggacagcgcatcgagcttggagaaatcgaacatcagctgcaaac | |
| | ccatgatcgtgttcaggaaagtgttgtgcttgccgttgatcaaggagcgggagataaactgttgtgtgcttactatgtcggag | |
| | aaggagacatctcatcacaagagatgagagagcatgctgcgaaggacttgccggcatatatggttcctgcggtgtttatccaa | |
| | atggacgagctgccgctgacagggaacggaaaaattgaccggagagcgctgccgattcctgatgccaacgtttcaagaggtgt | |
| | ttcatatgttgcgccacgcaatggaacggaacaaaaagtcgcggacatgggcacaggtacttcaggcagaacaagtcggcgc | |
| | ttatgaccacttctugacattggcggacattcattagcaggcatgaagatgcttgccuggttcatcaggaactgggcgttgag | |
| | ctgtcactcaaggatctcttccagtcaccgacggttgagggcttggcacaggtgattgcctctgctgaaaaagggacagccgc | |
| | aagtatcagcccggcagagaaacaagatacgtatcctgtttcttccaccgcaaaaacggatgtacgtgcttcagcagcttgagg | |
| | atgcgcaaacgagctataacatgccggcggttctgcgcctgacaggtgagcttgatgttgaaaggcttaacagcgtcatgcag | |
| | cagtaatgcagcgtcatgaagccttgagaaccacgtttgaaataaaagatggagaaacggtgcagcggatctgggaagaggc | |
| | tgagtgcgagatagcctatttcgaagccccggaagaagagacagagcggatcgtttctgagtttattaagccttcaaaatcg | |
| | accaacttccactgttcagaatagggcttatcaagcattcagacactgagcatgtgctgctgttcgatatgcatcatattatt | |
| | tctgatggtgcatctgtcggtgtgctgattgaggagcttcaaagctgtacgacggagaaacccttgagccgctccgtattca | |
| | atataaggattatgccgtgtggcagcagcagttcattcagtctgagctttacaagaagcaagaagagcattggctgaaggagc | |
| | tggacggagagctgccggtgctgacgcttccgactgattacagtcggcctgccgttcaaacatttgagggagaccgcattgca | |
| | ttttcattagaagcaggcaaagctgatgctctgcgcaggcttgcaaaagaaacggattccacgctttacatggtgcttctggc | |
| | ttcatacagtgcgttttatcaaaaattagcgggcaagacgatatcatcgtcggttcacctgtggccggacgatctcaagcgg | |

TABLE 3-continued

| Gene Name | Sequence | Size (bp) |
|---|---|---|
| | acgtcagccgcgtcatcggaatgttcgtcaatacattggcgctgcgcacgtatccgaagggtgaaaagacgtttgctgactat | |
| | cttaacgaagtgaaagaaacggcactcagcgcttttgatgcgcaggattacccacttgaggatttgatcggaaatgttcagt | |
| | tcagcgtgacacaagcagaaatccgttattcgatgcagttttttcaatgcaaaatgcgaatataaaggatttaacaatgaaag | |
| | ggattcagcttgagccgcatccgtttgaacgaaaacagccaagtttgacctcacgctgacggctgacgaaaccgacggaggg | |
| | cttacattcgtactcgaatacaatacagctctgtttaagcaggaaacgattgaacgatggancaatattggatggagcttta | |
| | gatgcagttactgggaaccccgaaccagccgctttccagcctgtcactggtcaccgagacagaaaagcaagcgcttcttgaggc | |
| | atggaagggcaaagcgctgcctgtgccgacagacaaaacggttcatcagctattcgaagagactgcccagcgccacaaagacc | |
| | gcccggctgtcacatacaacggccagtcttggacgtacggcgagctgaatgcgaaggcaaaccgtctcgcgcggattctgatg | |
| | gactgcggcatcagcccggatgaccgcgtcggcgttctcacgaagccgtcgcttgaaatgtccgccgcggtgctcggcgtctt | |
| | gaaagccggagcggcgtugtgccgattgatcctgactatccggatcagcggattgagtatattttacaggacagcggcgcgaa | |
| | gcttctcttgaaacaggaaggcatttcagtgccgacagctatacgggagatgtcattcttctcgacggaagccgcacgattc | |
| | taagcctgccgcttgatgaaaacgacgaggaaaatccagaaaccgctgtaaccgcggagaacttggcgtacatgatttacacg | |
| | tctggaacgaccggacagccgaagggtgtcatggtcgagcaccatgcgcttgtgaacctgtgcttctggcaccacgacgcgtt | |
| | cagcatgacagcggaggaccgcagtgcgaagtacgcgggctttgggttcgacgcttccatttgggagatgttcccgacctgga | |
| | cgatcggtgccgaacttcacgtcattgaggaagcgatccgcctcgatatcgtccgcctgaacgattattttgaaacgaacggc | |
| | gtaacgatcacgttcctgccgacacagcttgcggaacagttcatggagcttgagaacacatcacttcgcgtattgcttactgg | |
| | aggagacaagctgaagcgcgcagtgaaaaagccgtacacactcgtcaataactacgggccgacagagaatacggtcgttgcca | |
| | caagcgcagaaatccatccggaggaaggctcgctttccatcggaagggccattgccaatacgagagtatacattctcggcgag | |
| | ggcaatcaggtgcagccggaaggcgtagccggagagctttgcgtggcggggcgcggactggcacgcggctatctgaatcgaga | |
| | agacgaaaccgcgaagcggtttgtcgctgatccgtttgtgccgggtgagcgcatgtaccgcaccggcgatttggtgaaatgga | |
| | cgggcggcgcatcgaatacatcggccggatcgaccagcaggtcaaggtccgcggctaccggatcgagctctcagaaattgaa | |
| | gtccagctcgcccagctttctgaggtgcaggatgcggcggtgacagctgtcaaagataaaggcggcaacacagcgatcgcggc | |
| | gtatgtcacaccggaatcagctgacatagaagcactgaaatcagcactgaaggaaaccctgccggattacatgatcccggcgt | |
| | tctgggtgacgctgaacgagcttccggttacggcaaacggcaaagtggaccgcaaagccttgcctgagccggacatcgaagcg | |
| | ggaagcggagaatacaaagcgccgacgaccgacatggaagagctgcttgccggcatctggcaggacgtgcttggaatgtctga | |
| | agtcggtgtcaccgacaatttcttctcgcttggcggagattccatcaaaggaattcaaatggcgagccgcttgaaccagcacg | |
| | gctggaagctggaaatgaaagatctcttccagcacccgacgatcgaagagctcacccagtacgtagagcgtgccgaaggcaaa | |
| | caggcagaccaaggcccggtggagggcgaagtcatcctgacgccgatccagcgctggttctttgaaaagaacttcacgaacaa | |
| | gcaccactggaaccaatctgtgatgcttcacgccaagaagggctttgatcctgaacgggtggagaaaacattgcaggcgctga | |
| | tcgagcatcatgacgcgctccgcatggtctatcgtgagggacaggaagacgtcattcaatacaacagaggtcttgaagctgct | |
| | tcagctcaattggaggtcatccagattgagggccaagctgcagattacgaagaccgaatagagagagaagcggagcgtttgca | |
| | aagcagcatcgacttgcaggaaggcggcttgttaaaagcaggcttgttccaagcggaagacggagatcacttgcttcttgcca | |
| | ttcaccactagtggttgacgcgtgtcgtggcgattttactggaggatttcgccgcggtatatacacagcttgagcaaggc | |
| | aatgaaccggttctcccgcagaaaacacattcatttgcagagtatgcagagagattgcaagacttcgcgaactccaaagcctt | |
| | tttgaaagaaaagagtattggagacagcttgaagaacaagctsttgcggcaaagcttccgaaagaccgcgaatctggtgatc | |
| | agcgaatgaaacatacaaagacaattgaattctcgctgactgctgaagagacagaacagctcaccacaaaggtgcatgaggca | |
| | tatcacacagaaatgaatgatattttgctgacggcattcggattggcaatgaaggagtggacgggtcaagatcgagtaagtgt | |
| | tcatttagaggggcatggacgtgaagaaatcatagaagacctgaccatttctcgcacagtcggctggtttacaagtatgtacc | |
| | caatggtgctcgatatgaagcatgcggatgatctgggctaccagctgaagcaaatgaaagaagatatcagacatgtgccgaat | |

TABLE 3-continued

| Gene Name | Sequence | Size (bp) |
|---|---|---|
| | aagggagtcggatacggcattctgcgctatctgacggcaccggaacataaagaagatgtggcgttctcgattcagccggatgt | |
| | cagcttcaactatttaggtcagtttgacgaaatgtcggatgcaggtttgtttacgagatcagagctgccatcaggacagtcat | |
| | taagccctgaaacagaaaaaccgaatgcgctggatgttgtcggatatatcgaaaacggaaaactgacgatgtcactggcctat | |
| | cattctcttgaatttcatgaaaaaacagtacaaacattcagtgacagctttaaagcgcatcttctcagaatcattgaacattg | |
| | cctatctcaagacggtacggaactgaccccgagtgatcttggtgacgacgatttgacgctggatgagctggataaattaatgg | |
| | aaattttctaatagaggtggcatatgagcaaaaaatcgattcaaaaggtgtacgcactgacaccaatgcaggagggaatgctg | |
| | tatcatgcgatgcttgatccgcattcttcctcgtacttcacacaattagagcttgggattcacggcgcttttgatcttgaaat | |
| | ctttgagaaaagcgtcaatgaactgattcggtcatacgatattctccgtacggtatttgtgcatcagcagctgcaaaaaccgc | |
| | gtcaggtcgtgttagcggaacgcaaaacaaaggtgcattatgaggatatcagtcatgcagacgagaaccgccagaaggagcac | |
| | attgagcgttacaaacaagacgttcagcgccaaggctttaacctggcaaaagacatattgttcaaggtggcggttttccgcct | |
| | tgctgcagatcagctgtatcttgtctggagcaatcatcatattatgatggacggctggagcatgggcgtcctcatgaaaagcc | |
| | tgttccaaaactatgaagcgctcagagcaggaaggacaccggcaaacggtcaaggcaagccttactccgactacatcaaatgg | |
| | cttggaaaacaggacaatgaagaagcggagagctactggagcgagcgcttggcgggttttgaacagccaagcgtgctcccggg | |
| | ccgcctgcctgtgaaaaaagacgaatacgtcaataaagaatattcctttacatgggacgaaacactggttgcccgtattcagc | |
| | aaaccgcaaatctccatcaagtgacagggcctaacctatttcaggccgtttggggcattgttctcagcaaatacaactttacg | |
| | gatgatgtggtcttcggaacggtcgtctcgggccgaccgtctgaaatcaacggcatcgaaacgatgcgggctgtttatcaa | |
| | caccattccagtgcgggtgaaagttgaacgagatgctgcattcgctgatattttcacagctgttcagcagcatgcagtagagg | |
| | cagagcgttacgattacgtgccgctctatgagattcaaaaacgctcagctcttgatggcaatctcttaaaccatctggtcgcg | |
| | tttgaaaattatccgcttgatcaagagcttgaaaacggcagcatggaagaccgctcgggttttcaattaaggtagaaagcgc | |
| | atttgaacaaacgagcttcgatttcaacctgattgtgtatccgggcaaaacgtggaccgtcaaaattaaatataacggagccg | |
| | cctttgattccgcmtatcgaacggacagcggagcaccttacccgcatgatggaagcagctgtcgatcagccggccgatttgtg | |
| | cgtgagtacgggcttgttggagacgaagagcagcggcaaattgtcgaggtgtttaacagcacgaaagccgaactccctgaagg | |
| | aatggctgttcaccaagtgtttgaagagcaagcgaaacggacgccggcgagcactgccgtcgtatatgaaggaaccgagctga | |
| | cgtaccgcgagctgaatgcagcggctaaccgtctggcgagaaagcttgtcgaacaaggccttcaaaaggggaaacagcagcg | |
| | attatgaacgatcgatcagtagaaaccgttgtcggcatgctggctgtgttaaaagcaggcgccgcatatgtgccgcttgatcc | |
| | agcgcttccggggatcgtcttcgtttcatggcagaggacagctccgttcgaatggttttgaccggaaattcttatacagggc | |
| | aggcacatcagctgcaggtgccggttcttacactggacataggcattgaagatggcgaagctgacaatctcaacctgccatcc | |
| | gccccgtctgatttggcgtacatcatgtacacatccggttcaacgggcaaaccgaaaggcgtcatgatcgaacataaaagcat | |
| | tctgcgcctcgtcaaaaatgccgggtacgttcctgttactgaagaggaccgcatggcgcaaacaggggcagtcagctttgatg | |
| | ccggaacgtttgaggtattcggcgcactgctgaatggcgcagcgctttatccggtcaaaaaagagacactgcttgatgcgaaa | |
| | caatttgctgcattcctgcgtgagcaaagcatcacaaccatgtggctgacatcacctttattcaaccagcttgcagcaaagga | |
| | tgcgggtatgttcggcacactgcgccattttaatcatcggcggagacgcccttgtcccgcatattgtcagcaaagtaaaacagg | |
| | catcgccgtcgctttcattgtggaacggatacggcccgacagaaaacacgacgttttcaaccagttttctgatcgaccgcgag | |
| | tatggcggctctatcccaatcgggaagccgatcggaaattccactgcctacatcctggatgagcagcaatgcctgcagccaat | |
| | cggcgcgcctggtgagctttgcgtaggcggaatcggtgtagcgcgtgggtatgtcaatctccctgagctgacagagaagcaat | |
| | ttctcgaagatccgttcagaccgggtgagagaatttatcgcactggtgacttggcaagatggctgccggacggcaatatcgaa | |
| | ttttttaggcagaattgacaatcaagtgaaggtgcgcggcttccgaattgagcttggcgaaattgaaacaaaactgaacatggc | |
| | tgcacatgtgacagaggctgcggtgatcatccgcaagaacaaagcggatgaaaatgaaatttgcgcgtactttacggcggacc | |

TABLE 3-continued

| Gene Name | Sequence | Size (bp) |
|---|---|---|
| | gtgaagtggctgtgagcgagctgagaaaaacactgtctcagtctttgcctgactatatggtccctgcccacctgattcaaatg | |
| | gacagtctgccgctcacgccaaacgggaaaatcaacaaaaaagaactgcctgtaccgcaatcagaagccgtgcagccggaata | |
| | cgcagcaccagaaacagagagtgaaaagaaattagcggagatctgggaaggaatactcggcgtcagagcaggcgttaccgata | |
| | acttctttatgatcggcggccattcttgaaagcgatgatgatgacggcgaaaattcaagagcatttcataaggaagttccg | |
| | ataaaagtgcttttgaaaagccgactattcaagaactggcactgtatttggaagagaacgaaagcaaggaggagcagacgtt | |
| | tgaaccgatcaggcaagcatcttatcagcagcattatcctgtatccccggcccagcggagaatgtatatcctcaatcagcttg | |
| | gacaagcaaacacaagctacaacgtccccgctgtacttctgctggagggagaagtagataaagaccggcttgaaaacgcgatt | |
| | cagcaattaatcaaccggcacgaaatcctccgtacatcgtttgacatgatcgacggagaggttgtgcaaaccgttcataaaaa | |
| | catatcgttccagctggaggctgccaagggacgggaagaagacgcggaagagataatcaaagcatttgttcagccgttgaat | |
| | taaaccgcgcgccgctcgtccgttcgaagcttgtccagctggaagaaaaacgccacctgctgctcattgatatgcatcatatt | |
| | attactgacggaagttcaacaggcattctaatcggtgatcttgccaaaatatatcaaggcgcagatctggaactgccacaaat | |
| | tcactataaagattacgcagtttggcacaaagaacaaactaattatcaaaaagatgaggaatactggctcgatgtcttaaag | |
| | gcgaactgccaatactggatcucccgcggatttcgagcggccagagaacggagctttgcgggagagcgcgtgatgtttgggct | |
| | tgataagcaaatcacggctcaaatcaaatcgctcatggcagaaacagatacgacaatgtacatgtttttgctggcggcgttca | |
| | atgtactccttccaagtacgcgtcacaggatgatatcattgtcggctcgccgacagctggcagaacacatcctgatctgcaa | |
| | ggtgtgccgggtatgtttgtcaacacggtggcactcagaacggcaccagcgggagataaaaccttcgcgcaattccttgaaga | |
| | ggtcaaaacagccagccttcaagcattcgagcaccagagctatccgcttgaggagctgattgaaaagcttccgcttacaaggg | |
| | atacaagcagaagtccgctgttcagcgtgatgttcaacatgcagaatatggagattccttcattaagattaggagatttgaag | |
| | atttcctcgtattccatgcttcatcatgttgcgaaatttgatctttccttggaagcggtcgagcgtgaagaggatatcggcct | |
| | aagctttgactatgcgactgccttgtttaaggacgagacgatccgccgctggagccgccactttgtcaatatcatcaaagcgg | |
| | ccgcggctaatccgaacgttcggctgtctgatgtagatctgcttcatctgcagaaacggctgctttgctagaagaaagacat | |
| | atgactcaaattaccgaagcaacctttgcagcacttttgaaaaacaggcccagcaaacacctgaccattctgcggtgaaggc | |
| | tggcggaaatctgttgacctatcgcgagcttgatgaacaggcgaaccagctggcgcatcatcttcgtgcccaaggggcaggaa | |
| | atgaagacatcgtcgcgattgttatggaccggtcagctgaagtcatggtatccattctcggtgtcatgaaggcggggcagct | |
| | ttccttccgattgatcctgatacacctgaagaacgaatccgttattcattagaggacagcggagcaaaatttgcggtcgtgaa | |
| | tgaaagaaacatgacggctatgggcaatatgaagggataattgtcagccttgatgacggtaaatggagaaatgaaagcaagg | |
| | agcgcccatcatccatttccgggtctcgcaatcttgcatacgtcatttatacgtccggtacgaccggaaagccaaagggcgtg | |
| | cagattgagcatcgtaatctgacaaactatgtctcttggtttagtgaagaggcgggcctgacggaaaatgataagactgtatt | |
| | gctttcatcttacgcatttgaccttggctatacgagcatgttccctgtacttctgggcggggcgagctccatatcgtccaga | |
| | aggaaacctatacggcgccggatgaaatagcgcactatatcaaggagcatgggatcacttatatcaagctgacaccgtctctg | |
| | ttccatacaatagtgaacaccgccagttttgcaaaagatgcgaactttgaatccttgcgcttgatcgtcttgggaggagaaaa | |
| | aatcatcccgactgatgttatcgccttccgtaagatgtatggacataccgaatttatcaatcactacggcccgacagaagcaa | |
| | cgatcggcgccatcgccgggcgggttgatctgtatgagccggatgcatttgcgaaacgcccgacaatcggacgcccgattgcg | |
| | aatgccggtgcgcttgtcttaaatgaagcattgaagcttgtgccgcctggagcgagcggacagctctatatcacgggacaggg | |
| | gctcgcgagagggtatctcaacaggcctcagctgacagccgagagatttgtagaaaatccatattcgccgggaagcctcatgt | |
| | acaaaaccgagatgtcgtacgaagactttctgacggtacgcttgcatttatcggccgggctgatgatcaggtgaaaatccga | |
| | ggctaccgcattgagccgaaagaaattgaaacggtcatgctcagcctcagcggaattcaagaagcggttgtactagcggtttc | |
| | cgagggcggtcttcaagagctttgcgcgtattatacgtcggatcaagatattgaaaagcagagctccggtaccagctttccc | |
| | taacactgccgtctcatatgattcctgctttctttgtgcaggttgacgcgattccgctgacggcaaacggaaaaaccgacaga | |

TABLE 3-continued

| Gene Name | Sequence | Size (bp) |
|---|---|---|
| | aacgctctgccgaagcctaacgcggcacaatccggaggcaaggccttggccgcaccggagacagcgcttgaagaaagtttatg<br>ccgcatttggcagaaaacgcttggcatagaagccatcggcattgatgacaattttttcgatttaggcggccattcattaaaag<br>ggatgatgctgattgccaacattcaggcggaattggagaaaagcgtaccgcttaaagcactgttcgagcagccgacagttcgc<br>cagctggcggcttatatggaggcgtctgctgtttcaggcggccatcaagtactcaaaccggctgacaagcaggatatgtatcc<br>attgtcatccgcacagaaacgaatgtacgtgctcaatcagcttgaccgccagacgataagctacaacatgccatctgttcttc<br>taatggaaggagagcttgatatttcgcgcctgcgcgactcactcaatcagcttgtgaaccgtcacgaatcattgcggacgtca<br>tttatggaagctaatggtgagcctgttcagcgcatcattgagaaggcggaggttgatcttcatgtgtttgaagccaaagaaga<br>cgaagcggaccaaaagattaaggaatttatccggccattcgacttaaacgacgcaccgctcattcgcgcagctttgcttcgaa<br>tagaagcgaaaaaacatttgctgcttttagatatgcatcatatcatcgcagacggcgtctcaagaggcatctttgtaaaagaa<br>ttggcgctgcttttacaaaggagagcagcttccggagccgacgcttcattataaagatttcgccgtttggcaaaatgaagctga<br>gcaaaaagaacggatgaaggagcatgaggcgtactggatgtcagttctttcaggcgagctgccagagcttgatctcccgctcg<br>attatgcccgtccgcctgtgcaaagctttaaaggagatacgatccgtttccgtacgggaagtgagacggcaaaggcggtagaa<br>aaactgcttgccgaaaccggaacgaccttgcacatggtgctccatgctgtttttccacgtcttttttaagcaaaatttccggaca<br>gcgggatatcgtcatcggctccgttactgccggccgacgaatgctgatgttcaggacatgccgggaatgttcgtcaatacac<br>ttgccctgagaatggaagcgaaagaacagcaaacatttgcggagcttttggagctagcaaagcagacgaacctgtcagccctt<br>gagcatcaggagtatccgtttgaagatctggttaatcagcttgatctccctcgggatatgagccgaaacccattgtttaatgt<br>gatggtgacgacagaaaaccctgataaagaacagcttacattgcaaaatctgagcatttcaccttatgaggctcatcagggaa<br>cttctaagtttgatctgacactgggcggatttactgatgaaaatggcattggcttgcagctcgaatatgcgacagatctgttc<br>gcaaaagaaacagctgaaaaatggagcgaatacgttctgcggctactaaaggctgttgcggataacccgaaccagccgctttc<br>cagtctgttactggtcaccgagacagaaaagcaagcgcttcttgaggcatggaagggcaaagcgctgcctgtgccgacagaca<br>aaacggttcatcagctattcgaagagactgtccagcgccacaaagaccgcccggctgtcacatacaacggccaatcttggacg<br>tacggcgagctgaacgcgaaggcaaaccgcctcgcccggattctgatggactgcggcatcagcccggatgaccgcgtcggcgt<br>tctcacgaagccgtcgcttgaaatgtccgccgcggtgctcggcgtcttgaaagccggagcggcgtttgtgccgattgatcctg<br>actacccggatcagcggattgagtatattttacaggacagcggcgcgaagcttctcttgaaacaggaaggcatttcagtgccg<br>gacagctatacgggagatgtcattcttctcgacggaagccgcacgattctaagcctgccgcttgatgaaaacgacgagggaaa<br>tccagaaaccgctgtaaccgcggagaacttggcgtacatgatttacacgtctggaacgaccggacagccgaagggtgtcatgg<br>tcgagcaccatgcgcttgtgaacctgtgcttctggcaccacgacgcgttcagcatgacagcggaggaccgcagtgcgaagtac<br>gcgggcttcgggttcgacgcttccatttgggagatgttcccgacctggacgatcggcgctgaacttcacgtcattgatgaagc<br>gatccgcctcgatatcgtccgcctgaacgattattttgaaacgaacggcgtaacgatcacgttcctgccgacacagcttgcgg<br>aacagttcatggagcttgagaacacatcacttcgcgtcctcttgaccggaggagacaagctgaagcgggcagtgaaaaagccg<br>tacacactcgtcaacaactacgggccgacagaaaatacggtcgttgccacaagcgcagaaatccatccggaggaaggctcgct<br>ttccatcggacgggccattgccaatacgagagtatacattctcggcgagggcaatcaggtgcagccggaaggcgtagccggag<br>agctttgcgtggcggggcgcggactggcacgaggctatctgaatcgagaagacgaaaccgcgaagcggtttgtcgctgatccg<br>tttgtgccgggtgaacgcatgtaccgcaccggcgacttggtgaagtgggtgaacggcggcatcgaatacatcggccggatcga<br>ccagcaggtcaaggtccgcggctaccggatcgagctctcagaaattgaagtccagctcgcccagctttctgaggtgcaggatg<br>cggcggtgacagctgtcaaagataaaggcggcaatacagcgatcgcggcgtatgtcacaccggaaacagctgacatagaagca<br>ctaaaatcaacactaaaggaaaccctgccggattacatgatcccggcgttctgggtgacgctgaacgagcttccggttacggc<br>aaacggcaaagtcgaccgcaaagccttgcctgagccggacatcgaagcgggaagcggagaatacaaagcgccgacgaccgaca | |

TABLE 3-continued

| Gene Name | Sequence | Size (bp) |
|---|---|---|
| | tggaagagctgcttgccggcatctggcaggacgtgcttggaatgtctgaagtcggtgtcaccgacaatttcttctcgcttggc | |
| | ggagattccatcaaaggaattcaaatggcgagccgcttgaatcagcacggctggaagctggaaatgaaagatctcttccagca | |
| | tccgacgatcgaagagctcacccagtacgtagagcgtgccgaaggcaaacaggcagaccaaggcccggtggagggcgaagtca | |
| | tcctgacgccgatccagcgctggttctttgaaaagaacttcacgaacaagcaccactggaaccaatcggtgatgcttcacgcc | |
| | aaaagggctttgatcctgaacgggtggagaaaacattgcaggcgctgatcgagcatcatgacgcgctccgcatggtctaccg | |
| | cgaggaaaacggggacatcgttcaggtgtataaaccgatcggtgagagcaaggtcagcttcgaaatcgtggatctgtacggct | |
| | ccgatgaagagatgctgagaagccagattaagcttctcgcgaacaagctgcaaagcagtctcgatctgcgaaacgggccgctt | |
| | ttaaaggcggagcaatatcgcacagaagctggggatcacctgctcattgctgtacaccatctcgtggtcgacggtgtgtcatg | |
| | gcggattttgcttgaagactttgcttcaggctacatgcaggctgagaaagaagagagccttgtcttcccgcaaaaaacaaact | |
| | ccttcaaggattgggcggaagaactggcggcattcagccaatcagcgcatcttttacagcaggctgaatactggtcgcaaatt | |
| | gccgctgaacaggtttctccttacctaaggattgtgaaacagagcagcggatcgtcaaggatacatcatctgtcctatgtga | |
| | attaacggcagaagacactaagcatcttttaacagatgttcatcagccatatggaactgaaatcaacgatattcttctcagcg | |
| | cgctcggtttgacaatgaaagaatggacaaaggggccaaaattggcattaaccttgagggacacggccgggaggacattatc | |
| | ccgaatgtgaatatctccagaacggtcggctggtttacggcacaatacctgttgtgctcgacatatctgacgcagatgcctc | |
| | agctgtgatcaaacagtcaaagaaaacctgcgccgcattccggacaaaggtgttggctacggcattcttcgttatttcacag | |
| | aaacagcggaaacaaagggcttcacaccggagatcagcttcaactatttgggccaattcgacagtgaagtcaaaaccgatact | |
| | ttgaaccgtccgctttcgatatggggcgcaagtaagcggagaatcagaggcgctgtacgcattaagcttcagcggcatgatc | |
| | agaaacggccggtttgtgctttcctgctatacaatgagaaggagatgaaagagctacagtcgaggagcaaatggaacggttta | |
| | aagaaaacctcctgatgctaatccgccattgcacggaaaaagaagacaaggaattcacaccaagcgacttcagcgccgaagac | |
| | cttgaaatggacgagatgggagatatctttgacatgcttgaggagaattaaaataaaacgcaagggaattacagaaggcggg | |
| | agcgaaacatatgagtcaatttagcaaggatcaggttcaagatatgtattacctatcgccgatgcaggaagggatgctttttc | |
| | atgccatcctgaatcccggccaaagcttttaccttgaacaaatcacgatgaaagtaaaaggcagcttgaatatcaaatgtctt | |
| | gaagaaagcatgaatgtgatcatgaccggtacgatgtatttcgtaccgtgttcattcacgaaaaagtaaaaaggcctgtcca | |
| | agtcgtattgaaaaaacggcagttccatatagaagaaatcgatctgacacacttaacgggcagcgagcaaacagccaaaatca | |
| | atgagtacaaagaacaggataagatcaggggttttgatttgacgcgggatattccgatgcgggcagccatttttcaagaaagct | |
| | gaagaaagctttgaatgggtgtggagctaccaccacattattttggacggatggtgcttcggcatcgtcgtacaggatctatt | |
| | taaggtatacaatgctctgcgcgaacaaaagccgtacagcctgccgcccgtcaaaccgtataaagactacatcaagtggcttg | |
| | aaaagcaggataaacaagcatcactgcgttactggcgcgaatatttagagggctttgaaggacaaacgacgtttgcggagcaa | |
| | agaaagaaacaaaaggacggctatgagccgaaagagctgctcttttcactgtcggaggcggaaacaaaggccctttaccgagct | |
| | tgcaaaatcgcagcataccactttgagtacggcgctgcaggcagtctggagcgtattgatcagccgctatcagcagtctggcg | |
| | atttggccttcggtacagttgtttcagggcgtcccgcggaaatcaaaggcgttgaacatatggtcgggctgtttatcaacgtt | |
| | gtcccgagacgtgtgaagctgtctgagggtatcacatttaacggcttgctcaagcggctgcaggagcaatcgctgcagtccga | |
| | gccgcatcaatatgtgccgctttatgacatccaaagccaggccgatcagccgaaactgattgaccacatcattgttttttgaga | |
| | actatccgcttcaggatgcgaaaaatgaagaaagcagtgaaaacggctttgatatggtggatgttcatgttttttgagaagtcg | |
| | aattatgatctcaacctgatggcttccccgggagatgagatgctgattaagcttgcctataatgagaatgtgtttgatgaggc | |
| | gtttatcctgcgdtgaaatctcagcttcttacagcaattcagcagctcatccagaatcctgatcagcctgtcagcacgatcaa | |
| | cctcgttgacgacagggagagagaattttttgctaaccggcttaaacccgccggctcaagctcatgaaacaaagcctctgacgt | |
| | attggttcaaggaagcagtgaacgccaatccggatgcaccggcgcttacgtattccggcagaccctgtcttatcgcgaatta | |
| | gatgaggaagcgaaccgcattgcacgccggctgcaaaaaacacggtgcgggcaaaggctctgttgtagcgctgtacacgaagcg | |

TABLE 3-continued

| Gene Name | Sequence | Size (bp) |
|---|---|---|
| | ctcacttgaactggtgatcggcattctcggtgtattaaaggcgggagcagcctatctgccggttgatccgaagctgccagagg accgaatctcgtatatgctggctgacagtgcggcagcctgtcttctgacgcatcaggagatgaaagaacaagcggctgagctg ccgtatacaggcacaacgctcttcattgatgatcaaacacggtttgaagaacaggcaagcgatcctgcaaccgcgattgatcc taatgatccggcatatatcatgtacacgtccggcacaaccggaaagccaaagggcaatatccaccactcatgccaatattcaag gattggtcaagcatgtagactacatggcattttctgatcaggatacgttcttgtctgtttcgaattacgcctttgatgcattt acctttgatttctatgcttctatgctgaatgcggcacggctcattatcgcagatgaacatacgctgcttgatacagaacggct cacagatctgatcctgcaagagaatgtcaatgtcatgtttgcgacaaccgcactatttaatcttctcacagatgcgggagagg attggatgaaggggcttcgctgtatattattcggcggagagcgcgcgtcagtgcctcatgtcagaaaagcgctgcggatcatg gggccgggcaagctgattaactgctacgggccgactgagggaacagtgtttgcgacagctcacgtcgtgcatgatctgccgga ttccatctcctcattgccgatcggaaagccgatcagcaatgccagtgtttatattctgaatgagcaaagccagctccagccat cggggcggtcggtgaactgtgcatcagcggaatgggcgtgtcaaaagggtatgtaaatcgtgctgacctcacgaaggaaaag tttatcgagaacccgttcaagccgggagaaacgcttacccgtacaggggatttagcgcgctggctgccggatggaacgattga atacgccggccgtattgacgaccaggtcaaaatacgcggacaccggattgagcttgaagaaatcgaaaagcagctgcaggaat acccaggtgtgaaagatgcggtcgttgtggcggaccgccatgagtctggcgatgcatcaatcaatgcctaccttgtgaaccga acgcagctttcagctgaagacgtgaaggcgcacctgaaaaaacagcttcctgcttacatggtgccgcaaacctttaccttctt ggatgagcttcctttaacgacgaacgggaaagtcaataaacggctgctcccaaaacctgatcaggatcagctggcggaagaat ggattggaccgcggaacgagatggaagaaacaatcgcacaaatatggtctgaggttctcggcagaaagcaaattggcattcat gacgatttctttgcgctcggagggcattccttgaaggccatgaccgccgcgtcccgcatcaagaaagagctcgggattgatct tccagtgaagcttttgtttgaagcgccgacgatcgccggcatttcagcgtatttgaaaaacgggggctctgatggcttgcagg atgtaacgataatgaatcaggatcaggagcagatcattttcgcattccgccggttctgggctatggccttatgtaccaaaat ctgtccagccgcttgccgtcatacaagctatgcgcctttgattttattgaggaggaagaccggcttgaccgctatgcggattt gatccagaagctgcagccgaagggccttttaacattgtttggatattcagcgggatgcagcctggcgtttgaagctgcgaaaa agcttgaggaacaaggccgtattgttcagcggatcatcatggtggattcctataaaaaacaaggtgtcagtgatctggacgga cgcacggttgaaagtgatgtcgaagcgttgatgaatgtcaatcgggacaatgaagcgctcaacagcgaagccgtcaaacacgg cctcaagcaaaaaacacatgccttttactcatactacgtcaacctgatcagcacaggccaggtgaaagcagatattgatctgt tgacttccggcgctgattttgacatgccggaatggcttgcatcatgggaagaagctacaacaggtgtttaccgtgtgaaaaga ggcttcggaacacacgcagaaatgctgcagggcgaaacgctagataggaatgcggagattttgctcgaatttcttaatacaca aaccgtaacggtttcataaatgaagtgatgaaaggaggagacagccaatgagccaactcttcaaatcatttgatgcgtcggaa aaaacacagctcatctgttttccgtttgccggcgctattcggcgtcgtttcgccctctccatgcttttttgcaggggagtg cgagatgctcgctgccgagccgccgggacacggcacgaatcaaacgtcagccattgaggatctcgaagagctgacggatttgt acaagcaagaactgaaccttcgccctgatcggccgtttgtgctgttcggacacagtatgggcggaatgatcaccttcaggctg gcgcaaaagcttgagcgtgaaggcatcttccgcaggcggttatcatttctgcaatccagccgcctcatattcagcggaagaa agtgtcccacctgcctgatgatcagtttctcgatcatattatccaattaggcggaatgcccgcagagcttgttgaaaataagg aggtcatgtccttttttcctgccttctttccgatcagattaccgggctcttgaacaatttgagctttacgatctggcccagatc cagtcgcctgttcatgtctttaacgggcttgatgataaaaatgcatacgagatgcggaagggtggaagaagtgggcaaaga catcacattccatcaatttgacggcgggcacatgttcctgctgtcacaaacggaagaagtcgcagaacggattttttgcgatct tgaatcagcatccgatcattcaaccgtgatcaaaagcggacagcttcggctgttccgcttttttttgtgttgaatgccaatttt tgcatggtataatagtcgaaatactcaaataaaggcaggttgaaacatgcgcacgtctcccaggatgaaatggtttgtattgc | |

TABLE 3-continued

| Gene Name | Sequence | Size (bp) |
|---|---|---|
| | tgtttacgtttgttttcgccatcggaatgaactcattcagaaattcctttcaatttttttatgctgccaatggcagatgccttc | |
| | catgccgacaggtcgctgatttcggtttctgtcagcattttatgatcacaaccggcatcgtccagttttttgtcggttttt | |
| | tatcgaccgtttcagtgtcagaaaattatggcgcttggagctgtctgcatcagcgcaagcttttggtgcttccttattcac | |
| | cgaatgttcatgtgttttccgccatttacggtgtgcttggcggaatcggctattcctgcgcggtcggcgtgacgacccagtac | |
| | ttcatcagccgttggtttgacacacataaaggtctggcgcttgctattttgaccaatgccaactctgcgggcctgctgcttct | |
| | ctcacccatttgggctgcggctccgtatcatgccggctggcagagcacctatacgattttgggaatcgtcatggcggctgttc | |
| | tgctgccgctcctcgtctttgggatgaagcacccgccacatgcgcaagcggaaactgtgaaaaaatcttatgattggcggggg | |
| | ttttggaacgtgatgaagcaatcccgcctcattcatatcctgtacttcggcgtgtttacttgcggatttacaatgggaattat | |
| | tgatgctcacctcgtcccgatactgaaggatgcgcatgtctctcatgtcaacggaatgatggccgcgttcggggcgtttatca | |
| | tcattggcggattattggcggggctggctgtccgatctcctcgggagcagaagcgtcatgctatccatcttatttgtcattcgg | |
| | ctgctcagcctgatttgcctgctcattcccattctcggaattcatcacagcgaactttggtattttggctttattctgttatt | |
| | cgggctcagttacacaggcgtgatcccgctgaccgcggcgtcaatttcggaaagctatcaaacaggactgatcggatcgctgt | |
| | taggcatcaatttctttatccatcaggttgccggagctcttagcgtgtatgcgggcggtttgttttttgacatgactcatggt | |
| | tatttgctgatagtcgctgtgtgcatcgtgtttgtgggtttatcggctgtaatagagctggtgccgttttagataaacagaa | |
| | ggcaaaagaaacccaccattcaatataaaaggatcagcactgtcaatgctgatccttttaaatttgagttttttgtttcgg | |
| | tatttttaaggataatctccttgaatctgttcatctcctcttcggagtgaaaaaaatgtttggggatcgcaatatattggctg | |
| | ctggatgtattgatccgaaagatattcttatattcgaaaacagctgtgatttcattccaattgaaaatgaggttatattttt | |
| | agaacttatacagattccttcttgattgagggtatatgttcttttagatttcatccgttcgttcttcttgtatgctctggaaa | |
| | acttcacatatagaagaaggaggagcagcagtgtaaacagaacggacatcacgtaatcaacatactgttcataaacaagtta | |
| | agcgcgtcactgccataaacgatacggggccatccattaatgaagttaactgcagcaaatatggcgcaaaacaacagaaagta | |
| | aaagcatgatatttttgcgatttgataaaaaaagattctcttacatccttaaaagcgatttctcctggaagattgatacttt | |
| | cattagcatattgaatcatacggtaaacctacacctctaaccatgatttcctucagtctagcataatttctcatutttgcag | |
| | gcataccagggcgctttgttttttctccagattgatattgctccccaccacgccaatcataatacaaacagcccccggcaagat | |
| | gataccaggccaggctttcgttgagaatcataactcctgcaatcatcgtcacaatggtagatacatgattaaaagcactcatt | |
| | ttaaacgcctcaattcgcgacagcgtatagttagacagaaatgaagtgacaagtgaagacagcacgcccaaatacacaatggc | |
| | gagaacgaagccgggctcccggaacggcagaaaataagtgccgactgttcccgccgctccgtgacgcacaagggcgatggcgt | |
| | tgaagacgacaaagccgatggctgacatgatgtaggtgagctcggtcagcttgaaccgctgcgtcattttctggcagcagta | |
| | ttgtacatcgctgaagacaaagcagacaataggatcagcaaagaccctttaagctggctgattccacgtcaacgcctttcat | |
| | cacaaaaataaacatgacgccggcaacggataaaaccgtgaacccctttgcgtccacgttgggcgttccttttaaaacataag | |
| | cggcaaagaccatcgtgaaaatcggaatggctgcttgaataattcccgcttcagaggaggacgagtacacaaggccgaatgcc | |
| | tgaaagctgaaaaataacgcgggatacagcagggcgagcggcaaaatggcaatgacgtcctttacgcggattgatagctttac | |
| | ccagccgaataagatcggtacagtggccgcagcaaacgcaatggtgaaccgatgcgccaaaatatcaaacggctctgctgttt | |
| | gcagtgcgattttacgaatagaaaggataaaccgataatgaacgaatataaaatagccgctatataagcggggcttgctga | |
| | tgtttaaccataatgggaagggctccttttacctgaattgcagcgccggtcgctcccttattgtatggccgcggtcagaacgg | |
| | tacaatgagaaaacaatgaactgtaccggtacaaaacaggggagaaggcatgagaaatatgagtctattaatgaggat | |
| | agaggagatgatgcaaagcaccgcctatcaagaaggagacaggcttccatctatccgtcagctgtccgcccgctaccaagtca | |
| | gcaaaagcacagtgatccgcgcgctgcaggagctggaaaagcgccaccttatctattctgttccgaaaagcggctattatatt | |
| | gtgaaaaagacagggaaatcaaaaagcgggcagcttggccccatcgactttgccacatctgcgccggatcccgatgtgutccg | |
| | tatcttgattttcagcactgtatcaacaaagcgattgatacatacaaaaacgatttgtttatttatgggacgccaaaggggct | |

TABLE 3-continued

| Gene Name | Sequence | Size (bp) |
|---|---|---|
| | tccatcactcatccgcgtactccgaaagctcttggccactcaacaggtatttgcggatgaacggcatattttcattacatcag | |
| | gtgtccagcaggcgttatccttgctttgtgccatgccgttcccaaatgggaaagagaagatcgccattgaacagccgggctac | |
| | catttgatggtcgaacagcttgagacacttgggattcccgccatcggggtgaaacgaacggaagaagggcttgatatagccga | |
| | ggttgagcggttatttcaaacagaatcgattaaattttttttatacgatgccgcgcttccataacccgcttggctgctcattgt | |
| | cagagcgtgataaacaggagcttgtgagactggcagaagcgtatgatgtctatctcgttgaggatgattacctcggtgatctg | |
| | gaggaaaataaaaaggcagatccgctgtacgcatatgatctgtcctcacatgtcatctatttgaaaagcttctcaaaaatgat | |
| | gttccccggccttcgcgtggggcggctgttttgcccgaagcgctgactgacacgttctatgcgtacaaaaagctgaacgaca | |
| | tcgactgttcgatgatttctcaagcggcattggagatttacctgaaaagcggtatgtacggcaggcataaggagaaaatcaga | |
| | gattcttataaagagcggtcgctgaggctacatcaagccattcgaactcacaggcagctgggaagcggacgctttacgttctc | |
| | cagcgggcaggcaccctgtatgcacacccatctggtgcttcctcaggatctgcccgcctcaagagtgattcatagactgaaaa | |
| | aacaagggtgatccttgaggcgatagaccgtcattatttatcagattalcagaaagaaatctattaaaaatcaatatttcc | |
| | aatgtgaaaacggaagatattgagcgcggtgtcaagctgttgatgagccatttataaaagctcttcgtacgagaccattgtga | |
| | tatcctcggggaaatcagggtgtgcggcgcatacagccattttgtagccgggatcgacctcatacgttttgatatagcatggg | |
| | gaatggctgtccggaagctcaatggatacttgtccgtcctgatgcaggcgcactgaaaaggaatcaagcggaagcgataagcc | |
| | tttgccttcctgtttgataaagctttctttcattgaccatagatgataaaaatagtctgictgctcgtccttgtatttgctaa | |
| | aaggtcgctgtactctgtattgaaaagaagcgcttggcgatctcaagactgatcggtttcgttttttcgatatctatgccgat | |
| | cggctgtgaatcaaacgcgcaaatgacccagcggccggagtgagaaatattgaaatgagcgtcgggaagatcagggatgcacg | |
| | gcttcccgtattcctgcgtgctaaagcggatatcggatttgtccaactgatactgcctgcttatgactgagcgaacgagcaca | |
| | tctcccagcagggtgcggtgagcatcttctttatgataaaatctccggcatttctcccgttttcaggtgatatgaaagacat | |
| | gaaccgttcattttcttcctgtgaaagcgggcggtccatataaattccgtaaatcttcattctagatcctccgtctgcaaaag | |
| | attgtcaaaaccatcctatcatacttccacaagactcatatagaggagaaaataaaaaaacaaagccaaggcggctttgtt | |
| | (SEQ ID NO: 43) | |

Use of B Series Microbes and their Growth by-Products in Oil Recovery

In one embodiment of the subject invention, oil recovery is improved by modifying the fluid flow through a reservoir by shifting fluid flow from high permeability zones in a reservoir to moderate or low permeability zones thus increasing the sweep efficiency by forcing the injected water to pass through previously by-passed oil zones of the reservoir. The changes in flow pattern can be achieved by an increase in microbial cell mass within the reservoir by, for example, injecting microorganisms together with nutrients. The injected nutrient and microbes preferentially flow into the high permeability zones of the reservoir and as a result of cell growth, the biomass selectively plugs these zones to a greater extent than the moderate or low permeability zones.

In one embodiment, the subject invention provides a method for enhancing the amount of oil recoverable from an oil-containing formation, wherein said method comprises applying a composition comprising a *Bacillus subtilis* B1 microbe, or a mutant thereof, and/or a growth by-product thereof, and, optionally, a carrier, to the oil-containing formation.

In one embodiment, the method further comprises administering one or more other microorganisms. In one embodiment, the other microorganisms are selected from *Bacillus*, *Geobacillus*, *Candida*, *Starmerella*, *Yarrowia*, *Pseudomonas*, *Nocardioides*, *Rhodococcus*, *Arthrobacter* and *Acinetobacter*.

Enhanced Oil Recovery Via the Alkaline-Surfactant-Polymer (ASP) Method

The B series strains of the present invention can be combined with chemical approaches to enhance oil recovery. For example, *Bacillus subtilis* strains can be used in combination with one or more alkaline compounds, polymers, surfactants, or combinations thereof.

In surfactant flooding, by reducing the interfacial tension between the oil and the displacing water and also the interfacial tension between the oil and the rock interfaces, residual oil can be displaced and recovered.

In caustic flooding, the reaction of the alkaline compounds with the organic acids in the oil forms in situ natural surfactants that lower the oil-water interfacial tension.

In addition to surfactant and alkaline flooding, polymers are used to increase the viscosity of the displacing water to improve the oil swept efficiency.

ASP flooding is a combination process in which alkali, surfactant and polymer are injected. ASP involves the injection of a solution containing polymer, alkali and surfactant into a depleted or matured oilfield with the objective of achieving optimum chemistry at large injection volumes for minimum cost. The alkali-surfactant mixture forms an emulsion with the oil, which is then swept and displaced from the reservoir using a polymer drive. ASP flooding improves microscopic displacement efficiency by reducing the interfacial tension (IFT) between the water and oil through the addition of a surfactant to the water, while matching the oil and water mobility through the addition of polymer. Alkali is also added to the water to reduce adsorption of the surfactant onto the pore walls and to control the local salinity to ensure minimum IFT and alter the rock wettability.

Use of B Series Strains with Surfactants in Oil Recovery

In certain embodiments, the methods of recovering oil described herein utilize one or more B series *Bacillus subtilis* strains combined with other compositions such as surfactants. A surfactant (Surface Active Agent) molecule has two functional groups, namely a hydrophilic (water-soluble) or polar group and a hydrophobic (oil-soluble) or non-polar group. The hydrophobic group is usually a long hydrocarbon chain (C8-C18), which may or may not be branched, while the hydrophilic group is formed by moieties such as carboxylates, sulfates, sulfonates (anionic), alcohols, polyoxyethylenated chains (nonionic) and quaternary ammonium salts (cationic).

Surfactants work in ASP flooding to lower the IFT between trapped oil and brine, to aid mobilization and contribute to the formation of oil banks. IFT reduction lowers capillary forces and allows for the oil bank to flow more freely without renewed trapping. The selection of an appropriate surfactant for EOR purposes is based on the ability to reduce IFT between crude and brine, thermal stability, tolerance to salinity and hardness of brine, solubility in brine, phase behavior parameters, adsorption test under static and dynamic condition and displacement studies under reservoir conditions.

Surfactants to be used with *Bacillus subtilis* B series strain microbes include, but are not limited to: anionic surfactants, ammonium lauryl sulfate, sodium lauryl sulfate (also called SDS, sodium dodecyl sulfate), alkyl-ether sulfates sodium laureth sulfate (also known as sodium lauryl ether sulfate (SLES)), sodium myreth sulfate; docusates, dioctyl sodium sulfosuccinate, perfluorooctanesulfonate (PFOS), perfluorobutanesulfonate, linear alkylbenzene sulfonates (LABs), alkyl-aryl ether phosphates, alkyl ether phosphate; carboxylates, alkyl carboxylates (soaps), sodium stearate, sodium lauroyl sarcosinate, carboxylate-based fluorosurfactants, perfluorononanoate, perfluorooctanoate; cationic surfactants, pH-dependent primary, secondary, or tertiary amines, octenidine dihydrochloride, permanently charged quaternary ammonium cations, alkyltrimethylammonium salts, cetyl trimethylammonium bromide (CTAB) (a.k.a. hexadecyl trimethyl ammonium bromide), cetyl trimethylammonium chloride (CTAC), cetylpyridinium chloride (CPC), benzalkonium chloride (BAC), benzethonium chloride (BZT), 5-Bromo-5-nitro-1,3-dioxane, dimethyldioctadecylammonium chloride, cetrimonium bromide, dioctadecyldi-methylammonium bromide (DODAB); zwitterionic (amphoteric) surfactants, sultaines CHAPS (3-[(3-Cholamidopropyl)dimethylammonio]-1-propanesulfonate), cocamidopropyl hydroxysultaine, betaines, cocamidopropyl betaine, phosphatidylserine, phosphatidylethanolamine, phosphatidylcholine, sphingomyelins, ethoxylate, long chain alcohols, fatty alcohols, cetyl alcohol, stearyl alcohol, cetostearyl alcohol, oleyl alcohol, polyoxyethylene glycol alkyl ethers (Brij): $CH_3$-$(CH_2)10$-$16$-$(O$—$C_2H_4)1$-$25$-$OH$ (octaethylene glycol monododecyl ether, pentaethylene glycol monododecyl ether), polyoxypropylene glycol alkyl ethers: $CH_3$-$(CH_2)10$-$16$-$(O$—$C_3H_6)1$-$25$-$OH$, glucoside alkyl ethers: $CH_3$-$(CH_2)10$-$16$-$(O$-Glucoside$)1$-$3$-$OH$ (decyl glucoside, lauryl glucoside, octyl glucoside), polyoxyethylene glycol octylphenol ethers: $C_8H_{17}$-$(C_6H_4)$-$(O$—$C_2H_4)1$-$25$-$OH$ (Triton X-100), polyoxyethylene glycol alkylphenol ethers: $C_9H_{19}$-$(C_6H_4)$-$(O$—$C_2H_4)1$-$25$-$OH$ (nonoxynol-9), glycerol alkyl esters (glyceryl laurate), polyoxyethylene glycol sorbitan alkyl esters (polysorbate), sorbitan alkyl esters (spans), cocamide MEA, cocamide DEA, dodecyldimethylamine oxide, copolymers of polyethylene glycol and polypropylene glycol (poloxamers), and polyethoxylated tallow amine (POEA).

Anionic surfactants contain anionic functional groups at their head, such as sulfate, sulfonate, phosphate, and carboxylates. Prominent alkyl sulfates include ammonium lauryl sulfate, sodium lauryl sulfate (also called SDS, sodium dodecyl sulfate) and the related alkyl-ether sulfates sodium laureth sulfate, also known as sodium lauryl ether sulfate (SLES), and sodium myreth sulfate. Carboxylates are the most common surfactants and comprise the alkyl carboxylates (soaps), such as sodium stearate.

Surfactants with cationic head groups include: pH-dependent primary, secondary, or tertiary amines; octenidine dihydrochloride; permanently charged quaternary ammonium cations such as alkyltrimethylammonium salts: cetyl trimethylammonium bromide (CTAB) a.k.a. hexadecyl trimethyl ammonium bromide, cetyl trimethylammonium chloride (CTAC); cetylpyridinium chloride (CPC); benzalkonium chloride (BAC); benzethonium chloride (BZT); 5-Bromo-5-nitro-1,3-dioxane; dimethyldioctadecylammonium chloride; cetrimonium bromide; and dioctadecyldi-methylammonium bromide (DODAB).

Zwitterionic (amphoteric) surfactants have both cationic and anionic centers attached to the same molecule. The cationic part is based on primary, secondary, or tertiary amines or quaternary ammonium cations. The anionic part can be more variable and include sulfonates. The most common biological zwitterionic surfactants have a phosphate anion with an amine or ammonium, such as the phospholipids phosphatidylserine, phosphatidylethanolamine, phosphatidylcholine, and sphingomyelins.

A surfactant with a non-charged hydrophilic part, e.g. ethoxylate, is non-ionic. Many long chain alcohols exhibit some surfactant properties.

Use of B Series Strains with Polymers in Oil Recovery

The present invention provides for methods of recovering oil using one or more *Bacillus subtilis* B series strains combined with polymer compounds. Polymer compounds used to recover oil in combination with the *Bacillus subtilis* strains of the present invention include but are not limited to: hydrogels, acrylic acid, acrylamide, polyacrylamide, hydrolyzed polyacrylamide (HPAM), polysaccharide, xanthan gum, guar gum, and cellulose polymer.

The associative water-soluble polymer is a relatively new class of polymers that has recently been introduced for oilfield applications. These polymers consist of a hydrophilic long-chain backbone, with a small number of hydrophobic groups localized either randomly along the chain or at the chain ends. When these polymers are dissolved in water, hydrophobic groups aggregate to minimize their water exposure. The incorporated groups associate due the intramolecular hydrophobic interactions and the intermolecular hydrophobic interactions. The functional groups on these polymer are less sensitive to brine salinity compared to polyacrylamide, whose viscosity dramatically decreases with increasing salinity.

Polymer flooding may involve addition of polymer to the water of a water-flood to decrease its mobility. Polymers increase the viscosity of the aqueous phase as well as reduces water permeability due to mechanical entrapment, consequently resulting in more favorable mobility ratio. With a more viscous phase, the collected oil bank can be more easily moved through the reservoir and eventually into the producing well.

Use of B Series Strains with Alkaline Compounds in Oil Recovery

The present invention provides for methods of recovering oil using one or more *Bacillus subtilis* B series strains combined with alkaline compounds. Alkaline compounds used to recover oil in combination with the *Bacillus subtilis* strains of the present invention include but are not limited to: sodium hydroxide, sodium carbonate, sodium hydrogen carbonate, sodium silicate, sodium orthosilicate and combinations thereof.

Alkali is a basic, ionic salt of an alkali metal or alkaline earth metal element. The use of alkali in a chemical flood offers several benefits including promoting crude oil emulsification, increasing aqueous-phase ionic strength leading to regulation of phase behavior of the injected surfactant, and lowering IFT to ultralow values in presence of surfactant.

Alkali can also reduce costs by limiting the amount of surfactant needed in two ways. First, alkali reduces surfactant adsorption by increasing the rock surface's negative charge density, making it preferentially water-wet. Second, alkali reacts with the acids in the crude oils to produce in situ soaps, which in turn broadens the optimal salinity range. The soap generated creates a microemulsion phase that can co-exist with oil and water, thus extending the three-phase region (or ultra-low IFT region).

Selection of alkali is guided by the type of formation, clay type and divalent cations. Common alkaline agents include sodium hydroxide (NaOH, or caustic soda), sodium carbonate ($Na_2CO_3$, or soda ash), sodium bicarbonate ($NaHCO_3$) and sodium metaborate ($NaBO_2$). Sodium hydroxide solutions have been reported to strongly interact with sandstone at elevated temperature (185° F.), resulting in sandstone weight loss and increased porosity. Caustic consumption resulting from NaOH dissolution of silicate minerals can be a significant and detrimental factor during field application. Anionic surfactants showed much smaller adsorption in the presence of $Na_2CO_3$ compared to NaOH. The hydroxide is not a potential determining ion for carbonate surfaces. Calcium and other divalent cations can cause precipitation of alkalis such as $Na_2CO_3$ unless soft brine is used. This is limitation of $Na_2CO_3$. The use of $NaBO_2$ as a replacement for $Na_2CO_3$ has been reported. This alkali gave pH values of about 11 at 1 wt % alkali concentration and generated soap for acidic crude oils. Another major advantage of $NaBO_2$ (sodium metaborate) species are their tolerance to divalent cations. In carbonate reservoirs sodium metaborate is used in place of other alkalis. If reservoir contains clays $NaHCO_3$ is preferred. $Na_2CO_3$ is the most commonly used alkali because it is inexpensive and transports better in porous media.

The preferred oil formations for alkaline flooding are sandstone reservoirs rather than carbonate formations that contain anhydrite (calcium sulfate) ($CaSO_4$) or gypsum (calcium sulfate dehydrate) ($CaSO_4.2H_2O$), which can consume large amounts of alkaline chemicals. Also, in carbonate reservoirs the calcium carbonate ($CaCO_3$) or calcium hydroxide ($Ca(OH)_2$) precipitation occurs when $Na_2CO_3$ or NaOH is added. Carbonate reservoirs also contain brine with a higher concentration of divalents and could cause precipitation. To overcome this problem, suggested $NaHCO_3$ and sodium sulfate ($Na_2SO_4$) is used. $NaHCO_3$ has a much lower carbonate ion concentration, and additional sulfate ions can decrease calcium ion concentration in the solution. These chemicals are also consumed by clays, minerals, or silica, and the higher the temperature of the reservoir the higher the alkali consumption. Another common problem during caustic flooding is scale formation in the producing wells. During alkaline flooding, the injection sequence usually includes: (1) a preflush to condition the reservoir before injection of the primary slug, (2) primary slug (alkaline chemicals), (3) polymer as a mobility buffer to displace the primary slug. Alkaline flooding can be modified as the AP (alkali-polymer), AS (alkali-surfactant), and Alkali-Surfactant-Polymer (ASP) processes. Soap produced from the reaction between the acidic components of a crude oil and the injected alkali is the principal mechanism of oil recovery in alkaline flooding.

Currently, the dominant method of enhanced oil recovery is the alkali-surfactant-polymer (ASP) method. The methods of the present invention are able to: produce surfactant in an oil well; create biofilm; and add an alkaline compound to buffer the well and increase efficiency of the all the compounds—adding to the synergistic effect seen in chemically based enhanced oil recovery procedures. The standard ASP technique has these same functions but the compositions and methods of the present invention are more advantageous. The main advantages of the present invention are: the ability of microbes to self-generate; the non-toxic properties of the microbes; and the lack of harm to the crude oil caused by the microbes. The current ASP methods do not self-generate, are toxic and often harm the oil—lessening the efficiency of recovery compared to microbial enhanced oil recovery (MEOR) in the present invention.

Use of B Series Microbes in Environmental Remediation

The subject invention provides improved methods of enhancing oil degradation from oil spills utilizing *Bacillus subtilis* B series microbes. At sites of oil spills (both on land and off shore), *Bacillus subtilis* (or B series strain) microbes of the present invention are deployed to aid in clean up and removal of contaminating oil.

An oil spill is the release of a liquid petroleum hydrocarbon into the environment, especially marine areas, due to human activity, and is a form of pollution. The term is usually applied to marine oil spills, where oil is released into the ocean or coastal waters, but spills may also occur on land. Oil spills may be due to releases of crude oil from tankers, offshore platforms, drilling rigs and wells, as well as spills of refined petroleum products (such as gasoline, diesel) and their by-products, heavier fuels used by large ships such as bunker fuel, or the spill of any oily refuse or waste oil.

Cleanup and recovery from an oil spill is difficult and depends upon many factors, including the type of oil spilled, the temperature of the water (affecting evaporation and biodegradation), and the types of shorelines and beaches involved. Presently, spills may take weeks, months or even years to clean up. The methods and compositions of the present invention provide for safer and less polluting cleanup of oil spills.

Use of the B Series Microbes to Produce Biosurfactants

In one embodiment, the B series microbes of the subject invention can be used to produce one or more biosurfactants.

Microbial biosurfactants are compounds produced by a variety of microorganisms such as bacteria, fungi, and yeasts. Biosurfactants form an important class of secondary metabolites that occur in many microorganisms such as *Pseudomonas* species (*P. aeruginosa, P. putida, P. florescens, P. fragi, P. syringae*); *Flavobacterium* spp.; *Bacillus* spp. (*B. subtilis, B. pumillus, B. cereus, B. licheniformis*); *Candida* species (*C. albicans, C. rugosa, C. tropicalis, C. lipolytica, C. torulopsis*); *Rhodococcus* sp.; *Arthrobacter* spp.; *campylobacter* spp.; *cornybacterium* spp. and so on.

Safe, effective microbial bio-surfactants reduce the surface and interfacial tensions between the molecules of liquids, solids, and gases. As discussed herein, this activity can be highly advantageous in the context of oil recovery. This dynamic can also be used to, for example, facilitate plant health, increase yields, manage soil aeration, and responsibly utilize available irrigation water resources.

Thus, in one embodiment, the biosurfactants can be used to improve the health and productivity of plants undergoing water stress.

Biosurfactants are unique in that they are produced via microbial fermentation but have those properties possessed by chemical surfactants in addition to other attributes not possessed by their synthetic analogs. Biosurfactants decrease the tendency of water to 'pool', they improve the 'adherence' or 'wettability' of surfaces, which results in more thorough hydration of the full rhizosphere, and they reduce the volume of water that might otherwise 'escape' below the root zone via micro-channels formed by drip and micro-irrigation systems. This 'wettability' also promotes better root system health as there are fewer zones of desiccation (or extreme dryness) inhibiting proper root growth and better availability of applied nutrients as chemical and micro-nutrients are more thoroughly made available and distributed.

The more uniform distribution of water in the crop rhizosphere made possible by enhanced 'wettability' also prevents water from accumulating or getting 'trapped' above optimal penetration levels thereby mitigating anaerobic conditions that inhibit the free exchange of oxygen and carbon. Once an efficacious biosurfactant is applied a more porous or 'breathable' crop rhizosphere is established and roots will have greater resistance to soil borne disease. The combination of a properly hydrated and aerated rhizosphere also increases the susceptibility of soil pests and pathogens (such as nematodes and soil borne fungi and their spores) to chemical pesticides and biopesticides. Biosurfactants can be used for a wide range of useful applications include disease and pest control Biosurfactants produced according to the subject invention can be used for other, non-agriculture and non-oil recovery purposes including, for example, cleaning pipes, reactors, and other machinery or surfaces.

Biosurfactants according to the subject invention include, for example, low-molecular-weight glycolipids (GLs), lipopeptides (LPs), flavolipids (FLs), phospholipids, and high-molecular-weight polymers such as lipoproteins, lipopolysaccharide-protein complexes, and polysaccharide-protein-fatty acid complexes.

In one embodiment, the microbial biosurfactant is a glycolipid such as a rhamnolipid, sophorlipids (SLP), trehalose lipid and/or mannosylerythrithol lipid (MEL).

In one embodiment, the microbial biosurfactant is surfactin.

Use of the B Series Microbes as Microbial Inoculants

In one embodiment, the microbe-based product is a microbial inoculant. When applied to, for example, seed, plant, or soil of row crops, forestry operations, managed pastures, horticulture crops, managed turf, animal waste and/or animal feeds the inoculant becomes an integral part of the property of the host soil or host medium and promotes the healthy growth of indigenous, beneficial microorganisms that benefit that soil or medium or plants and animals that are grown, fed or otherwise exposed to these soils and media. Once applied to the soil, microbial inoculants of the subject invention improve the mineralization of organic matter, increase nitrogen fixation needed for photosynthesis, increase phosphorous availability to crops while limiting its environmental leaching, produce beneficial plant signaling metabolites, stimulate root mass facilitating uptake of water and key nutrients, improve soil fertility, and/or boost biomass.

In one embodiment, the inoculants can be customized by crop or geography to facilitate the robust colonization of beneficial microorganisms, which makes this technology ideal for proactively managing specific crops grown in vastly different soil ecosystems. The ability to customize microbials to suit the needs of different soil ecosystems becomes even more important as a better understanding is developed of how complex microbial communities react to extreme temperatures, prolonged drought, variable rainfall, and other impacts stemming from climate change and intensive farming.

Because of the high density of vegetative cells in certain embodiments of the subject invention, the microbe-based products of the subject invention are uniquely advantageous in their ability to colonize an environment, such as soil, and to interact in a favorable fashion with the existing microflora. Due to the exceptional high cell counts, particularly of vegetative cells, the microbe-based products of the subject invention make it possible for extended survival of the microbes in the soil (or other relevant environment). This survival can be further enhanced and extended by, for example, providing the microbes with nutrients.

In one embodiment of the subject invention, the survival and retention of the microbes is monitored by tracking and/or quantifying the microbes and/or their movement in the soil or other environment.

Use of the B Series Microbes as Biocontrol Agents

In another embodiment, the microbe-based product is a biocontrol agent. Compared to conventional synthetic chemical pesticides that can pollute the environment and adversely affect non-target plants and animals, biopesticides are non-toxic, safe to use, and can have high specificity. Best used as a preventative rather than curative tool to manage weeds, diseases, nematodes and insects and other pests, biopesticides allow farmers to reduce their traditionally heavy reliance on chemical-based pesticides and herbicides without affecting crop yields. Biopesticides help create an environmental where pests are unable to gain a foothold and thrive, which is a critical benefit given the proliferation of agricultural pests linked to extreme weather. Use of biopesticides also enables farmers to reduce soil contamination for rotational crops, toxicity to non-target plants and animals, crop toxicity, development of pesticide resistance and runoff and leaching to environmentally sensitive areas, water supplies, etc. and other consequences of using chemical pesticides.

Resistance to chemically-based pesticides is of major concern as resistant pests and insects threaten agricultural productivity and are costly to combat once resistance develops.

Nematode Control Using B Series Microbes and/or Their Growth By-Products

In one embodiment, the subject invention provides methods and compositions, based upon B series microbes and their growth by-products.

Nematodes are a class of worms of the phylum Nemathelminthes roundworms or threadworms. Nematodes are also known as eelworms. Examples in the class are the cyst forming nematodes of the genus *Heterodera* (e.g. *H. glycines*, *H. avenae*, and *H. shachtii*) and *Globodera* (e.g. *G. rostochiens* and *G. pallida*), the stubby root nematodes of the genus *Trichodorus*, the bulb and stem nematodes of the genus *Ditylenchus*, the golden nematode, *Heterodera rostochiensis*, the root knot nematodes, of the genus *Meloidogyne* (e.g. *M. javanica*, *M. hapla*, *M. arenaria* and *M. incognita*), the root lesion nematodes of the genus *Pratylenchus* (e.g. *P. goodeyi*, *P. penetrans*, *P. bractrvurus*, *P. zeae*, *P. coffeae*, *P. bractrvurus*, and *P. thornei*), the citrus nematodes of the genus *Tylenchulus*, the sting nematodes of the genus *Belonalaimus*, and the plant-parasitic nematodes of genera such as *Naccobus*, *Radopholus*, and others such as the genus *Xiphinema*, particularly X index and *X. italiae*, *X. americanum* and *X. diversicaudatum*.

In one embodiment, microbes and/or their growth by-products such as surfactin, can be used to protect crop plants, homes, structures, soils, aquatic systems, ponds, fish aquariums, humans, or animals by controlling nematodes. In one embodiment, the method of controlling nematodes comprises steps of obtaining a microbial biosurfactant, and providing an effective amount of the microbial biosurfactant to nematodes or to their locus.

In one embodiment, the composition for controlling nematodes according to the subject invention comprises an effective amount of a microbial biosurfactant and/or a microorganism producing such biosurfactant.

In a specific embodiment, the methods and compositions of the subject invention are capable of preventing damage to crops from pests, in particular, nematodes and increasing yields of agricultural crops. The prevention of nematode damage and increase in yields of crops may be achieved by applying the composition before, during, and/or after the pests are initially present.

In one embodiment, the composition can be applied to the already germinated and/or grown plant including roots, stems, and leaves. The composition may also be applied as a seed treatment. The use as a seed treatment is beneficial because the application can be achieved easily, and the amount used for treatment may be reduced.

In one embodiment, the composition may be applied to the soil, plants' growing medium, plants, aquatic medium, or any area to be treated and to prevent pest damage.

The microorganisms in the composition can be grown onsite and produce the biosurfactants onsite to control nematodes. In one embodiment, the cultivation process for producing the composition of the invention is carried out in a vessel that can be any fermenter or cultivation reactor. The product of the microbial cultivation containing the microbial biosurfactant may be used directly for nematode treatments without extraction or purification. If desired, extraction and purification of the biosurfactant can be easily achieved using standard techniques.

In another embodiment, the composition for controlling nematodes may comprise a mixture of different biosurfactants or a mixture of microbial biosurfactants and microorganisms producing these biosurfactants to perform the functions and achieve the results disclosed herein.

As used herein, the term "control" used in reference to the activity produced by the biosurfactants or biosurfactant-producing organisms extends to the act of killing, disabling or immobilizing pests or otherwise rendering the pests substantially incapable of causing harm.

Substances that enhance the growth of microorganisms and the production of biosurfactants may also be added to the composition and/or the treatment site. These substances include, but are not limited to, oil, glycerol, sugar, or other nutrients. For example, a carbon substrate that supports the growth of the biosurfactant-producing microorganisms may be added to the composition or the targetted areas. Biosurfactant producing organisms can grow on the substrate to produce biosurfactant in place and control nematodes.

Carbon substrates can include, but are not limited to, organic carbon sources such as natural or synthetic oil including used frying oil; fat; lipid; wax (natural or paraffin); fatty acids such as lauric; myristic, etc; fatty acid alcohol such as lauryl alcohol; amphiphilic esters of fatty acids with glycerol such as glyceryl monolaurate; glycol esters of fatty acid such as polyethylene monostearate; fatty acid amines such as lauryl amine; fatty acid amides; hexanes; glycerol; glucose; etc. It is preferable to use a water insoluble carbon substrate to encourage production of the biosurfactants.

Although it is not necessary, it is preferable to spike or amend the carbon substrate with a sufficient amount of specific biosurfactant to initiate the emulsification process and to inhibit or reduce the growth of other competing organisms for the biosurfactant-producing organism and to control nematodes. *Pseudomonas syringae* and *Bacillus subtilis* for instance produce a series of lipopeptides biosurfactants referred to as porens. These lipopeptide porens include pseudomycin, syringomycin, tabtoxin, phaseolotoxin, and surfactin.

In one embodiment, the composition for controlling nematodes comprises a biosurfactant selected from low-molecular-weight glycolipids (GLs), lipopeptides (LPs), flavolipids (FLs), phospholipids, and high-molecular-weight polymers such as lipoproteins, lipopolysaccharide-protein complexes, and polysaccharide-protein-fatty acid complexes.

In one embodiment, the microbial biosurfactant is a glycolipid such as a rhamnolipid, sophorlipids (SLP), trehalose lipid and/or mannosylerythrithol lipid (MEL).

In one embodiment, the composition for controlling nematodes comprises SLP. The composition preferably contains the active components, such as the SLP, at concentration of 0.01 to 90 by weight % (wt %), preferably 0.1 to 50 wt %, and more preferably 0.1 to 20 wt %.

In another embodiment, the composition for controlling nematodes comprises a mixture of SLP and MEL. The composition is preferably containing the active components, the combination of SLP and MEL, at concentration of 0.01 to 90 by weight % (wt %), preferably 0.1 to 50 wt %, and more preferably 0.1 to 20 wt %.

Due to their powerful activity on cells and tissues, these biosurfactants are very useful in controlling nematodes. If it is desired to encourage the growth of *Bacillus subtilis*, a small amount of surfactin biosurfactant is added to the carbon substrate medium to aid in establishment of *subtilis* population and the production of more surfactin on-site.

In general, the effectiveness of pesticides can be significantly enhanced if they are able to readily spread on the treated surface and to penetrate into the pest (e.g., into the insects' cuticle). According to preferred embodiments of this invention, the biopesticide is able to penetrate through pests' tissues sufficiently and is effective in lesser amounts without the use of adjuvants. It has been found that at concentrations above the critical micelle concentration, the biosurfactants are able to penetrate more effectively into treated objects.

Advantageously, natural biosurfactants are able to inhibit the growth of competing organisms and enhance the growth of the specific biosurfactant producing organisms.

In addition, these biosurfactants may be used to treat human diseases such as ova-parasites and cysts, hair dandruff, etc. Examples of animal diseases include, but not limited to, dog's heart worm; fish parasites and microbial infections such as whirling disease caused by the amoeba Myxobolus, fish fungal disease (water mold) or green algae; fish protozoa disease such as Chilodonella; fish parasites as gill and skin flukes. Also cattle hoof diseases can also be controlled as described in this invention. Animals are treated by dipping or bathing in a biosurfactant solution alone or in the presence of other compounds such as copper or zinc.

The natural biosurfactants' active components may be used according to the invention either alone or combined with other acceptable active or inactive (inert) components that may be used as adjuvants or may have pesticidal activity. These components can be, for example, an oil component such as cinnamon oil, clove oil, cottonseed oil, garlic oil, or rosemary oil; another natural surfactant such as Yucca or Quillaja saponins; or the component may be an aldehyde such as cinnamic aldehyde. Other oils that may be used as a pesticidal component or adjuvants include: almond oil, camphor oil, castor oil, cedar oil, citronella oil, citrus oil, coconut oil, corn oil, eucalyptus oil, fish oil, geranium oil, lecithin, lemon grass oil, linseed oil, mineral oil, mint or peppermint oil, olive oil, pine oil, rapeseed oil, safflower oil, sage oils, sesame seed oil, sweet orange oil, thyme oil, vegetable oil, and wintergreen oil.

Other suitable additives, which may be contained in the formulations according to the invention, include substances that are customarily used for such preparations. Example of such additives include adjuvants, surfactants, emulsifying agents, plant nutrients, fillers, plasticizers, lubricants, glidants, colorants, pigments, bittering agents, buffering agents, solubility controlling agents, pH adjusting agents, preservatives, stabilizers and ultra-violet light resistant agents. Stiffening or hardening agents may also be incorporated to strengthen the formulations and make them strong enough to resist pressure or force in certain applications such as soil, root flare or tree injection tablets.

In one embodiment, the composition may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, Potassium carbonate or bicarbonate, hydrochloric acid, nitric acid, sulfuric acid or a mixture.

In one embodiment, additional components such as an aqueous preparation of a salt as polyprotic acid such as sodium bicarbonate or carbonate, sodium sulfate, sodium phosphate, sodium biphosphate, can be included in the formulation.

In one embodiment, the microbial biopesticides may be produced and formulated in a variety of ways, including liquid, solids, granular, dust, or slow release products by means that will be understood by those of skill in the art.

Local Production of B Series Microbe Products

Advantageously, in preferred embodiments, the systems of the subject invention harness the power of naturally-occurring local microorganisms and their metabolic by-products to nourish, invigorate, and protect crop ecosystems and the communities and environments in which these ecosystems exist. Enhancement of local microbial populations can be advantageous in other settings as well, including, but not limited to, environmental remediation (such as in the case of an oil spill), animal husbandry, aquaculture, forestry, pasture management, turf, horticultural ornamental production, waste disposal and treatment, mining, oil recovery, and human health, including in remote locations.

Local B series microbes can be identified based on, for example, salt tolerance, ability to grow at high temperatures, and through the use of genetic identification of the sequences described herein.

Locally-produced high density, robust cultures of microbes are more effective in the field than those that have undergone vegetative cell stabilization, have been sporulated or sat in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention can be located at the location where the microbe-based product will be used (e.g., farm, forest, pasture, feedlot, mining, waste treatment, park, remediation, oil well or aquaculture facility) or near the location of use. For example, the microbe growth facility may be less than 300, 250, 200, 150, 100, 75, 50, 25, 15, 10, 5, 3, or 1 mile from the location of use.

Because the microbe-based product is generated locally, without resort to the microorganism stabilization, preservation, storage and transportation processes of conventional microbial production, a much higher density of live bacteria in the vegetative state can be generated, thereby requiring a smaller volume of the microbe-based product for use in the on-site application or which allows much higher density microbial applications where necessary to achieve the desired efficacy. This allows for a scaled-down bioreactor (e.g., smaller fermentation tank, smaller supplies of starter material, nutrients, pH control agents, and defoaming agents) that makes the system efficient. Local generation of the microbe-based product also facilitates the inclusion of the growth broth in the product. The broth can contain agents produced during the fermentation that are particularly well-suited for local use.

In one embodiment, the composition according to the subject invention is obtained through cultivation processes ranging from small (e.g., lab setting) to large (e.g., industrial setting) scales. These cultivation processes include, but not limited to, submerged cultivation/fermentation, surface cultivation, solid state fermentation (SSF), and combination thereof.

Transformed B Series Microbes

In one embodiment, the subject invention pertains to the genetic transformation of host cells (e.g., Gram positive or Gram negative bacteria) so as to provide these bacteria with the ability to over-produce surfactin. Thus, the subject invention allows the use of recombinant strains of Gram positive and/or Gram negative bacteria for the production of surfactin and/or the use of these recobinant B series strains as described herein.

In one aspect of the subject invention yeast, Gram negative and/or Gram positive organisms are transformed with one or more of the disclosed nucleic acid sequences of the srfA operon. The organisms that are transformed may, or may not, contain a naturally occurring srfA operon. In some embodiments, the transformed organism lacks a naturally occurring srfA operon.

To impart to a microorganism the ability to produce one or more of the elements of the srfA operon disclosed herein, a single nucleic acid comprising all of the elements (e.g., SEQ ID NOs: which encodes the entire operon]) of the operon can be provided to a bacterial cell via transformation or any other means (e.g., chromosomal integration). These elements may be used for the direct production of surfactin.

These elements may also be used to construct an expanded cassette to include other elements. Constructs may also be generated to include genes encoding, for example, enzymes. Thus, this single nucleic acid can be in the form of a transposon element, genetic construct or a vector, such as a plasmid.

Alternatively, individual nucleic acids (e.g., genes) encoding components of the operon can be used to transform the host cell. Thus, a single nucleic acid molecule according to the subject invention can contain one or any combination of genes of the srfA operon. Again, the individual nucleic acids encoding polypeptides of the operon can be incorporated into a plasmid or other genetic construct that is used to transform a host organism.

The host cell may be, selected from, for example, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium amrnoniagenes, divaricatum, Brevibacterium lactofermentum, Brevibacterium flavum, Brevibacterium globosum, Brevibacterium fuscum, Brevibacterium ketoglutamicurn, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanutn, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus coagulans, Escherichia freundii, Microbacterium ammoniaphilum, Serratia marcescens, Salmonella typhimurium, Salmonella schottmulleri, Xanthomonas citri, Thermotoga martima, Geobacillus sterothermophilus* and so forth (in certain embodiments, thermotolerant microorganisms, such as a thermotolerant *B. coagulans* strain are preferred).

In some embodiments, the host cells for expression of the polypeptides include, and are not limited to, those taught in U.S. Pat. Nos. 6,319,691; 6,277,375; 5,643,570; or 5,565,335; each of which is incorporated by reference in its entirety, including all references cited within each respective patent.

The subject invention provides, in one embodiment, methods for the identification of the presence of nucleic acids according to the subject invention in transformed host cells. In these varied embodiments, the invention provides for the detection of nucleic acids in a sample (obtained from a cell culture) comprising contacting a sample with a nucleic acid (polynucleotide) of the subject invention (such as an RNA, mRNA, DNA, cDNA, or other nucleic acid). In a preferred embodiment, the polynucleotide is a probe that is, optionally, labeled and used in the detection system.

Many methods for detection of nucleic acids exist and any suitable method for detection is encompassed by the instant invention. Typical assay formats utilizing nucleic acid hybridization includes, and are not limited to, 1) nuclear run-on assay, 2) slot blot assay, 3) northern blot assay (Alwine et al., 1977, 4) magnetic particle separation, 5) nucleic acid or DNA chips, 6) reverse Northern blot assay, 7) dot blot assay, 8) in situ hybridization, 9) RNase protection assay (Melton et al., 1984) and as described in the 1998 catalog of Ambion, Inc., Austin, Tex., 10) ligase chain reaction, 11) polymerase chain reaction (PCR), 12) reverse transcriptase (RT)-PCR (Berchtold, 1989), 13) differential display RT-PCR (DDRT-PCR) or other suitable combinations of techniques and assays. Labels suitable for use in these detection methodologies include, and are not limited to 1) radioactive labels, 2) enzyme labels, 3) chemiluminescent labels, 4) fluorescent labels, 5) magnetic labels, or other suitable labels. These methodologies and labels are well known in the art and widely available to the skilled artisan. Likewise, methods of incorporating labels into the nucleic acids are also well known to the skilled artisan.

Thus, the subject invention also provides detection probes (e.g., fragments of the disclosed polynucleotide sequences) for hybridization with a target sequence or the amplicon generated from the target sequence. Such a detection probe will comprise a contiguous/consecutive span of at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides of SEQ ID NO: 1, 3, 5, 7, 9, 11, 13, 15, 17, 19 or 21. Labeled probes or primers are labeled with a radioactive compound or with another type of label as set forth above (e.g., 1) radioactive labels, 2) enzyme labels, 3) chemiluminescent labels, 4) fluorescent labels, or 5) magnetic labels). Alternatively, non-labeled nucleotide sequences may be used directly as probes or primers; however, the sequences are generally labeled with a radioactive element ($^{32}P$, $^{35}S$, $^{3}H$, $^{125}I$) or with a molecule such as biotin, acetylaminofluorene, digoxigenin, 5-bromo-deoxyuridine, or fluorescein to provide probes that can be used in numerous applications.

Polynucleotides of the subject invention can also be used for the qualitative and quantitative analysis of gene expression using arrays or polynucleotides that are attached to a solid support. As used herein, the term array means a one-, two-, or multi-dimensional arrangement of full length polynucleotides or polynucleotides of sufficient length to permit specific detection of gene expression. Preferably, the fragments are at least 15 nucleotides in length. More preferably, the fragments are at least 100 nucleotides in length. More preferably, the fragments are more than 100 nucleotides in length. In some embodiments the fragments may be more than 500 nucleotides in length.

For example, quantitative analysis of gene expression may be performed with full-length polynucleotides of the subject invention, or fragments thereof, in a complementary DNA microarray as described by Schena et al. (1995, 1996a). Polynucleotides, or fragments thereof, are amplified by PCR and arrayed onto silylated microscope slides. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

mRNA is isolated from a biological sample and probes are prepared by a single round of reverse transcription. Probes are hybridized to 1 $cm^2$ microarrays under a 14×14 mm glass coverslip for 6-12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Alternatively, the polynucleotide sequences related to the invention may also be used in analytical systems, such as DNA chips. DNA chips and their uses are well known in the art (see for example, U.S. Pat. Nos. 5,561,071; 5,753,439; 6,214,545; Schena 1996b; Bianchi et al., 1997; each of which is hereby incorporated by reference in their entireties) and/or are provided by commercial vendors such as Affymetrix, Inc. (Santa Clara, Calif.).

Also within the scope of the subject instant invention are vectors or expression cassettes containing genetic constructs as set forth herein or polynucleotides encoding the polypeptides, set forth supra, operably linked to regulatory elements. The vectors and expression cassettes may contain additional transcriptional control sequences as well. The vectors and expression cassettes may further comprise selectable markers.

The expression cassette will include in the 5'-3' direction of transcription, a transcriptional and translational initiation region, a DNA sequence of the invention, and a transcriptional and translational termination regions. The transcriptional initiation region, the promoter, may be native or analogous, or foreign or heterologous, to the host cell. By "foreign" is intended that the transcriptional initiation region is not found in the organism into which the transcriptional initiation region is introduced.

The subject invention also provides for the expression of a polypeptide, peptide, fragment, or variant encoded by a polynucleotide sequence disclosed herein comprising the culture of a host cell transformed with a polynucleotide of the subject invention under conditions that allow for the expression of the polypeptide and, optionally, recovering the expressed polypeptide.

Application of B Series Microbe-Based Products

In yet another aspect, the methods and systems of the subject invention can include methods, systems, and devices for applying the microbe-based products.

As used herein, "applying" a composition or product refers to applying it to a target or site such that the composition or product can have an effect on that target or site. The effect can be due to, for example, microbial growth and/or the action of a biosurfactant or other growth by-product.

The microbial growth by-product produced by microorganisms of interest may be retained in the microorganisms or secreted into the liquid medium. In another embodiment, the method for producing microbial growth by-product may further comprise steps of concentrating and purifying the microbial growth by-product of interest. In a further embodiment, the liquid medium may contain compounds that stabilize the activity of microbial growth by-product.

In one embodiment, all of the microbial cultivation composition is removed upon the completion of the cultivation (e.g., upon, for example, achieving a desired cell density, or density of a specified metabolite in the broth). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or contain cells. In this manner, a quasi-continuous system is created.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

In the case of agriculture, the compositions may be, for example, introduced into an irrigation system, sprayed from a backpack or similar devices, applied by a land based or airborne robotic device such as a drone, and/or applied with a seed. Seed application may be by, for example, a seed coating or by applying the composition to the soil contemporaneously with the planting of seeds. This may be automated by, for example, providing a device or an irrigation system that applies the microbe-based composition along with, and/or adjacent to, seeds at, or near, the time of planting the seeds. Thus, the microbe-based composition can be applied within, for example, 5, 4, 3, 2, or 1 day before or after the time of plantings or simultaneously with planting of the seeds.

In some agricultural embodiments, the compositions provided herein, either in a dry or in liquid formulation, are applied as a seed treatment or to the soil surface, to the surface of a plant and/or to the surface of a pest or weed.

In certain embodiments, the compositions provided herein are applied to the soil surface without mechanical incorporation. The beneficial effect of the soil application can be activated by rainfall, sprinkler, flood, or drip irrigation, and subsequently delivered to, for example, targeted pests in order to drive their population levels down to acceptable thresholds or to the roots of plants to influence the root microbiome or facilitate uptake of the microbial product into the vascular system of the crop or plant to which the microbial product is applied. In an exemplary embodiment, the compositions provided herein can be efficiently applied via a center pivot irrigation system or with a spray over the seed furrow.

Reference herein to administration of the composition "on or near" a pest or a plant, or to the "environment" of a pest or plant, means that the administration is such that the composition is sufficiently in contact with the pest or plant such that the desired result (e.g., killing the pest, increasing yield, preventing damage to the plant, regulating genes and/or hormones, etc.) is achieved. This may typically be within, for example, 10, 5, 3, 2, or 1 feet or less, of the pest, plant, weed, or other desired target.

The microbe-based product may also be applied so as to promote colonization of the roots and/or rhizosphere as well as the vascular system of the plant in order to promote plant health and vitality. Thus, nutrient-fixing microbes such as rhizohium and/or mycorrhzae can be promoted as well as other endogenous (already present in the soil), as well as exogenous, microbes, or their by-products, that combat pests, weeds, or disease, or otherwise promote crop growth, health and/or yield. The microbe-based product can also support a plant's vascular system by, for example, entering and colonizing said vascular system and contributing metabolites, and nutrients important to plant health and productivity or metabolites with pest controlling properties.

Advantageously, the method does not require complicated equipment or high energy consumption. The microorganisms of interest can be cultivated at small or large scale on site and utilized, even being still mixed with their media. Similarly, the microbial metabolites can also be produced at large quantities at the site of need.

Advantageously, the microbe-based products can be produced in remote locations. In one embodiment, the microbe-based products can be used for human nutrition and/or disease prevention and/or treatment. The microbe growth facilities may operate off the grid by utilizing, for example, solar, wind and/or hydroelectric power.

The microbe-based products may be applied directly to animal waste, and/or used in a waste treatment plant. The microbe-based products can also be applied directly to environment contamination such as an oil spill or hazardous waste site. The microbe-based products can also be applied to ores in order to recover metals, minerals, or other substances of interest. The microbe-based products can also be injected into oil wells and/or the piping associated with oil wells.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

EXAMPLES

Composition of Minimal Salt Enrichment Medium for Isolating *Bacillus subtilis* B Series Strains Example 1—Enrichment Cultivation of Biosurfactant-Producing Strains Mixed samples from oil wells were inoculated (~1×10$^8$ CFU/mL) in minimal enrichment medium (see Table 4) with crude oil as the sole carbon source.

Minimal salt enrichment medium was developed and used for the enrichment and isolation of *Bacillus subtilis* B series strains obtained from Ohio oil well samples. Table 4 depicts the composition of minimal salt enrichment medium.

TABLE 4

| Stock Solution | Amount Added | Final Concentration |
|---|---|---|
| 5 X M9 salt stock solution | 10 mL | 1 X |
| dH20 | 40 mL | — |
| 1M MgSO4 | 100 µL | 2 mM |
| 1M CaCl2 | 5 µL | 0.1 mM |
| 10% yeast extract solution | 50 µL | 0.1 g/L |
| Trace elements mixture | 50 µL | 1 X |
| 25% Glucose | 20 µL | 0.1 g/L |
| Crude oil | 2.5 mL | 5% |
| Total Volume | ~50 mL | |

The samples were then cultivated aerobically at 40° C. Oil droplets in the medium were emulsified and utilized by the surfactant-producing bacteria.

These results demonstrate that the minimal enrichment medium with crude oil will support biosurfactant production by *Bacillus subtilis* B series strains.

Example 2—Colony Morphology of Different *Bacillus subtilis* B Series Strains

*Bacillus subtilis* B series strains (strains: B1, B2, and B3) were streaked on nutrient broth agar plates and cultivated at 40° C.

As seen in FIG. 1, the closely related B series strains all show different colony morphology from one another.

Figures 2A, 2B:
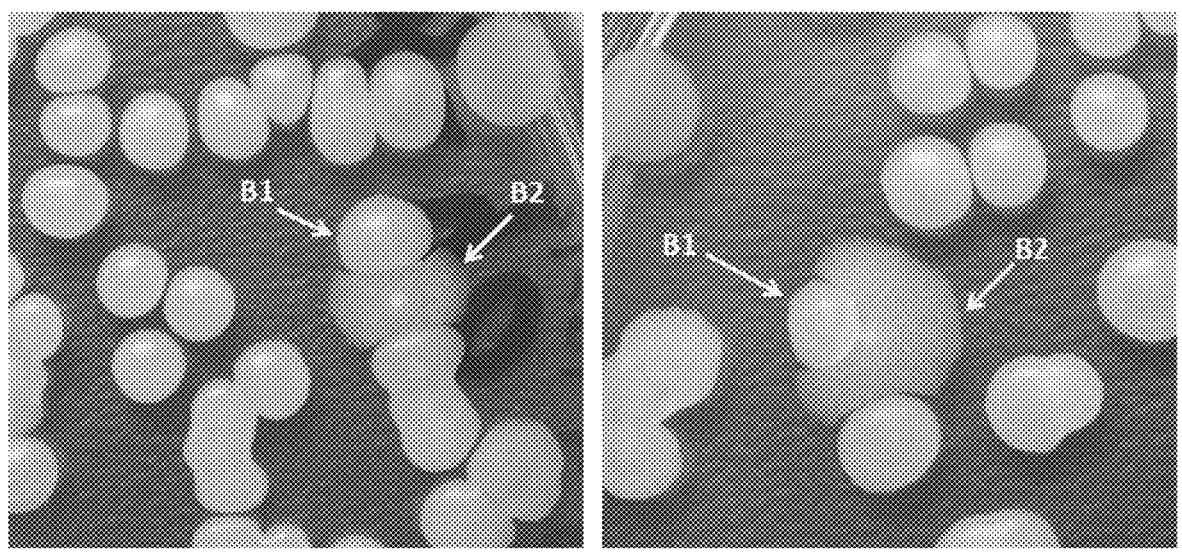
FIGS. 2A-2B show a close-up view of colony morphology of *Bacillus subtilis* strains B1 and B2.

FIGS. 2A-2B depicts a close-up view of colony morphology of strains B1 and B2. Differences in morphology and biosurfactant production between B1 and other B series strains (B2 and B3) are due to genomic sequence differences. Samples of B1 strain microbes were withdrawn at 10 hour and 48 hours of growth.

As seen in FIGS. 3A-3B, *Bacillus subtilis* cells from strain B1 are in a vegetative state, while those withdrawn at the 48 hour mark are spore-like.

Example 3—Assay of Biosurfactant Production

*Bacillus subtilis* B series strains were assayed for biosurfactant production. Strains B1, B2, B3 and a control *Bacillus* (*Bacillus mojavensis* JF-2) were inoculated and cultivated in minimal salt M9 medium at 40° C. Water (20 mL) was added in a 9 cm diameter petri dish. Sudan III dyed n-dodecane (50 uL) was added on top of the water to form a film of oil. 10 uL supernatant of fermentation broth was gently added in the middle of the oil film. Biosurfactant activity in the sample will cause oil to be repelled from the center of the plate to the edge. The diameter of the halo is proportional to concentration or total activity of biosurfactant. For the plate with B3 strain, the oil film was completely disrupted.

Biosurfactant production was tested in a new modified medium (see Table 5 below). The medium was developed by modifying the typical M9 medium. The medium has been screened for having very low background for oil spreading assay of biosurfactant activity. The medium is optimized for growth and surfactant production.

TABLE 5

| Stock Solution | Amount Added | Final Concentration |
| --- | --- | --- |
| 5 X M9 salt stock solution | 10 mL | 1 X |
| dH$_2$0 | 40 mL | — |
| 1M MgSO$_4$ | 100 µL | 2 mM |
| 1M CaCl$_2$ | 5 µL | 0.1 mM |
| 10% yeast extract solution | 500 µL | 1 g/L |
| Trace elements mixture | 50 µL | 1 X |
| 25% Glucose | 2 mL | 10 g/L |
| Total Volume | ~50 mL | |

Strains were inoculated and cultivated in modified minimal salt M9Y10 medium at 40° C. for 39 hours, aerobically. For comparison purposes, the performance of *Bacillus mojavensis* JF-2, *Bacillus subtilis* NIPER 1A and *Bacillus subtilis* NIPER 11A were also tested.

Protocol of Oil Spreading

Twenty mL of water was added in the petri dish of 9-cm diameter. 50 µL Sudan III dyed n-dodecane was added on the top of water to form a film of oil. 10 µL supernatant of the bacteria fermentation broth was gently added in the middle of the oil film. Oil will be repelled from the center to the edge of the plate if there is biosurfactant activity in the sample. Diameter of the halo is measured and it is proportional to concentration or total activity of biosurfactant.

As shown in FIG. 4, performance of B strains were found to be superior, and they have 10-12 fold higher biosurfactant activity compared to the other well-known strains.

Biosurfactant production by different *Bacillus* B series strains was also tested under aerobic and high salt conditions. Strains were inoculated and cultivated in modified minimal salt M9Y10 medium with 100 g/L NaCl at 40° C. for 30 hours, under aerobic conditions. For comparison purposes, the performance of *Bacillus mojavensis* JF-2 was also tested.

Figure 5:
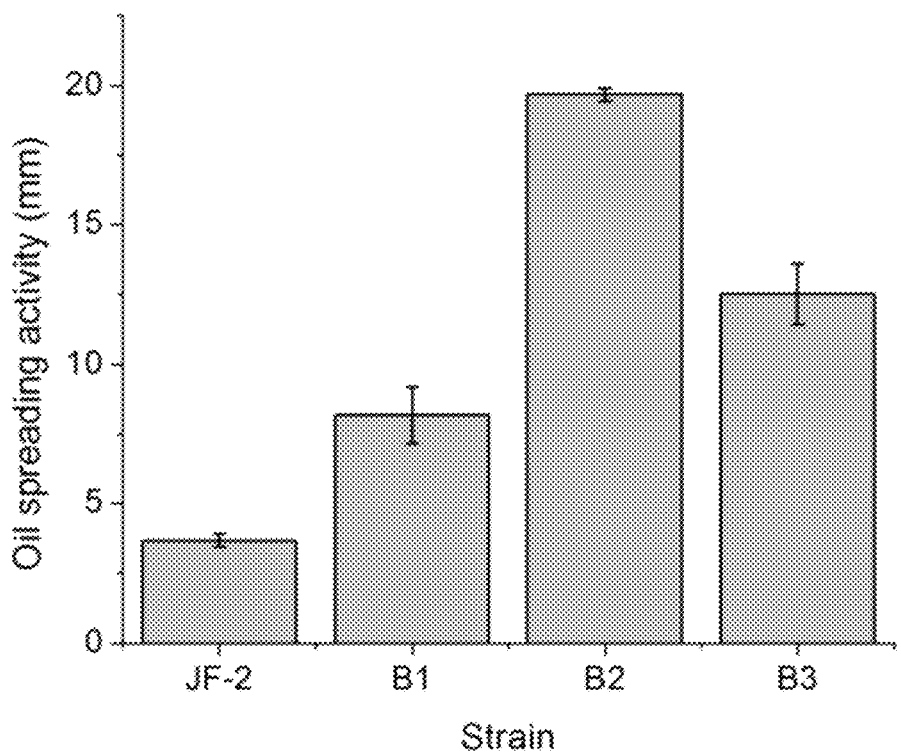
FIG. 5 shows biosurfactant activities of different bacteria strains under aerobic and high salinity conditions. Different bacterial strains were inoculated and cultivated in modified minimal salt M9Y10 medium with 100 g/L NaCl at 40° C. for 30 hours, aerobically. For comparison purpose, the performance of a typical successful *Bacillus* strain used in MEOR (*Bacillus mojavensis* JF-2) was also tested. As showed in the figure, performance of *Bacillus subtilis* B1, B2 and B3 strains are superior and they have 2-5 fold higher biosurfactant activity than the well-known strain JF-2.

As shown in FIG. 5, the performance of B strains was superior with 2-5 fold higher biosurfactant activity compared to strain JF-2.

Example 4—Anaerobic Growth of *Bacillus subtilis* B Series Strains

Oil wells and other sites of oil recovery have low oxygen conditions. The ability of *Bacillus subtilis* B series strains to grow under anaerobic/low oxygen conditions was tested.

Strain B1 was inoculated and cultivated in nutrient broth (NB) medium with NaNO$_3$ 5 g/L, in a NBS BioFlo 115 bench top fermentor. Medium was flushed with N$_2$ to maintain anaerobic conditions. Growth was monitored by using a BugLab biomass monitoring device and the growth curve was plotted in the Bug Units. Evidence of the production of active biosurfactant by strain B1 was demonstrated by the build-up of foam in the tank.

B strains of the present invention were next tested for biosurfactant production under anaerobic conditions.

Strains were inoculated and cultivated in modified minimal salt M9Y10 medium at 40° C. in sealed serum bottles. Oxygen is depleted quickly within 30 minutes after inoculation and the growth turns into anaerobic conditions. For comparison purposes, the performance of *Bacillus mojavensis* JF-2 was also tested.

Figure 6:
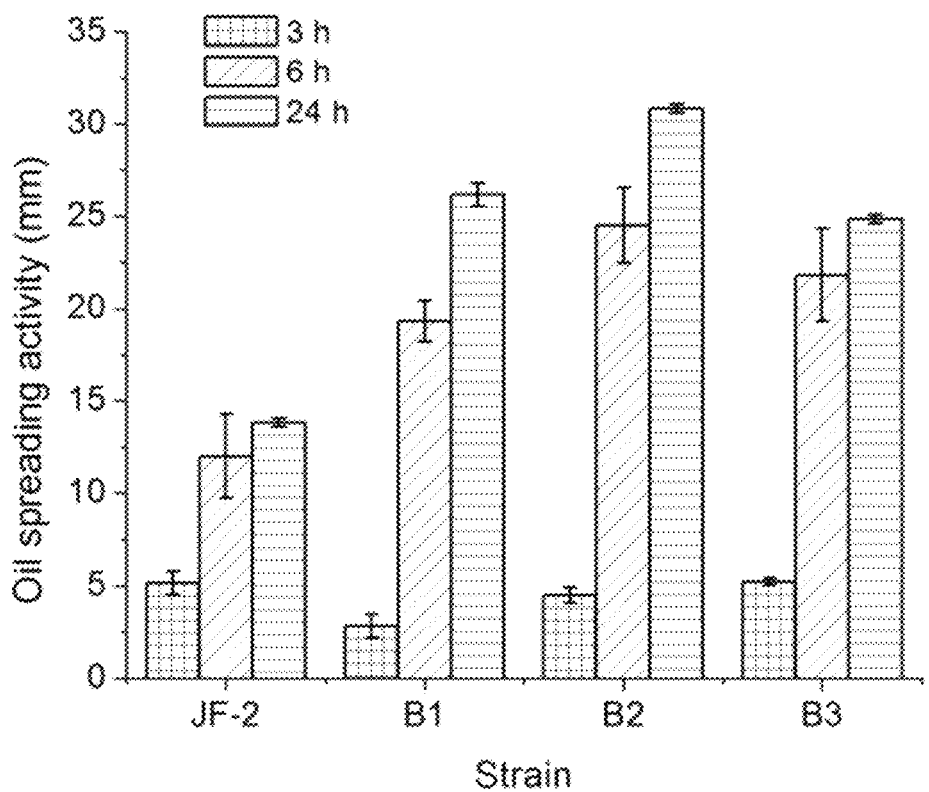
FIG. 6 shows biosurfactant activity of different bacteria strains under anaerobic fermentation condition. Different bacteria strains were inoculated and cultivated in modified minimal salt M9Y10 medium at 40° C. in sealed serum bottles. Oxygen was depleted quickly within 30 min after inoculation and the growth turned into anaerobic condition. For comparison purpose, the performance of typical successful *Bacillus* strain used in MEOR (*Bacillus mojavensis* JF-2) were also tested. As showed in the figure, performance of *Bacillus subtilis* B1, B2 and B3 strains are superior and B2 has at least 2 fold higher biosurfactant activities than the well-known strain JF-2.

As shown in FIG. 6, the performance of B strains was superior, and strain B2 was found to have at least 2 fold higher biosurfactant activity compared to the strain JF-2.

Example 5—Salt Tolerance of *Bacillus subtilis* B Series Strains

Due to the very salty brine-like environment of oil sites, the salt tolerance of different B series strains was tested. Strains were inoculated and cultivated in modified minimal salt M9Y10 medium with NaCl 100 g/L at 40° C. in flask. OD 600 nm was measured for monitoring the growth.

Figure 7:
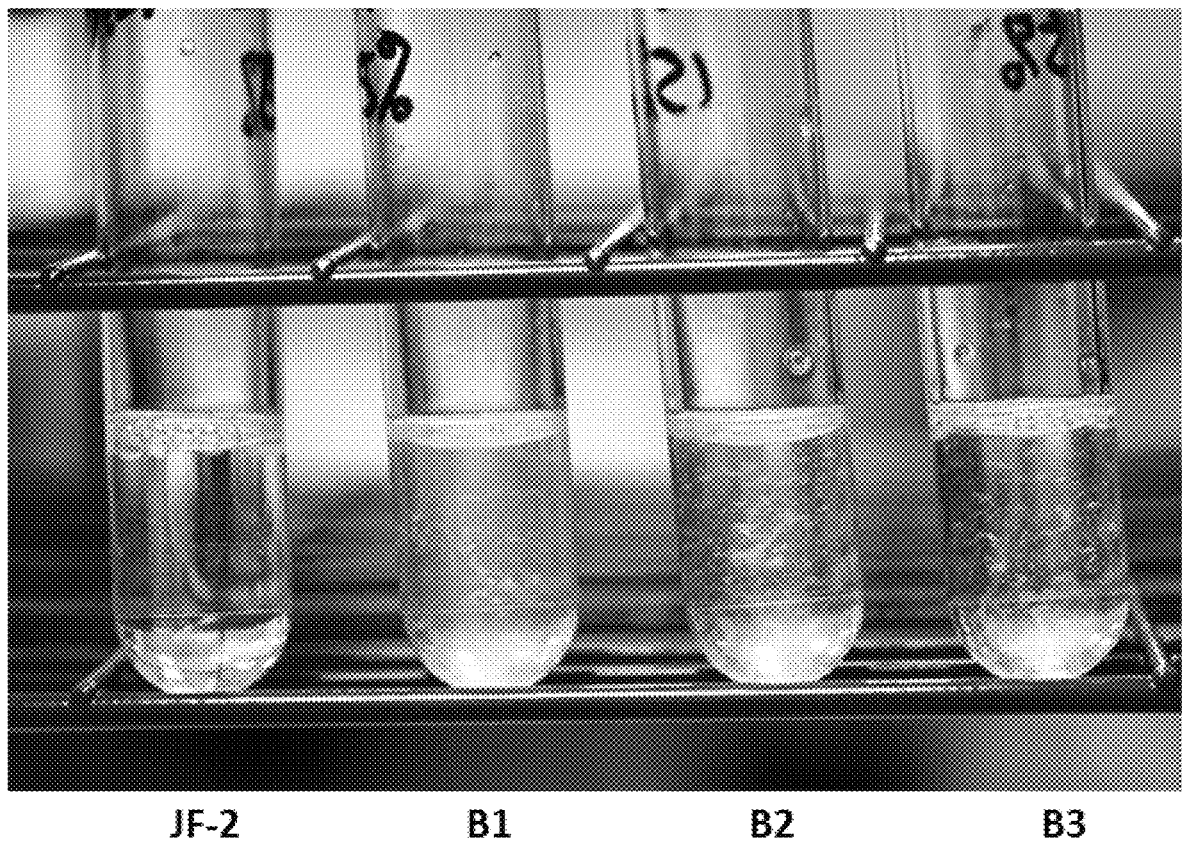
FIG. 7 shows growth of different strains under high salinity condition. Different bacteria strains were inoculated and cultivated in modified minimal salt M9Y10 medium with 150 g/L NaCl at 40° C. in test tube. No growth was observed for JF-2. All *Bacillus subtilis* B1, B2 and B3 strains grew well as showed by the turbidity of the medium.

B strains appeared to have comparable salt tolerance (for NaCl 10%) with JF-2. Then much higher salt conditions were also tested (see FIG. 7). Strains were inoculated and cultivated in modified minimal salt M9Y10 medium with NaCl 150 g/L at 40° C. in test tube. Under these conditions, no growth was observed for JF-2. All B strains grew under conditions of NaCl 150 g/L (15% NaCl) as shown by the turbidity of the medium. These data indicate the superior salt-tolerant of *Bacillus subtilis*-B strains.

Example 6—Drop Shape and Wettability Analyses of *Bacillus subtilis* B Series Strains One way to assess surfactant activity is through drop shape analysis. Samples of culture supernatants were stained with crystal violet. A 10 µL sample was dropped on hydrophobic surface of the petri dish plate. Samples with a higher concentration of biosurfactant or higher biosurfactant activity will have much lower surface tension and will not be able to maintain a perfect sphere shape.

Supernatants of B strains were superior on decreasing surface tension compared to samples from all other strains. Water and medium were used as negative control.

Another way to assess surfactant activity is through the wettability assay. Wettability is the key factor for biosurfactant working on MEOR applications. Crude oil that sticks on a rock or rocky surface is difficult to recover; however, placement of surfactant on that surface will increase wettability and the crude oil can be recovered.

A tilted glass slide test was used for measure the wettability of biosurfactants produced from different fermentation samples. For comparison purposes, the performance samples from *Bacillus mojavensis* JF-2, *Bacillus subtilis* NIPER 1A and *Bacillus subtilis* NIPER 11A were also tested.

The performance of B series strains was superior to the other well-known *Bacillus* strains. For the test procedure, samples were dropped on the hydrophobic surface and the plate was tilted. Lower surface tension gives more wettability and faster flow on the hydrophobic surface.

Example 7—Test of Emulsification of Crude Oil in Brine by *Bacillus subtilis* B Series Strains The ability of the *Bacillus subtilis* B series strains to emulsify crude oil in brine was also tested. 2.5 mL supernatant of cell culture was mixed with 2.5 mL brine from oil well, then 5.0 mL crude oil from oil well was added and vortexed vigorously for 1 minute and allowed to sit still for 15 minutes at room temperature. Supernatants from *Pseudomonas* and *Bacillus mojavensis* JF-2 were also tested along with water as a control.

Figure 8:
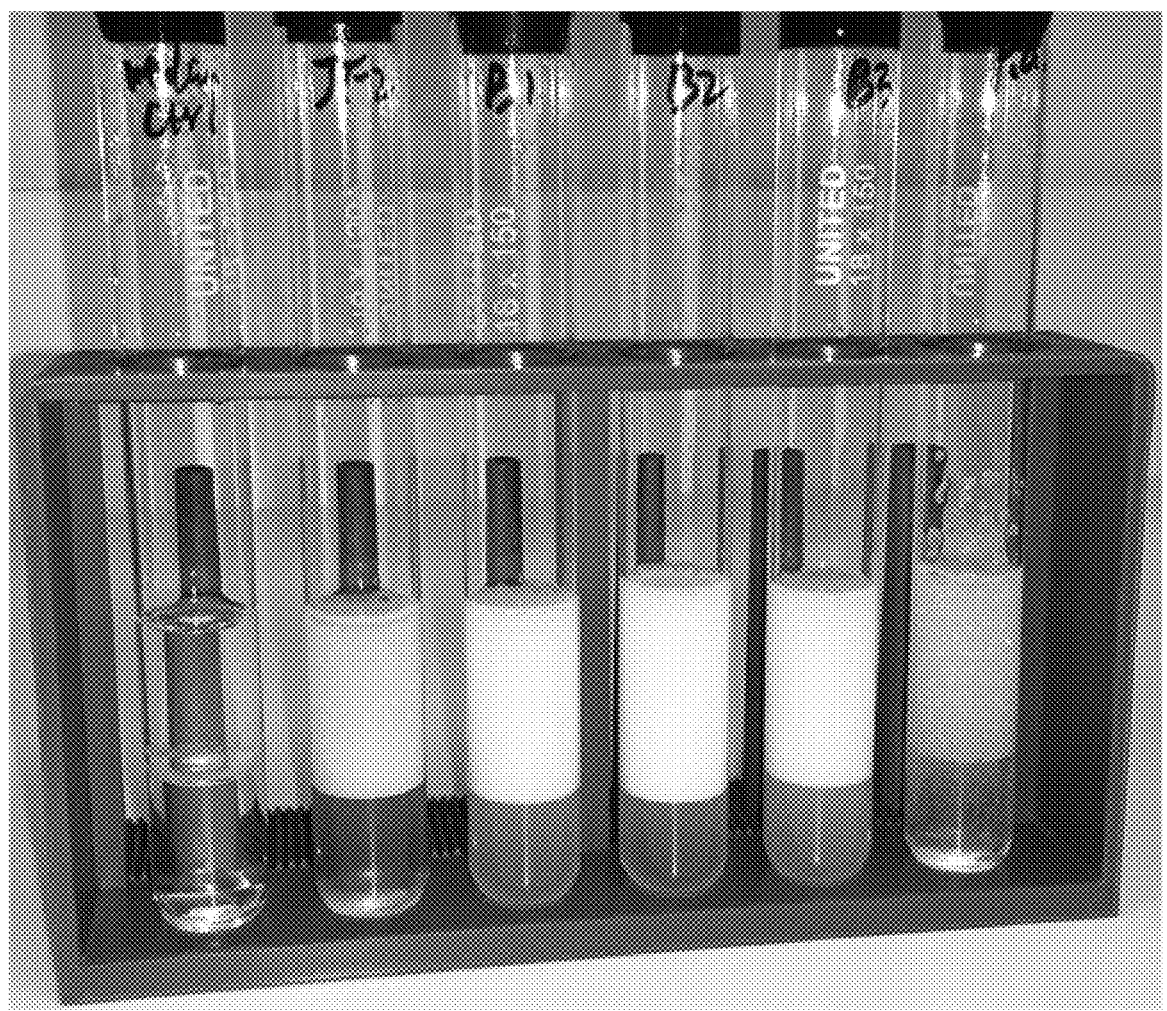
FIG. 8 shows emulsification of n-hexadecane in water by the culture supernatants from different strains. 2.5 mL supernatant of cell culture was mixed with 2.5 mL water, then 5.0 mL n-hexadecane was added and vortexed vigorously for 1 min and sit still for 15 min at room temperature. Supernatants from all *Bacillus subtilis* B1, B2 and B3 strains made more stable and finer emulsions. Test tubes from left to right: control, *Bacillus mojavensis* JF-2, *Bacillus subtilis* B1, *Bacillus subtilis* B2, *Bacillus subtilis* B3, *Pseudomonas aeruginosa* ATCC 9027.

As shown in FIG. 8, supernatants from all B strains made more stable and finer emulsions than the other test strains. B1 and B3 made majorly water-in-oil emulsions and B2 made majorly oil-in-water emulsions.

The ability of the *Bacillus subtilis* B series strains to emulsify crude oil in brine under different temperatures was also tested. 2.5 mL supernatant of cell culture was mixed with 2.5 mL brine from oil well, then 5.0 mL crude oil from oil well was added and vortexed vigorously for 1 minute and allowed to sit still for 60 minutes at 45° C. or 55° C. Supernatants from *Pseudomonas* and *Bacillus mojavensis* JF-2 were also tested along with water as a control.

Supernatants from all B strains made more stable and finer emulsions. B1 and B3 made majorly water-in-oil emulsions and B2 made majorly oil-in-water emulsions.

Example 8—Optimization of Media Components for Growth of *Bacillus subtilis* B Series Strains Different carbon sources were tested to find a preferred carbon source. The goal was to optimize growth while minimizing cost. Carbon sources such as glucose, baker sugar, and molasses were used with minimal salt to culture B1.

Optimum growth for B1 was observed with molasses as a carbon source.

In a similar manner, different nitrogen sources were tested to find the optimum nitrogen source for growth of B1. Corn peptone was the optimum nitrogen source for *Bacillus subtilis* strain B1.

As molasses and corn peptone appeared to be the optimum carbon and nitrogen sources for B1 growth, different concentrations of molasses and corn peptone were tested to determine the optimum concentration.

Figure 9A:
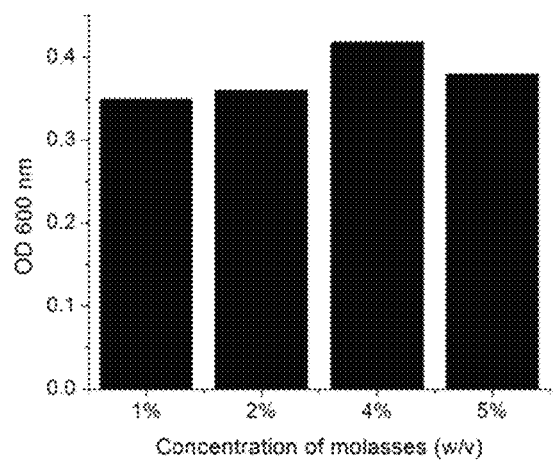
FIGS. 9A-9B show optimization of concentration of molasses and corn peptone for optimal growth of *Bacillus subtilis* B1. Different concentration of molasses (FIG. 9A) and corn peptone (FIG. 9B) as showed in the figure was used to find out the optimum concentration. As shown in the figure 4% molasses and 0.4% corn peptone was found to be optimum concentration for growth of *Bacillus subtilis* B1.
Figure 9B:
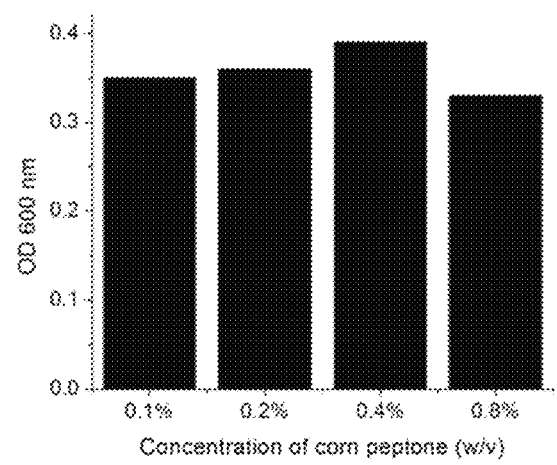

As shown in FIG. 9A, 4% molasses concentration was optimum for B1 growth while 0.4% corn peptone concentration was found to be optimum for B1 growth according to FIG. 9B.

Example 9—Fermentation Using *Bacillus subtilis* B Series Strains

Based on the nutrient optimization studies, SMCP medium was developed with molasses and corn peptone as carbon and nitrogen sources. Table 6 below lists the composition of the SMCP medium for fermentation.

TABLE 6

| Composition | Stock solution | SMCP (1000 mL) | Unit | Final Concentration |
|---|---|---|---|---|
| $Na_2HPO_4—7H_2O$ | Powder | 12.8 | g | 1.28% (w/v) |
| $KH_2PO_4$ | Powder | 3 | g | 0.3% (w/v) |
| NaCl | Powder | 0.5 | g | 0.05% (w/v) |
| $NH_4Cl$ | Powder | 1 | g | 0.1% (w/v) |
| $MgSO_4$ | 1M | 2 | mL | 2 mM |
| $CaCl_2$ | 1M | 0.1 | mL | 0.1 mM |
| Trace Metal Mix | 1000 x | 1 | mL | 1 X |
| Molasses | 50% (v/v) | 80 | mL | 4% (v/v) |
| Corn Peptone | Powder | 2 | g | 0.2% (w/v) |

*Bacillus subtilis* B1 and B2 strains, respectively, were inoculated in SMCP media and cultivated to monitor fermentation under the new medium. The strains were grown in a bench top fermentor. Fermentation under conditions of changing temperature, pH, agitation were monitored. The same fermentation parameters for B1 strain were used for the B2 strain.

The fermentation of the B1 strain was analyzed for sugar utilization and possible metabolites. Strain B1 was inoculated and cultivated in SMCP medium and cultivated in 5-L NBS BioFlo 115 bench top fermentor, at 40° C., DO 30% and pH 7.0 under aerobic conditions.

Figure 10A:
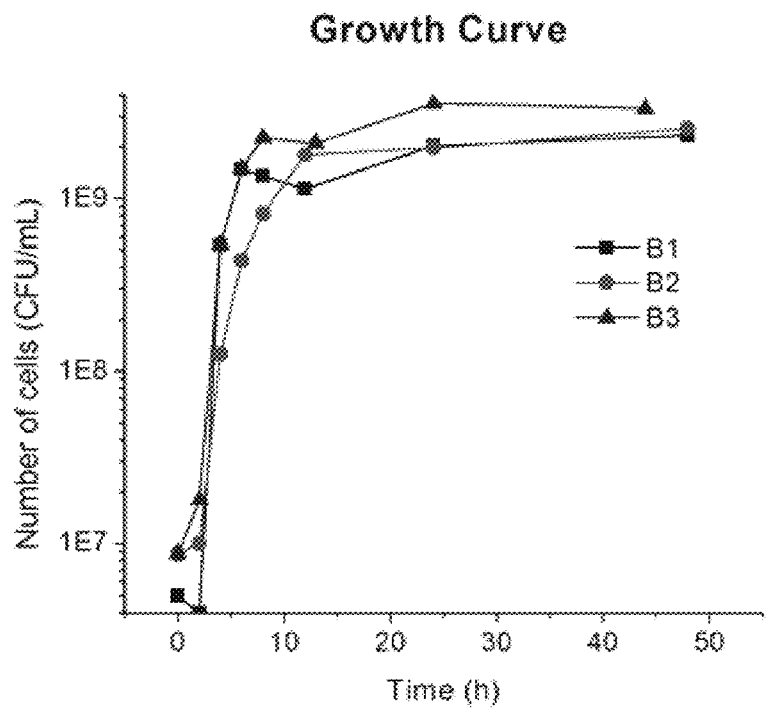
FIGS. 10A-10B show growth profiles of growth FIG. 10A and surfactin FIG. 10B production by *Bacillus subtilis* B1, B2 and B3 strains in optimized SMCP medium.
Figure 10B:
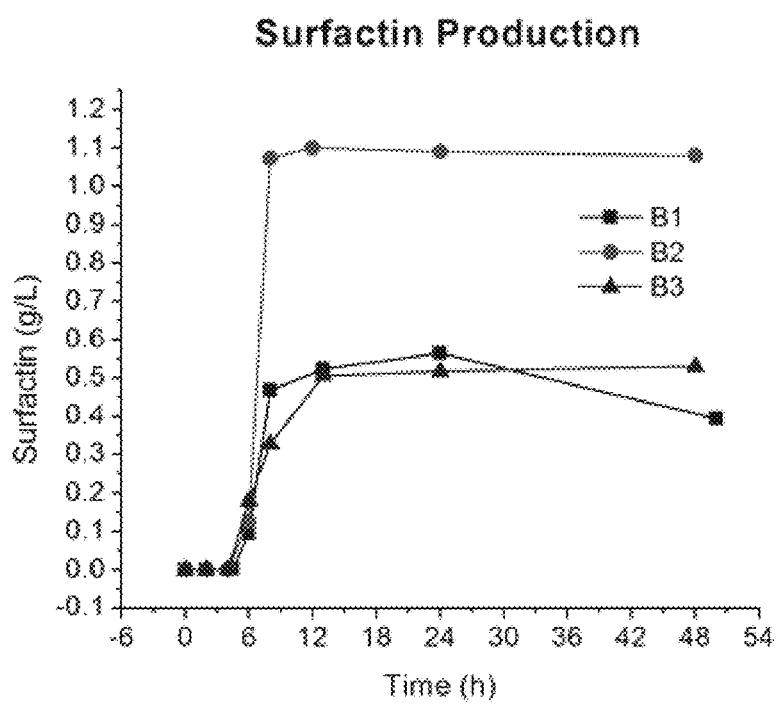

Profiles of growth (FIG. 10A) and surfactin (FIG. 10B) production by *Bacillus subtilis* B1, B2 and B3 strains in optimized SMCP medium are shown in FIGS. 10A-10B.

Example 10—Surfactin Produced by *Bacillus subtilis* B1

Figure 11A:
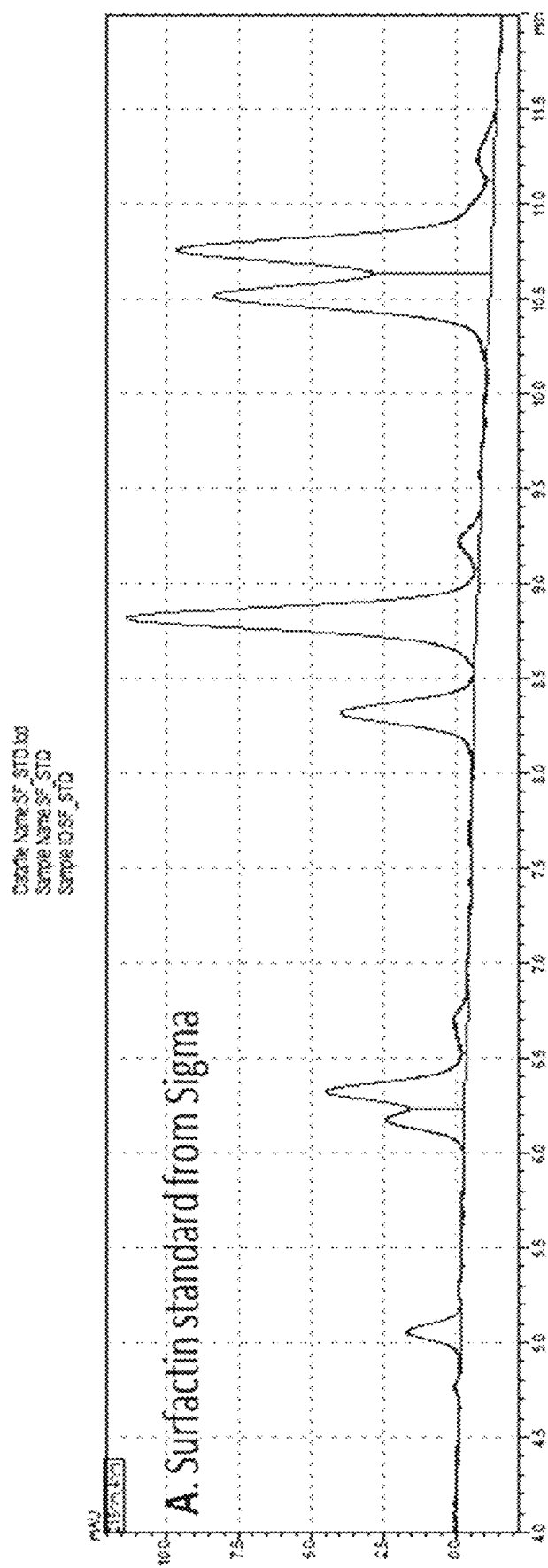
FIGS. 11A-11B show surfactin produced by *Bacillus subtilis* B1. *Bacillus subtilis* B1 was cultivated in M8 medium for 24 h and the surfactin produced was extracted by methanol and analyzed by HPLC with Kinetex 2.6 µm EVO C18 LC column 150×4.6 mm. Panel A shows the HPLC profile of the surfactin standard from Sigma and panel B shows the HPLC profile of the surfactin produced by *Bacillus subtilis* B1. Red arrows depict six different isomers of surfactin, the retention time for different isomers are 6.177 min, 6.324 min, 8.315 min, 8.818 min, 10.516 min and 10.753 min.
Figure 11B:
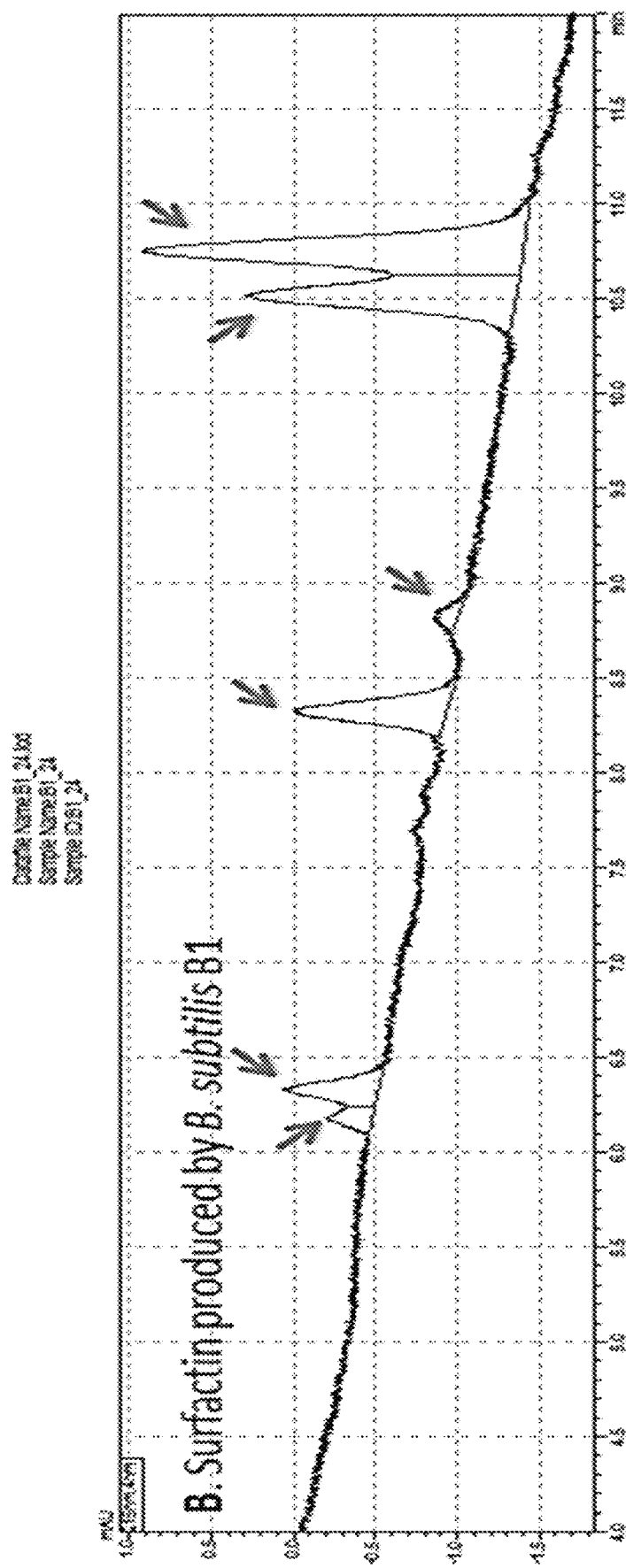

*Bacillus subtilis* B1 was cultivated in M8 medium for 24 h and the surfactin produced was extracted by methanol and analyzed by HPLC with Kinetex 2.6 μm EVO C18 LC column 150×4.6 mm. The results are shown in FIGS. 11A-11B.

Panel A shows the HPLC profile of the surfactin standard from Sigma and panel B shows the HPLC profile of the surfactin produced by *Bacillus subtilis* B1. Red arrows depict six different isomers of surfactin, the retention time for different isomers are 6.177 min, 6.324 min, 8.315 min, 8.818 min, 10.516 min and 10.753 min.

Example 11—Metabolite Analysis of *Bacillus subtilis* B1 Under Aerobic and Anaerobic Growth Conditions

Figure 12A:
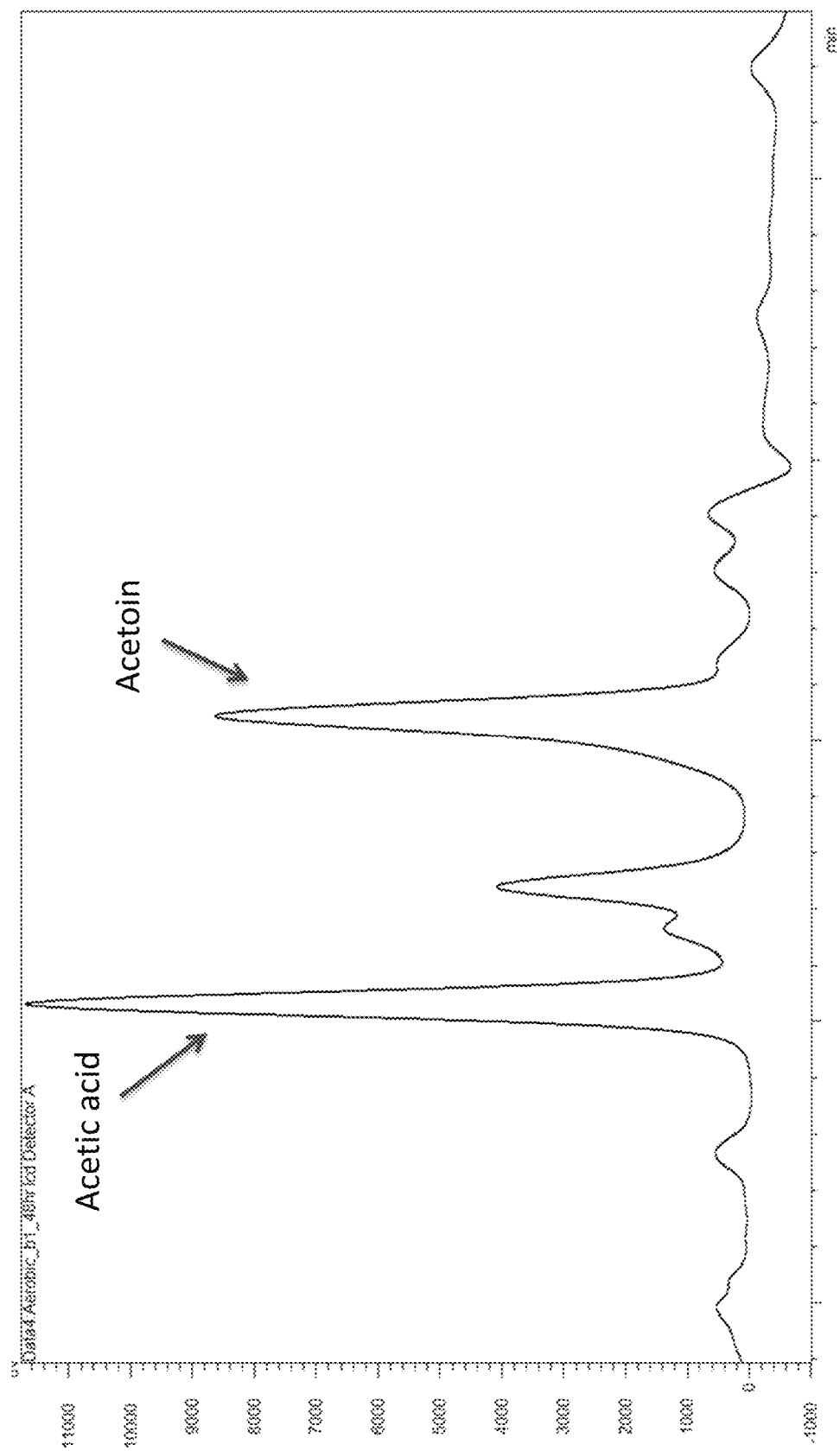
FIGS. 12A-12C show metabolite analysis of *Bacillus subtilis* B1 under aerobic and anaerobic growth conditions. *Bacillus subtilis* B1 was cultivated in M8 medium for 48 hours under different conditions: (12A) aerobic condition; (12B) anaerobic condition; (12C) anaerobic condition with 5 g/L NaNO$_3$. Red arrows depict identified metabolites. Under aerobic conditions, the major metabolites are acetic acid and acetoin. Under anaerobic conditions, major metabolites are lactic acid and trace amount of acetic acid. Under anaerobic conditions with 5 g/L NaNO$_3$ supplemented, major metabolites are lactic acid, acetic acid, acetoin and butanediol.
Figure 12B:
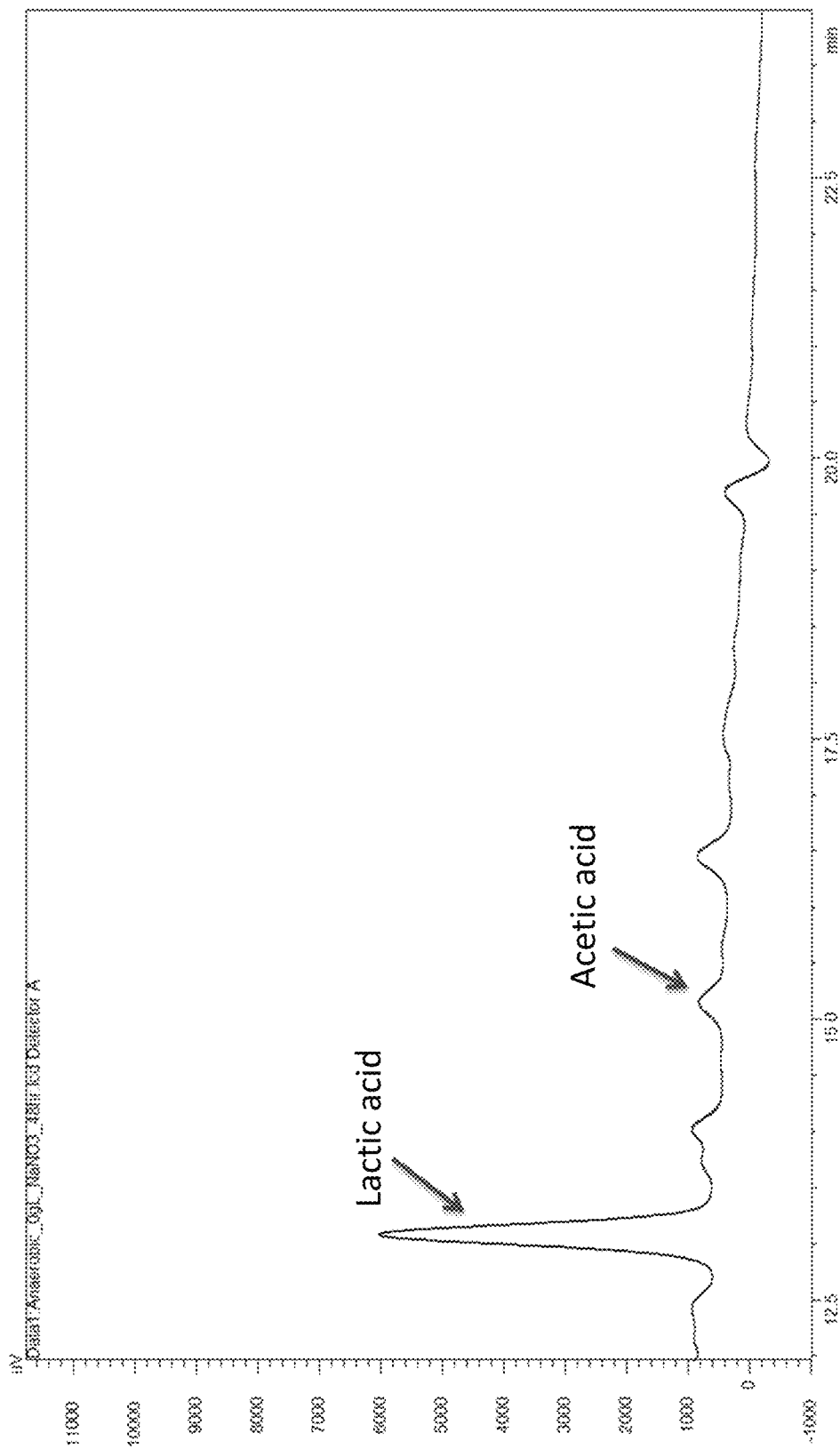
Figure 12C:
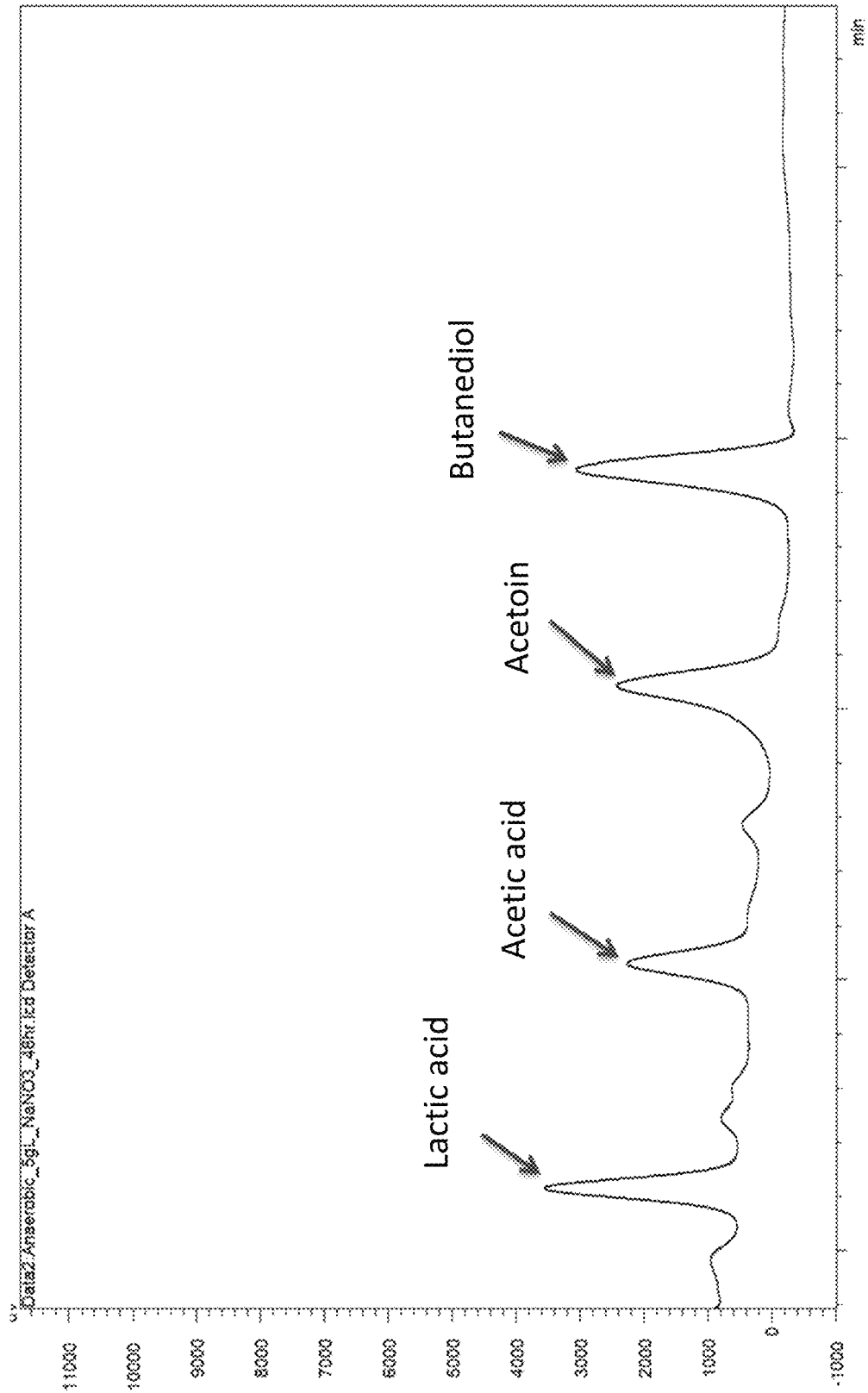

*Bacillus subtilis* B1 was cultivated in M8 medium for 48 hours under different conditions: (A) aerobic condition; (B) anaerobic condition; (C) anaerobic condition with 5 g/L $NaNO_3$. The results are shown in FIGS. 12A-12C.

Red arrows depict identified metabolites. Under aerobic conditions, the major metabolites are acetic acid and acetoin. Under anaerobic conditions, major metabolites are lactic acid and trace amount of acetic acid. Under anaerobic conditions with 5 g/L $NaNO_3$ supplemented, major metabolites are lactic acid, acetic acid, acetoin and butanediol.

Example 12—Treatment by *Bacillus subtilis* B1 for Increasing Oil Mobility and Elimination of Paraffin Obstruction in Oil Wells and Oil Production Infrastructure In the course of treating wells with the *Bacillus subtilis* B1 organism to increase mobility, three wells were encountered that had significant paraffin obstruction issues with solidified paraffin that ranged from 4-8 inches in thickness in the well bore, in addition to low oil mobility issues.

Figures 13A, 13B:
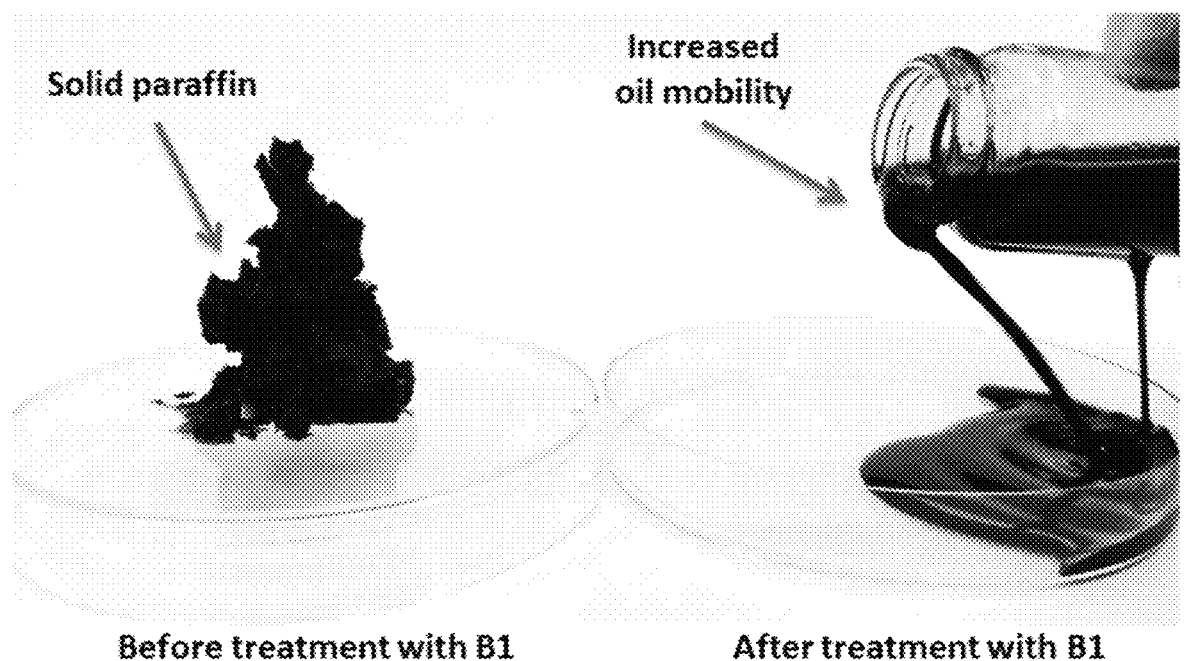
FIGS. 13A-13B show treatment by *Bacillus subtilis* B1 for increasing oil mobility and elimination of paraffin obstruction in oil wells and oil production infrastructure. In the course of treating wells with the *Bacillus subtilis* B1 organism to increase mobility, three wells were encountered that had significant paraffin obstruction issues with solidified paraffin that ranged from 4-8 inches in thickness in the well bore, in addition to low oil mobility issues. After the treatment of B1 and nutrients and a one-week shut-in period, not only was oil mobility increased but also the paraffin in the well-bore was completely eliminated and the oil was free-flowing. No paraffin obstruction was observed after treatment.

After the treatment of B1 and nutrients and a one-week shut-in period, not only was oil mobility increased but also the paraffin in the well-bore was completely eliminated and the oil was free-flowing. No paraffin obstruction was observed after treatment. Results are shown in FIG. 13.

Figure 14:
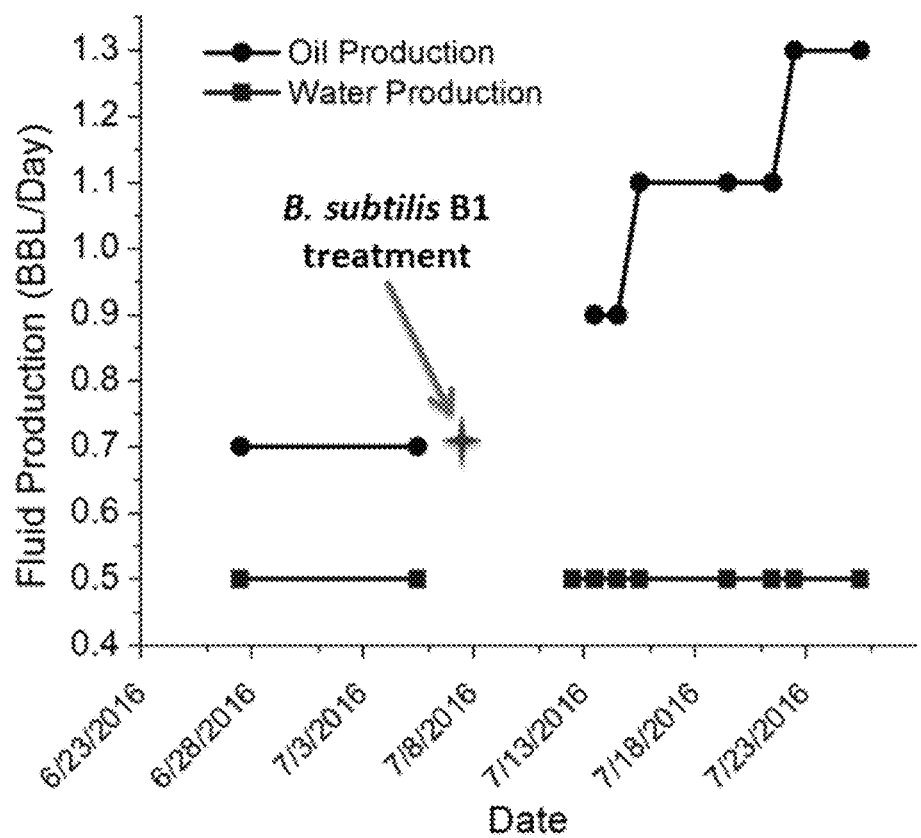
FIG. 14 Treatment of oil well A 112 by *Bacillus subtilis* B1 and the fluid production profiles. This oil well was treated with *Bacillus subtilis* B1 cell culture with cell count at $1.42 \times 10^9$ CFU/mL and surfactin concentration of 1.08 g/L, plus a nutrient mix and chasing water. After the treatment, the oil production increased from 0.7 barrel per day to 1.3 barrel per day and there is no change on water production.

Example 13—Treatment of Oil Well a #2 by *Bacillus subtilis* B1 and the Fluid Production Profiles This oil well was treated with *Bacillus subtilis* B1 cell culture with cell count at $1.42 \times 10^9$ CFU/mL and surfactin concentration of 1.08 g/L, plus a nutrient mix and chasing water. After the treatment, the oil production increased from 0.7 barrel per day to 1.3 barrel per day and there is no change on water production. Results are shown in FIG. 14.

Figure 15:
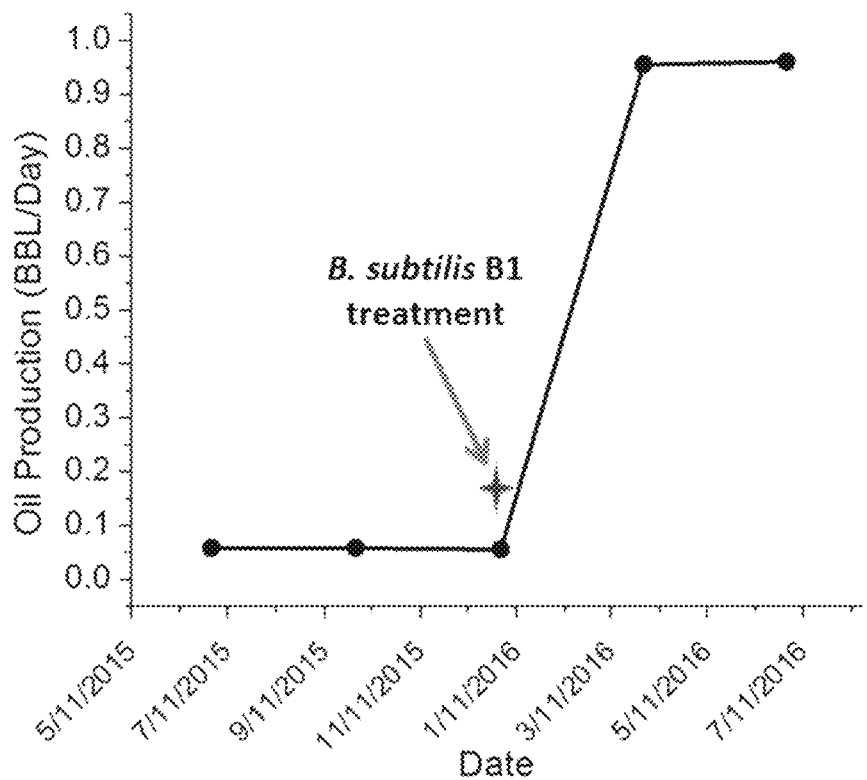
FIG. 15 Treatment of oil well B #3 by *Bacillus subtilis* B1 and the fluid production profiles. This oil well was treated with *Bacillus subtilis* B1 cell culture, plus a nutrient mix and chasing water. After the treatment, the oil production increased from 0.06 barrel per day to 0.96 barrel per day.

Example 14—Treatment of Oil Well B #3 by *Bacillus subtilis* B1 and the Fluid Production Profiles This oil well was treated with *Bacillus subtilis* B1 cell culture, plus a nutrient mix and chasing water. After the treatment, the oil production increased from 0.06 barrel per day to 0.96 barrel per day. Results are shown in FIG. 15.

Figure 16:
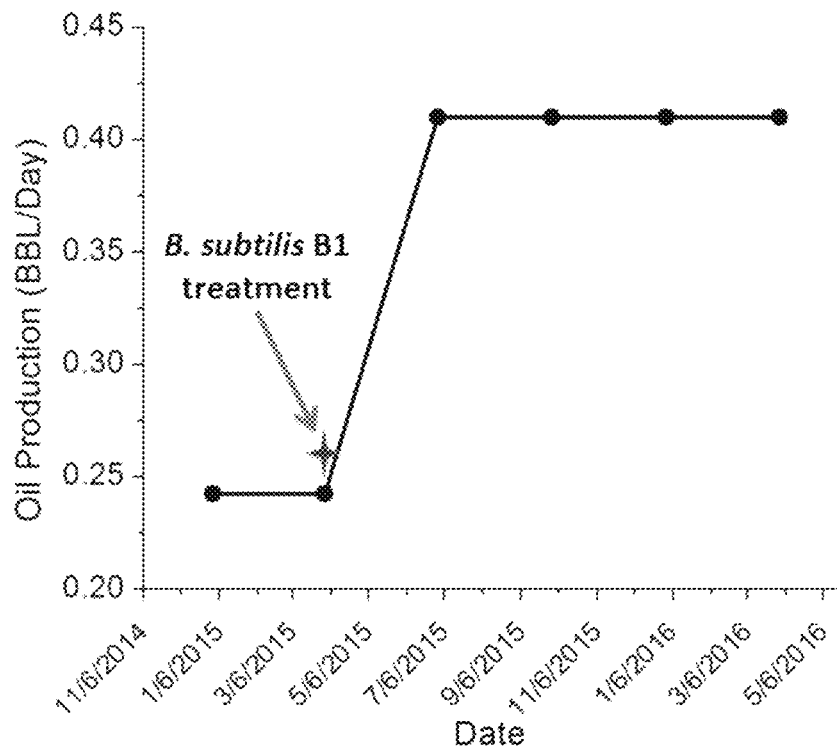
FIG. 16 Treatment of oil well C #1 by *Bacillus subtilis* B1 and the fluid production profiles. This oil well was treated with *Bacillus subtilis* B1 cell culture, plus a nutrient mix and chasing water. After the treatment, the oil production increased from 0.24 barrel per day to 0.41 barrel per day.

Example 15—Treatment of Oil Well C #1 by *Bacillus subtilis* B1 and the Fluid Production Profiles This oil well was treated with *Bacillus subtilis* B1 cell culture, plus a nutrient mix and chasing water. After the treatment, the oil production increased from 0.24 barrel per day to 0.41 barrel per day. Results are shown in FIG. 16.

Figure 17:
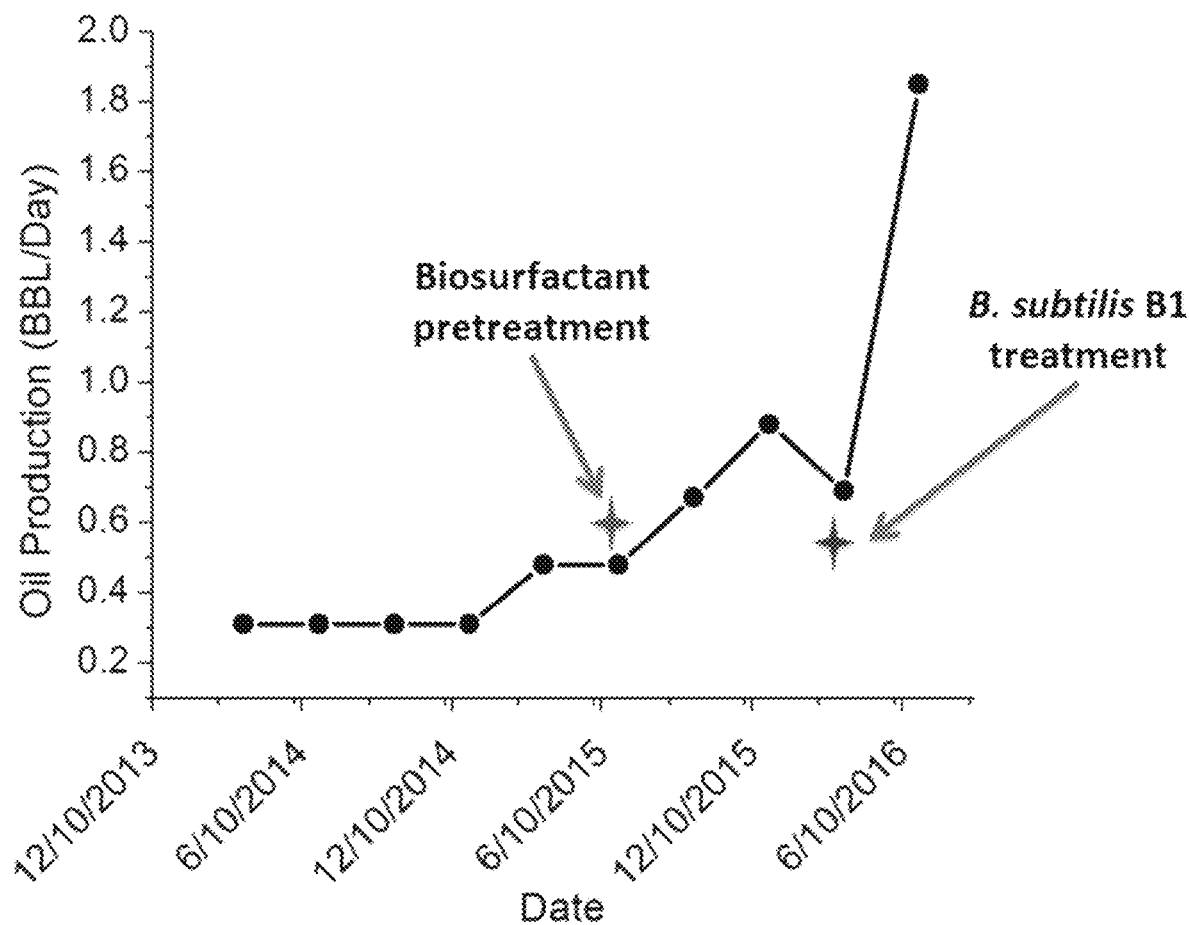
FIG. 17 Treatment of oil well D #1 by *Bacillus subtilis* B1 and the fluid production profiles. This oil well was treated with *Bacillus subtilis* B1 cell culture, plus a nutrient mix and chasing water. After the treatment, the oil production increased from 0.69 barrel per day to 1.85 barrel per day.
Figure 18:
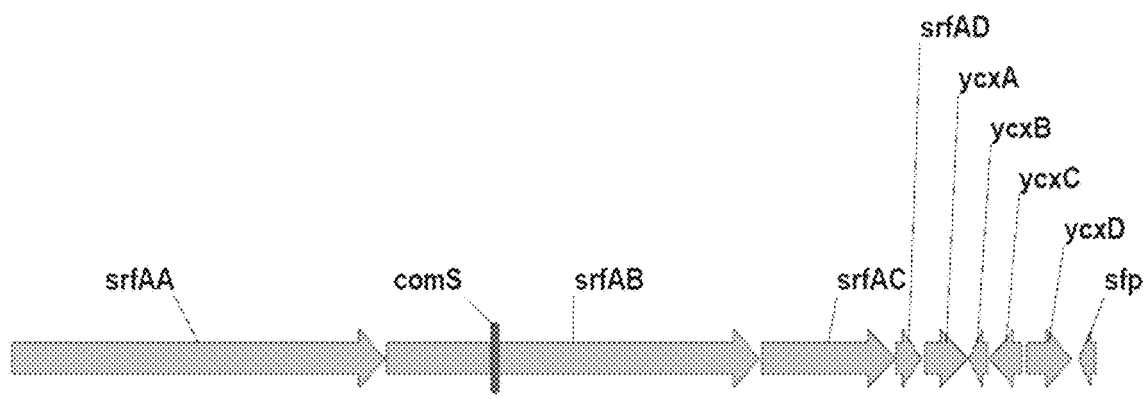
FIG. 18 shows a visual representation of the srfA operon, which is responsible for biosurfactant biosynthesis in *Bacillus subtilis* B1, B2 and B3 strains. The operon, which is identical in all three strains, includes genes srfAA, srfAB, srfAC, srfAD and sfp.

Example 16—Treatment of Oil Well D #1 by *Bacillus subtilis* B1 and the Fluid Production Profiles This oil well was treated with *Bacillus subtilis* B1 cell culture, plus a nutrient mix and chasing water. After the treatment, the oil production increased from 0.69 barrel per day to 1.85 barrel per day. Results are shown in FIG. 17.

Example 17—Primers for Unique Signature Sequences

Table 7 below depicts thirteen (13) pairs of primers specifically designed for the *Bacillus subtilis* B1, B2, and B3 strains. All 13 primers generate unique PCR amplicons for identifying the *Bacillus subtilis* strains of the present invention. The subsequent PCR products are unique and are not found performing a search (i.e., BLAST search) in a database such as the GenBank database.

In an analysis of the B1, B2 and B3 *Bacillus* strains of the present invention, thirteen different mutations were found in the B3 strain while two additional mutations (for fifteen (15) total mutations) were found in the B2 *Bacillus subtilis* strain.

TABLE 7

Primers for Unique Signature Sequences

| SEQ ID NO | Primer Name | Primer Sequence | PCR Product | Size (bp) |
|---|---|---|---|---|
| 1 | LSBS1-F | GGACACAGATCATTGGGAGTT | GGACACAGATCATTGGGAGTTAATCTTGAATAACAGAATAATTTCTATAAATCGAAACTTTGGTTATGCAATGTTTTACTATTATAAAGGCATTCCAGATGATGAATGGTTTATATCACC | 769 |
| 2 | LSBS1-R | TGACGAGAGCCTTTATGGATTAC | TGGGAAAGAAGGTCAGTCAGTTGAATTTTTTCCTCACTTTGATGATCAACACACAAGTAATCACTTTAACTTTAAATACTTTGTAGATATTTTCTTTTTGAAAGCATACACAGTCTATGAAACAATTGGACATTTATTATACAAATTGTATGACTTGGAAATCAATGAGGACGATCCTAGAGACCAAGTAAGTTTCAAAAGTGCCATTTTTAAATTAAAGCCCGAAAATCATCGACTCTATAAAGACCTTTGCAAATTAAAACGCTCTGATGATTTTAAAAAAGGGGTAGCTATGAGAAATGATATTGCACATAATCACCCACCTTACGATATAGATTCCGGGGTAACAAAATCGAAAGGTGGGATAATCACAATGGGAATTGGCAATTATACAACCTCAAAAGAAATAAAAGAAACAATGATCGGCTTCCTTAGAAGTATTAAGGTCACTTTTGAAATGCTTGAAAAACATCTGCCCTTAAGTTGATTTTCCAAAATAGAAAGGTAATCCACTTAGCTGTTTTGATTTCATATCAATATCACCATGCTCTCTCTTAAATATGAAATAAGAAACAAGGCCACTCTTAATGAGTAGCCTTTTTCTTTACTTGATAAAGTTTTCTTTGGTAATCCATAAAGGCTCTCGTCA(SEQ ID NO: 30) | |
| 3 | LSBS2-F | TCAATTCCTCTGCACCACTTAT | TCAATTCCTCTGCACCACTTATTGCATCAAAAGTTAACGATAACAGATTGCCTTTCCTTGTTAGATTTTATGGTACGCCAACCCCTCTGTTATGTGTTGACGGAAACAAACGATTAAAAG | 906 |
| 4 | LSBS2-R | GAAGAAGTTAGCTGGGTTGTTTG | CAAAAACAGAAATTGAAAAATCGGATGCAATTGTTGCTTATTTATTTGATGAAAATTATCTCGACAAGATGTTTTTTGATAAGGTTGATCAGCTTTTCTATTCACTTCATTGCGAAACTGAAGACATGCACAGAGCCATGAGCATGGGGTTTTCATCTGAACAAATTTTCAACTTAACTTTAATGAGTAGGTATAAATATGTTTAACTGGTCTAATGACCAGTTTTTTTATAAAATACAGATTTCATTTAGAATATATCCAGCGCTCCATCACTATAAGGACATTTGCCACTACCCTCTTCGCATGTACATATATATTTCACCTCCTATTACAGTACAAGGCATAATACACATCTTACACACACTTTTCTTCTAAGCATTTAATATCTTTTTCAACTACGGAAAGAATTGCTTCGACGTGCTCTATTCTTCTATTTGCCGACATACATTTTTTCGCCGCGTTCGCTATTTCGATAACTAATCCATTTGGCGTAATTACACTCTGATAGCCATTTTGTGAAGTAGTAGCGTAAAACTTTCTCGATACCTTCTTCGCCACTTCTAAGGCTTCGTCATGCTTTTCTTTAAAATAATCTCGCCTTTTTTGCAATCTCACATACTCGTCGGTTTTTCCCGCTTCGACAATGCTTAAAGGAATATTCATTTACATAACTCCTTTAATTTTTCGATTTCCTCGTTTGCAAAGTAACGCCACTCTGGCAAAGTTTCATCCATTAGCGTTATGTTTAAAGCAAGTGATTGCACAAACAACCCAGCTAACTTCTTC (SEQ ID NO: 31) | |
| 5 | LSBS3-F | CGGAGTTTGTTAGCGAAGTTATTG | CGGAGTTTGTTAGCGAAGTTATTGAGTGTAAAACTGAAAGATTAACAGATTCCATCGAAGCTAGGTACTGTTTATCGATAAAATTAAACAACTCTTTAGACTCCTCTTTTGTTTATATAA | 543 |
| 6 | LSBS3-R | GTCTTGAAGGATGTCTTGGAGAG | TGTTAAATCCAAGTATGGCAGGCAGGGATATTTCTGACCTAACCATAAACAAGCTTTGTAAATTCAGCCACACCCTTAACGAAGTAGGTACAATACATATTGCCAATCTGTATCCCTTTTATGAAACCAATTCTACAATGTTATCTTCTCTAATTAAAAACTTACAACACGAAAATACAAATTTATTTGATACAGTAATGGCAACTAATCGGCAGGTATTGAGCTCCCTTGTAAGAGACTCAAAAAAGTCGTCTTGGCTTGGGGAGATTGCCCTGATTTATTTGATAGGCAATTCCATAAAAAACAATGTAATGACTTTATGTTGTTGCTTAAAGAAGCGAATCAGAATCAGGTTTATGTAATAAAAACTCATTTTGACAAGCTTCTAACTGTGAAAAACTCTCCAAGACATCCTTCAAGAC (SEQ ID NO: 32) | |

TABLE 7-continued

Primers for Unique Signature Sequences

| SEQ ID NO | Primer Name | Primer Sequence | PCR Product | Size (bp) |
|---|---|---|---|---|
| 7 | LSBS4-F | CATGCGGAACTCCAA TTTCTTC | CATGCGGAACTCCAATTTCTTCTTGAGCAAAAATAGCATCTTTGTGAGCTTGGATAGCAT CATCATAAGTTTTAACGTGCGCTCCCTTAACATATAATCCGAATTTCGCATTCATTGTCA | 263 |
| 8 | LSBS4-R | TAGCGATGCCTCAAT AAGGATTTA | TCATCCTTTTATTTTATTTTAATTTTCTCTTCAGGATAGTCAGATAATGCCTAATTGAAT GTCTAGCATCCGCCAATTCATGTACCCACTTTTCATTGGGTATAGAATTCCACTTTTTAT AAATCCTTATTGAGGCATCGCTA (SEQ ID NO: 33) | |
| 9 | LSBS5-F | CCATTAGGGTCAACA TGGTCTAA | CCATTAGGGTCAACATGGTCTAAATGGAGTTTTTGATTGTTAACTTTAAAATGGTCTATC TCCGATAATCCACAATAAGCACAACTGTAGTTAAAATATGATTTACACCTGTCTCTCTCA | 273 |
| 10 | LSBS5-R | TGCTAAGAGTGACA AAGGAAGAG | ACCTCAGAAACTTTATGTTTTTTCTCTTTCCTTTTCAACTGGTAAAACTTTATTTTTTCT TTATTTAACCTTTGGTATTCTCTTATGTAACCGTTTTGAGTTCTCTTCTTCCAAGCAATA TTGTTCCGTTCTCTTCCTTTGTCACTCTTAGCA (SEQ ID NO: 34) | |
| 11 | LSBS6-F | CACCGAACTCTGCTG AGAAA | CACCGAACTCTGCTGAGAAAACACATCTGTATGCGCAACCTTTAATTTTCATATAAGATG TTTGGATGATATCCTCTTCATAAATTTCCTTCCCTTTCTTATCCTTAAGCCCCGTATATT | 523 |
| 44 | LSBS6-R | CACCGAACTCTGCTG AGAAA | GCATGAGAATGTTTGACTTACAATAGCTAACCGTTGGTTGTTTTAAGGTAAATTCATAAA GCATCTCTTTTTTGTCTTTAATCCATGAGCGAAATTTAATTTCCTTCATTTTGCGCCTCC TGAAGCTTATTCTTTTGCTCTGCAATCTCCATTTCTGTCATGCCACAGTCAGAACAACAT TCATAGTCAGGTATTTGCAAATAATCTTCTCCCGGCATAGTGCAATAACTCATTTCCATG TGCCTATGTTCACAGGATTCCTGACGTTTTTCTGTTCTTCCTCTTTGACAACTGAGCAA TATACTCTTTCGTGAAGCCTAGCCCCGTGCTTTGTCATCAGCCGCTTTCCACAATGTTCA CACTGATAAAGTGTCTGATTCTCTAACACTTTCATTCTGCCGC (SEQ ID NO: 35) | |
| 12 | LSBS7-F | CCTCTGCCCAAGACA TATCAA | CCTCTGCCCAAGACATATCAAATGTATCTTGCGAACTCACTAGTAAAATTTTTTAATAT TTTTGAAGAAAGTAATATCCTTTAATAATTCTTCTCTAAGCTTCTGTTTTGTCAGAGGCA | 913 |
| 13 | LSBS7-R | ATCGGTAAACATAG GCCTCTTAC | AAAGAGGGTAAATAATTGCAAAATCCAAATCACTTGGTGTCTTATCCCATGTGCTTCTAG TAATAGTGTCAATATAAACTGTACTTCCGTTCAAATTATAAGGGACTCCTGTTTTTAAAG TTCCAGTTGCCTTCATAAACACCTTAGCATTATCTAAGCTGCTAGTTCTAAGTAAAATTC TTGATCCAACAAAATTCTCAGTAATGGTTTTAAACACAAGTTCATGTTTCTTAAACATAT TGTTCCAGTCATTAAAGCAACTTTTTCATTTGATTCAATAAAAGAAAGAATTTTCTCAA CTGCTTGACCTTTGTTATTGCTCATACTTTTCACCTTCATTTTTAATTTTTAAAACGTAG TACAATTAACAATGCAGATTACTATAAAATCAACTATGTTAATTTAGCGATTAATAGTAT AGTAATATCAAACACTAGATGCACTATGTATCCAATAAAAAAGTTCCCTGATCGGAAAAA CAAAAAAACTTGCATTAATGTAAAAGGTAAGCCGATTAAAAAAACGCATTGAAGAACATT ACCGTTATATACTGCCAAATGCGCTAGACCAAAAATTAAAATTGCAGGGATTAAAGATAT TATCACGACAATTTTATTGTTAAGTTTCACTTTTAAAAACAATAAAAAGAAAAAGTAATA CACAGAAAAGAACAGAATTTGCTCTGCTATAAGACTAATCGATAAACTATAAATAGTAAT ACCGATTGGATCCTCAACTGCAGGATTTGCACTTGGCTTTATTCCTTTTAGTAAGAGGCC TATGTTTACCGAT (SEQ ID NO: 36) | |
| 14 | LSBS8-F | GCTGTAGACGACTGG GTACTA | GCTGTAGACGACTGGGTACTATATTATAGTTAAATGAATAAATTCCAGTTCGTTCCCCTT TAATTAATCCATCATAGTCAAATATTTTTTAGTTCCATCGCTAAACTCGAAAAACACTT | 750 |
| 15 | LSBS8-R | TTGGTGAGTTGGAGT TGATTCT | CAATATTATCCTTTGTATTCACTTCCAAATGCCTCCTTGTTTTTCACAACTCTAATTTAG CATCCATTGATAATTTGTTTTCCATTAATACGAAGGACTTGGTCATTTCTGATATTATTA TTGCTTCTTTTTTTATTAATACTAGGAGCACTGGTGCTTCCATGACCAGCTAGGGGTTCTA AATTTCTTTTTTTATAAATATCATGGATATAATCTAAAATTTCATTTGGCAATCTTGATT CTTTTCTGTATAAATCAAAAAAGAACCAAGACTTTGATCTCCTATTGTGTCCCTATCAA TAATGTCTTTTGCCAATGTTTCTAAAATTGTCGCTGAAGTATGTAACACTCCAGAATAAT CCTGTTTATCAAACAATAAATTCATTCGGTCTATCAACAACCTAATATTTGGGTGCTCCT CAATATCATTGAACTGTGCTTCTTCTGTTAACGAAAATGTAGTTAGTTGAAATCCATCCT CAGTTTCTTCAATATAAAAGAAGCTGAACTTTCATTGAATAGTTTTGAAACAACATCTA AAGACAGTATTCCTTGTTCCAACAAATCAATAATTATTTCAATAAATTGAATAGTGTTTG GTATTCTTAGAATCAACTCCAACTCACCAA (SEQ ID NO: 37) | |
| 16 | LSBS9-F | GCCATCAGGCTGTTT GTAGA | GCCATCAGGCTGTTTGTAGAAAGTAACCTTTGCCACAACGCTCCTCCTAAAGTTTTACTC AACAAATCCTATGTCTATAATTATATCGGCATCTACACCAAGGCCTGAACACCCCTTTGA | 679 |
| 17 | LSBS9-R | GGCGCAGTTTGGATA GAGATAA | CAAATATAAATGCAAATCCTAGCTGATCGTAATCACTTTTTCGATTTTCTTTACAAATTC AATAAACTGATTTTGCTTGAAGAATACCAAGCTTTTCATATTTCACCGGTAAAGAGCCA TTGAGGGTTTTCCCCAGTTGTCTGTATCTCCATGATAAAACTTGTTCCTTTTGTGTTGAT CTCTTCATCTTCCTGAATTTCATAATGATGTGTAATTAATTTTTTCAAAGAGTGGCTGTC CTTTATTTCTTTTGTATAAAATGATAATCCCTGCTCCTCATACCGCTTTAGTTCAAAGCC ATTATCCACTAAAAAGTTTAAGTTGTTTTGATTTAATGTAAGCAAAATTTATTTCCCCTT TCATTAAAACTGCTGTTTTATTCAGATTTTAAGGCATTCACAAGCTTCTCCCTGCACTCA TCGCAAACGTGTATTATGCTTGTCGCATATGGCAAACAAATACTATATACACCTTTCAAT CTTCTATTCCCACATCCATTGCAATGTTTAGTTTCTTCGTTTTATGTACACTAATTTTA TCTCTATCCAAACTGCGCC (SEQ ID NO: 38) | |
| 18 | LSBS10-F | CAGATGAAGTTGGTG GTGTTTC | CAGATGAAGTTGGTGGTGTTTCTTCTTCGATGGTAGACTCAATGAAGTAAACTGGAGTAT TTGTGAATGTAACGGAGATGTTTTCGTTAAGTTTGTGTGTGGTGAATTGACCTATATCAA | 743 |
| 19 | LSBS10-R | CGTGCCTTTACCTGC TATCT | CGTTTGATTGGATGTACTTATCAATTCAAGTTCTTTTTTGTTTGTGTTGCAACATTCGGTA ATATTGTTTTGCTGTTAGTTCAACATAATATTTTGTCAAAGCCTTTTCGGTGAATTCGT TTTTAGAATTGAACTGATCTACTGCATTTTCTAATTGTTCTTCATCTTGAGGATTAGAGA TTTTTAGTGTAACTAAAAGCAAATCTTGATATTCTTGAATTGAATTGATCTCATTCTTTT CGCTTGCACTTGCTGTTTTACTTCCAGTGGCAAATGTGAAAGATGACAGAATTAACACGA AACCCAAAATAGAAAAAAGTGTTTTTTAAATTTCCCCATAGTAACAGCTCCTTTTTTGA | |

TABLE 7-continued

Primers for Unique Signature Sequences

| SEQ ID NO | Primer Name | Primer Sequence | PCR Product | Size (bp) |
|---|---|---|---|---|
| | | | TTGATAATAGAGCCTTCTATGTTGATTAAACCTGTTGTAGGCATTTTATAATATGTCCCT CCTTTCAATTAGAACCATAACATATAATCTATGTCCAATTCTATACATTTTAGCAATTTT AAGGTAATATTATTTACTCATAAGTGAATGACATCCCAAAATCACAATAGGACATATAAA CTATTCCCTTTCTAGTGAAGGGAAAATAATATTGATATATTAGAGAGCCATTTTTATAAC AATAGATAGCAGGTAAAGGCACG (SEQ ID NO: 39) | |
| 20 | LSBS11-F | ATGCGGCTAGACATG GATATG | ATGCGGCTAGACATGGATATGTTCGTTTAACAATGAAATGCAACTCCCCTTATGCATACA GTCGAAACACAAGTACCCATTCCTTTGATATATCATCAGAAATGAAAATCATTGAACTCC | 687 |
| 21 | LSBS11-R | ACCAAATCGTAAGCC CATAGAA | ATAATAAAGGCGATGTTGCGATTTACCCCACTGTTGAAATTCTTAAAATTGGCGATGGCG ATGTGAAAATCGAGAACCTAAGTGATTATACTGCCCCCTTTATTTTCAGCAATCTAAAAG ACAGAGAAATTGTTAAAGTGAATGGCGTCAAAGAAACAATTGAATCGTCTTTATATGGGA ATGAAAGATATGATGATTTTAATGACAATTATATTAAATTGGATTACGGAAAAAACCGAT TAAAAGTGACCGGAAAATGCAAACTGAGATTCACTTTCAGATTTAAGTATCGATAAGAAG GTGAAAAATTGATAACTATTCGCAAGGACACAGAAATAAAAAACATACGCTTATCCCTTG CTAAGCCAGACAAGACTAAAATAGCCAACATTGATGAAGTTCTGAATCCAACTGTAACTT TAAATCATGGAAGCAGCGTTCACGAACTCTCCTTCTCTATTCCGCTTAAAGCAACCTATG ATGGCATAATTAAAAGAAACCATGTTGTAGATTTACTAAAACCCTGGTACCTAATTAAAA CAGCGTTCTATGGGCTTACGATTTGGT (SEQ ID NO: 40) | |
| 22 | LSBS12-F | TGTCCCTCTTTAGGT GCTATTG | TGTCCCTCTTTAGGTGCTATTGATAAAATTTTAACCCAATTGTAAGTCCACTCGTTGTAT GTCCAAAATTCAAATTGCTTTTTTCCATAAACATTTTTCCCCACCATCGCATATCTAAAC | 954 |
| 23 | LSBS12-R | TCAGGACTTTAGCCG ATGTTTAT | CAATTACTGCCAGTTTTTTGAGGTTGAAAAACTTTATCGTTTTTATTTTCCTCAAATGTA ACAGGAATCAAGGAAGAAACGTATGCTAACTGATCATCTTCATTTAGTGTCTTAACATAA CTTTCAACAAGACTGCTTGCTTCTTTTGATTCCATTTTGATTTTCTTTGTTTTAAGTTTA TTCTGGATGTTTTGTTCGATTTTCTTTGATGGTTCTTTAGTAAACTCTATTATCTTTTGT TTCTCGTCATCGTTAAATTTATCCCATGAATCAGGTTGAGCAACGAATTGCTTAGTGAGC TCTTTAGCTGAATTTAACGATGCTGCATGCGCAGTTGTCATATTAAAACCTGCAAGAGAT ACAATCGCTAACACTAATGATAGAATCAGCTTTTCATATAGACACACTCCTTATATATC TTCTGTTTTTTATTGAAAAACCCTTTTCATTTTTCGAATTTCTTCTCAAATAGCAGAACA ACCTAGTGAATAGTTTTATCCGGTTCCAAAAAATAATTAAGTGTGCTCCTCCTCCCTCTA ATGATTAGATCAAAAGCTATTGCAAGGTTATGAGTCAGAAGACCCTCAATACCATATCAC CTCCTAACGCAACCCTACCACACTCTTATCTTTCATTAAATAGCTTAACTTCCAAATGAT AGTTTATGACTAAATTGAAAAAAAACAGAAAATCCGCAATGATTTACGGAACCTTCTGTC TTTTGAAAATTGACCTAACGTCATGTTTTTTGGATAAAAAGCTTCTTTTGATGCTGATTA TTCGCCATAACCATGTAATAAGAAGCTATCTATAAACATCGGCTAAAGTCCTGA (SEQ ID NO: 41) | |
| 24 | LSBS13-F | CCCTCTAGCTCTTTC TTCTTCAC | CCCTCTAGCTCTTTCTTCTTCACTTTCCAGTCGTTTGGAGGCAGTCCCTTACCTTTGTTT TTGAAGAGCATCATTTTGTACCTAGACTCTAAAAGCTGATAATAAATGATAACCTTATCG | 496 |
| 25 | LSBS13-R | GCCAATATTTCTAGA GTGGGTACT | TCTTCCTCCATATGCTTCAAGGATTCCTTAGCTTTTTTAAGAAGTTGCTCTGCCAAATCT ATCTCACATTTCTTAATAGCAACATGAAGTTCATTCAGAGTATTAGCTACTACCTCGTGT GCGATCGTACCCATTTATAACCCCTCTTTTCTAAAATGTTTCGAATTATTAAACAATATA ACAGACATTTGCAATATTTGGAATAATTTAAAAGTGGTTTTCGGTAAGTTTTCGTCATAC CGCAATAACCTTTTGGGGAAGGCATGCTAAAAAAGTCCCTATTTCTTTTAATCAGTCGGC CTACTGATTGCATTATTCGCTTGAAATAAATAAAAGCGGGCTCCGAAAATGGAGTACCCA CTCTAGAAATATTGGC (SEQ ID NO: 42) | |

"Primers" are isolated nucleic acids that are annealed to a complementary target DNA strand by nucleic acid hybridization to form a hybrid between the primer and the target DNA strand, and then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic acid amplification methods.

Probes and primers are generally 11 to 30 nucleotides or more in length. In certain instances, probes and primers can have lengths of more than 30 nucleotides. Regardless of size, probes and primers can hybridize specifically to a target sequence under high stringency hybridization conditions. Preferably, probes and primers according to the present invention have complete sequence identity with the target sequence, although probes differing from the target sequence and that retain the ability to hybridize to target sequences may be designed by conventional methods.

As discussed above, one aspect of the invention relates to identification of B series microbes. Related PCR primers and amplicons are included in the invention. According to the subject invention, analytic PCR methods and other similar methods can be used to detect DNA sequences associated with B series microbes.

One skilled in the art will also recognize that primers and probes can be designed to hybridize, under a range of standard hybridization and/or PCR conditions, including conditions where the primer or probe is not perfectly complementary to the exemplified sequence. That is, some degree of mismatch can be tolerated. For an approximately 20 nucleotide primer, for example, typically one or two or so nucleotides do not need to hybridize with the opposite strand if the mismatched base is internal or on the end of the primer that is opposite the amplicon. Various appropriate hybridization conditions are provided below. Furthermore, synthetic nucleotide analogs, such as inosine, can also be used in probes. Peptide nucleic acid (PNA) probes, as well as DNA and RNA probes, can also be used.

Such methods can comprise: (a) contacting the sample comprising DNA with a primer set that, when used in a nucleic acid amplification reaction with DNA, produces an amplicon that identifies a B series microbe within the sample; (b) performing a nucleic acid amplification reaction, thereby producing the amplicon; and (c) detecting the amplicon.

A "probe" is an isolated nucleic acid molecule to which is attached a conventional detectable label or reporter molecule (such as a radioactive isotope, ligand, chemiluminescent agent, or enzyme). Probes according to the present invention include not only deoxyribonucleic or ribonucleic acids but also polyamides and other probe materials that bind specifically to a target DNA sequence and can be used to detect the presence of that target DNA sequence. Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989.

Depending on the application, one can use varying conditions of hybridization to achieve varying degrees of selectivity of probe towards target sequence. For applications requiring high selectivity, one will typically employ relatively stringent conditions to form the hybrids, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses. In a particular embodiment, a primer or probe disclosed herein will specifically hybridize to target genomic DNA. The hybridization of the probe or primer to DNA can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon. The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202. PCR amplification methods have been developed to amplify up to 22 kb of genomic DNA. These methods as well as other methods known in the art of DNA amplification may be used in the practice of the present invention. The amplicon produced by these methods may be detected by a plurality of techniques. Agarose gel electrophoresis and staining with ethidium bromide is a common well known method of detecting DNA amplicons.

TAQMAN (PE Applied Biosystems, Foster City, Calif.) is a method of detecting and quantifying the presence of a DNA sequence. Briefly, a FRET oligonucleotide probe is designed that hybridizes with a sequence of interest (e.g., a sequence containing mutations). The FRET probe and PCR primers are cycled in the presence of a thermostable polymerase and dNTPs. During specific amplification, Taq DNA polymerase cleans and releases the fluorescent moiety away from the quenching moiety on the FRET probe. A fluorescent signal indicates the presence of the sequence of interest due to successful amplification and hybridization. Molecular beacons have also been described for use in sequence detection and can be used in accordance with the subject invention.

According to another aspect of the invention, methods of detecting the presence of a DNA corresponding to a B series microbe in a biological sample are provided. These, methods comprise: (a) contacting the biological sample with a probe that hybridizes under stringent hybridization conditions with genomic DNA from a B series microbe and does not hybridize under the stringent hybridization conditions with a microbe; (b) subjecting the biological sample and probe to stringent hybridization conditions; and (c) detecting hybridization of the probe to the target DNA, wherein detection of such hybridization in indicative of presence of the target DNA.

Example 18—Anti-Microbial Activity

In further embodiments of the subject invention, the microbe-based compositions of the current invention can be used for anti-microbial uses, including uses against drug resistant microbes such as MRSA. These uses include, but are not limited to, disinfecting surfaces, plumbing, pipes, air conditioning units, livestock areas, marine fouling, fountains, and other wet or moist areas.

What is claimed:

1. A method for enhancing the amount of oil recoverable from an oil-containing formation, wherein said method comprises applying a composition comprising *Bacillus subtilis* strain B1 having accession number PTA-123459 to the oil-containing formation.

2. The method of claim 1, wherein the microbe is in the vegetative state.

3. The method of claim 1, which further comprises administering one or more other microorganisms.

4. The method of claim 3, wherein the one or more other microorganisms are selected from *Bacillus, Geobacillus, Candida, Starmerella, Yarrowia, Pseudomonas, Nocardioides, Rhodococcus, Arthrobacter* and *Acinetobacter.*

* * * * *

SEQUENCE LISTING

<160> NUMBER OF SEQ ID NOS: 44

<210> SEQ ID NO 1
<211> LENGTH: 21
<212> TYPE: DNA
<213> ORGANISM: Artificial

```
<220> FEATURE:
<223> OTHER INFORMATION: primer

<400> SEQUENCE: 1
ggacacagat cattgggagt t                                              21

<210> SEQ ID NO 2
<211> LENGTH: 23
<212> TYPE: DNA
<213> ORGANISM: Artificial
<220> FEATURE:
<223> OTHER INFORMATION: primer

<400> SEQUENCE: 2
tgacgagagc ctttatggat tac                                            23

<210> SEQ ID NO 3
<211> LENGTH: 22
<212> TYPE: DNA
<213> ORGANISM: Artificial
<220> FEATURE:
<223> OTHER INFORMATION: primer

<400> SEQUENCE: 3
tcaattcctc tgcaccactt at                                             22

<210> SEQ ID NO 4
<211> LENGTH: 23
<212> TYPE: DNA
<213> ORGANISM: Artificial
<220> FEATURE:
<223> OTHER INFORMATION: primer

<400> SEQUENCE: 4
gaagaagtta gctgggttgt ttg                                            23

<210> SEQ ID NO 5
<211> LENGTH: 24
<212> TYPE: DNA
<213> ORGANISM: Artificial
<220> FEATURE:
<223> OTHER INFORMATION: primer

<400> SEQUENCE: 5
cggagtttgt tagcgaagtt attg                                           24

<210> SEQ ID NO 6
<211> LENGTH: 23
<212> TYPE: DNA
<213> ORGANISM: Artificial
<220> FEATURE:
<223> OTHER INFORMATION: primer

<400> SEQUENCE: 6
gtcttgaagg atgtcttgga gag                                            23

<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
catgcggaac tccaatttct tc                                             22
```

```
<210> SEQ ID NO 8
<211> LENGTH: 24
<212> TYPE: DNA
<213> ORGANISM: Artificial
<220> FEATURE:
<223> OTHER INFORMATION: primer

<400> SEQUENCE: 8
tagcgatgcc tcaataagga ttta                                           24

<210> SEQ ID NO 9
<211> LENGTH: 23
<212> TYPE: DNA
<213> ORGANISM: Artificial
<220> FEATURE:
<223> OTHER INFORMATION: primer

<400> SEQUENCE: 9
ccattagggt caacatggtc taa                                            23

<210> SEQ ID NO 10
<211> LENGTH: 23
<212> TYPE: DNA
<213> ORGANISM: Artificial
<220> FEATURE:
<223> OTHER INFORMATION: primer

<400> SEQUENCE: 10
tgctaagagt gacaaaggaa gag                                            23

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
caccgaactc tgctgagaaa                                                20

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
cctctgccca agacatatca a                                              21

<210> SEQ ID NO 13
<211> LENGTH: 23
<212> TYPE: DNA
<213> ORGANISM: Artificial
<220> FEATURE:
<223> OTHER INFORMATION: primer

<400> SEQUENCE: 13
atcggtaaac ataggcctct tac                                            23

<210> SEQ ID NO 14
<211> LENGTH: 21
<212> TYPE: DNA
<213> ORGANISM: Artificial
<220> FEATURE:
<223> OTHER INFORMATION: primer
```

<400> SEQUENCE: 14
gctgtagacg actgggtact a                                              21

<210> SEQ ID NO 15
<211> LENGTH: 22
<212> TYPE: DNA
<213> ORGANISM: Artificial
<220> FEATURE:
<223> OTHER INFORMATION: primer

<400> SEQUENCE: 15
ttggtgagtt ggagttgatt ct                                             22

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
gccatcaggc tgtttgtaga                                                20

<210> SEQ ID NO 17
<211> LENGTH: 22
<212> TYPE: DNA
<213> ORGANISM: Artificial
<220> FEATURE:
<223> OTHER INFORMATION: primer

<400> SEQUENCE: 17
ggcgcagttt ggatagagat aa                                             22

<210> SEQ ID NO 18
<211> LENGTH: 22
<212> TYPE: DNA
<213> ORGANISM: Artificial
<220> FEATURE:
<223> OTHER INFORMATION: primer

<400> SEQUENCE: 18
cagatgaagt tggtggtgtt tc                                             22

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
cgtgccttta cctgctatct                                                20

<210> SEQ ID NO 20
<211> LENGTH: 21
<212> TYPE: DNA
<213> ORGANISM: Artificial
<220> FEATURE:
<223> OTHER INFORMATION: primer

<400> SEQUENCE: 20
atgcggctag acatggatat g                                              21

<210> SEQ ID NO 21

<211> LENGTH: 22
<212> TYPE: DNA
<213> ORGANISM: Artificial
<220> FEATURE:
<223> OTHER INFORMATION: primer

<400> SEQUENCE: 21
accaaatcgt aagcccatag aa                                              22

<210> SEQ ID NO 22
<211> LENGTH: 22
<212> TYPE: DNA
<213> ORGANISM: Artificial
<220> FEATURE:
<223> OTHER INFORMATION: primer

<400> SEQUENCE: 22
tgtccctctt taggtgctat tg                                              22

<210> SEQ ID NO 23
<211> LENGTH: 23
<212> TYPE: DNA
<213> ORGANISM: Artificial
<220> FEATURE:
<223> OTHER INFORMATION: primer

<400> SEQUENCE: 23
tcaggacttt agccgatgtt tat                                             23

<210> SEQ ID NO 24
<211> LENGTH: 23
<212> TYPE: DNA
<213> ORGANISM: Artificial
<220> FEATURE:
<223> OTHER INFORMATION: primer

<400> SEQUENCE: 24
ccctctagct ctttcttctt cac                                             23

<210> SEQ ID NO 25
<211> LENGTH: 24
<212> TYPE: DNA
<213> ORGANISM: Artificial
<220> FEATURE:
<223> OTHER INFORMATION: primer

<400> SEQUENCE: 25
gccaatattt ctagagtggg tact                                            24

<210> SEQ ID NO 26
<211> LENGTH: 1553
<212> TYPE: DNA
<213> ORGANISM: Bacillus subtilis

<400> SEQUENCE: 26
tttatcggag agtttgatcc tggctcagga cgaacgctgg cggcgtgcct aatacatgca      60
agtcgagcgg acagatggga gcttgctccc tgatgttagc ggcggacggg tgagtaacac     120
gtgggtaacc tgcctgtaag actgggataa ctccggaaaa ccggggctaa taccggatgg     180
ttgtttgaac cgcatggttc aaacataaaa ggtggcttcg ctaccactt acagatggac      240 ccgcggcgca ttagctagtt ggtgaggtaa cggctcacca aggcgacgat gcgtagccga     300
cctgagaggg tgatcggcca cactgggact gagacacggc ccagactcct acggaggca      360 gcagtaggga atcttccgca atggacgaaa gtctgacgga caacgccgc gtgagtgatg     420

```
aaggttttcg gatcgtaaag ctctgttgtt agggaagaac aagtaccgtt cgaatagggc      480
ggtaccttga cggtacctaa ccagaaagcc acggctaact acgtgccagc agccgcggta      540
atacgtaggt ggcaagcgtt gtccggaatt attgggcgta aagggctcgc aggcggtttc      600
ttaagtctga tgtgaaagcc cccggctcaa ccggggaggg tcattggaaa ctggggaact      660
tgagtgcaga gaggagagt ggaattccac gtgtagcggt gaaatgcgta gagatgtgga      720
ggaacaccag tggcgaaggc gactctctgg tctgtaactg acgctgagga gcgaaagcgt      780
ggggagcgaa caggattaga taccctggta gtccacgccg taaacgatga gtgctaagtg      840 ttaggggggtt tccgccccctt agtgctgcag ctaacgcatt aagcactccg cctggggagt      900
acggtcgcaa gactgaaact caaaggaatt gacggggggcc cgcacaagcg gtggagcatg      960
tggtttaatt cgaagcaacg cgaagaacct taccaggtct tgacatcctc tgacaatcct     1020
agagatagga cgtccccttc ggggggcagag tgacaggtgg tgcatggttg tcgtcagctc     1080
gtgtcgtgag atgttgggtt aagtcccgca acgagcgcaa cccttgatct tagttgccag     1140
cattcagttg ggcactctaa ggtgactgcc ggtgacaaac cggaggaagg tggggatgac     1200
gtcaaatcat catgccccctt atgacctggg ctacacacgt gctacaatgg acagaacaaa     1260
gggcagcgaa accgcgaggt taagccaatc ccacaaatct gttctcagtt cggatcgcag     1320
tctgcaactc gactgcgtga agctggaatc gctagtaatc gcggatcagc atgccgcggt     1380
gaatacgttc ccgggccttg tacacaccgc ccgtcacacc acgagagttt gtaacacccg     1440
aagtcggtga gtaaccttt taggagccag ccgccgaagg tgggacagat gattgggggtg     1500 aagtcgtaac aaggtagccg tatcggaagg tgcggctgga tcacctcctt tct           1553
```

<210> SEQ ID NO 27
<211> LENGTH: 801
<212> TYPE: DNA
<213> ORGANISM: Bacillus subtilis

<400> SEQUENCE: 27

```
gtggagaaaa ttaaagtttg tgttgctgat gataatcgag agctggtaag cctgttaagt       60
gaatatatag aaggacagga agacatggaa gtgatcggcg ttgcttataa cggacaggaa      120
tgcctgtcgc tgtttaaaga aaaagatccc gatgtgctcg tattagatat tattatgccg      180
catctagacg gacttgcggt tttagagagg ctgagggaat cagatctgaa aaaacagccg      240
aatgtcatta tgctgacagc ctttgggcag gaagatgtca cgaaaaaggc cgtcgattta      300
ggcgcgtcct actttattct caaaccgttt gatatggaaa accttgtcgg ccatatccgc      360
caggtcagcg gaaatgccag cagtgtgacg catcgtgcgc catcatcgca aagcagtatt      420
atacgcagca gccagcctga accaaagaag aaaaatctcg acgcgagcat cacaagcatt      480
atccatgaaa tcggcgtccc agcccatatt aaaggctatc tctatctgcg cgaagcaatc      540
tcaatggtat acaatgacat cgaattgctc ggcagcatta caaagtcct ctatccggac      600 atcgccaaaa aatttaacac aaccgcaagc cgtgtagaaa gagcgatccg ccatgcaatt      660
gaagtggcat ggagcagagg aaacattgat tccatttcct cgttgtttgg ttatactgtc      720
agcatgacaa aagctaaacc taccaacagt gaattcattg caatggttgc ggataagctg      780
aggttagagc ataaggcttc t                                                801
```

<210> SEQ ID NO 28
<211> LENGTH: 1917
<212> TYPE: DNA

<213> ORGANISM: Bacillus subtilis

<400> SEQUENCE: 28

```
atggaacagc agcaaaacag ttatgatgaa atcagatac aggtactaga aggattggaa      60
gctgttcgta aaagaccggg gatgtatatc ggttcgacaa acagcaaagg ccttcaccac    120
ctggtatggg aaattgtcga caatagtatt gacgaagccc tcgccggtta ttgtacggat    180
atcaatatcc aaatcgaaaa agacaacagt atcacggttg tagataatgg ccgcggtatt    240
ccagtcggta ttcatgaaaa aatgggccgt cctgcggtag aagtcattat gacggtactt    300
catgccggag aaaatttga cggaagcggc tataaagtat ccggaggatt acacggtgta    360
ggtgcgtctg tcgtaaacgc actatcaaca gagcttgatg tgacggttca ccgtgacggt    420
aaaattcacc gccaaactta taacgcgga gttccggtta cagaccttga atcattggc     480
gaaacggatc atacaggaac gacgacacat tttgtcccgg accctgaaat tttctcagaa    540
acaaccgagt atgattatga tctgcttgcc aaccgcgtac gtgaattagc cttttttaaca    600
aagggcgtaa acatcacgat tgaggataaa cgtgaaggac aagagcgcaa aaatgaatac    660
cattacgaag cggaattaa aagttatgta gagtatttaa accgctctaa agaggttgtc    720
catgaagagc cgatttacat tgaaggcgaa aaggacggca ttacggttga agtggctttg    780
caatacaatg acagctacac aagcaacatt tactcgtttta caaacaacat taacacgtac    840
gaaggcggta cccatgaagc tggcttcaaa acgggcctga ctcgtgttat caacgattac    900
gccagaaaaa aagggcttat taaagaaaat gatccaaacc taagcggaga tgacgtaagg    960
gaagggctga cagcgattat ttcaatcaaa caccctgatc cgcagtttga gggccaaacg   1020
aaaacaaagc tggcaactc agaagcacgg acgatcaccg atacgttatt ttctacggcg   1080
atggaaacat ttatgctgga aaatccagat gcagccaaaa aaattgtcga taaggctta   1140
atggcggcaa gagcaagaat ggctgcgaaa aaagcccgtg aactaacacg tcgtaagagt   1200
gctttggaaa tttcaaacct gcccggtaag ttagcggact gctcttcaaa agatccgagc   1260
atctccgagt tatatatcgt agagggtgac tctgccggag gatctgctaa caaggacgc   1320
gacagacatt tccaagccat tttgccgctt agaggtaaaa tcctaaacgt tgaaaaggcc   1380
agactggata aaatcctttc taacaacgaa gttcgctcta tgatcacagc gctcggcaca   1440
ggtattgggg aagacttcaa ccttgagaaa gcccgttacc acaaagttgt cattatgaca   1500
gatgccgatg ttgacggcgc gcacatcaga acactgctgt taacgttctt ttacagatat   1560
atgcgccaaa ttatcgagaa tggctacgtg tacattgcgc agccgccgct ctacaaggtt   1620
caacagggga acgcgttga atatgcgtac aatgacaagg agcttgaaga gctgttaaaa   1680
actcttcctc aaaccccctaa gcctggactg cagcgttaca aaggtcttgg tgaaatgaat   1740
gccacccagc tatgggagac aaccatggat cctagctcca gaacacttct tcaggtaact   1800
cttgaagatg caatggatgc ggacgagact ttgaaatgc ttatgggcga caaggtagaa   1860
ccgcgccgaa acttcatga agcgaatgcg agatacgtta aaaatcttga catctaa       1917
```

<210> SEQ ID NO 29
<211> LENGTH: 579
<212> TYPE: DNA
<213> ORGANISM: Bacillus subtilis

<400> SEQUENCE: 29

```
atgagtcaga aaacagacgc accttttagaa tcgtatgaag tgaacggcgc aacaattgca      60
gtgctgccag aagaaataga cggcaaaatc tgttccaaaa ttattgaaaa agattgcgtg    120
```

```
ttttatgtca acatgaagcc gctgcaaatt gtcgacagaa gctgccgatt ttttggatca      180
agctatgcgg gaagaaaagc aggaacttat gaagtgacaa aaatttcaca caagccgccg      240
atcatggtgg acccttcgaa ccaaatcttt ttattcccta cactttcttc gacaagaccc      300
caatgcggct ggatttccca tgtgcatgta aagaattcaa agcgactga atttgacgat       360 acggaagtga cgttttcaaa tgggaaaacg atggagctgc cgatctctta taattcgttc      420
gagaaccagg tataccgaac agcgtggctc agaaccaaat ccaagacag aatcgaccac       480 cgcgtgccga aaagacagga atttatgctg tacccgaaag aagagcggac gaagatgatt     540
tatgatttta ttttgcgtga gctcggggaa cggtattag                             579

<210> SEQ ID NO 30
<211> LENGTH: 769
<212> TYPE: DNA
<213> ORGANISM: Artificial
<220> FEATURE:
<223> OTHER INFORMATION: PCR amplicon

<400> SEQUENCE: 30
ggacacagat cattgggagt taatcttgaa taacagaata atttctataa atcgaaactt       60
tggttatgca atgttttact attataaagg cattccagat gatgaatggt ttatatcacc     120
tgggaaagaa ggtcagtcag ttgaattttt tcctcacttt gatgatcaac acacaagtaa     180
tcactttaac tttaaatact tgtagatat tttcttttg aaagcataca cagtctatga       240
aacaattgga catttattat acaaattgta tgacttggaa atcaatgagg acgatcctag     300
agaccaagta agtttcaaaa gtgccatttt taaattaaag cccgaaaatc atcgactcta     360
taaagacctt tgcaaattaa aacgctctga tgattttaaa aaggggtag ctatgagaaa      420 tgatattgca cataatcacc caccttacga tatagattcc ggggtaacaa aatcgaaagg     480
tgggataatc acaatgggaa ttggcaatta caaccctca aaagaaataa aagaaacaat      540
gatcggcttc cttagaagta ttaaggtcac ttttgaaatg cttgaaaaac atctgcccct      600
aagttgattt tccaaaatag aaaggtaatc cacttagctg ttttgatttc atatcaatat     660
caccatgctc tctcttaaat atgaaataag aaacaaggcc actcttaatg agtagccttt      720
ttcttacttt gataaagttt ctttggtaa tccataaagg ctctcgtca                   769

<210> SEQ ID NO 31
<211> LENGTH: 906
<212> TYPE: DNA
<213> ORGANISM: Artificial
<220> FEATURE:
<223> OTHER INFORMATION: PCR amplicon

<400> SEQUENCE: 31
tcaattcctc tgcaccactt attgcatcaa aagttaacga taacagattg cctttccttg       60 ttagattta tggtacgcca acccctctgt tatgtgttga cggaaacaaa cgattaaaag       120
caaaaacaga aattgaaaaa tcggatgcaa ttgttgctta tttatttgat gaaaattatc     180
tcgacaagat gtttttgat aaggttgatc agcttttcta ttcacttcat tgcgaaactg       240 aagcatgca cagagccatg agcatggggt tttcatctga acaaatttc aacttaactt        300 taatgagtag gtataaatat gtttaactgg tctaatgacc agtttttta taaaatacag      360 atttcattta gaatatatcc agcgctccat cactataagg acatttgcca ctaccctctt     420
cgcatgtaca tatatatttc acctcctatt acagtacaag gcataataca catcttacac     480
```

```
acactttct  tctaagcatt  taatatcttt  ttcaactacg  gaaagaattg  cttcgacgtg      540
ctctattctt  ctatttgccg  acatacattt  tttcgccgcg  ttcgctattt  cgataactaa      600
tccatttggc  gtaattacac  tctgatagcc  attttgtgaa  gtagtagcgt  aaaactttct      660
cgataccttc  ttcgccactt  ctaaggcttc  gtcatgcttt  tctttaaaat  aatctcgcct      720
tttttgcaat  ctcacatact  cgtcggtttt  tcccgcttcg  acaatgctta  aaggaatatt      780
catttacata  actccttaa   tttttcgatt  tcctcgtttg  caaagtaacg  ccactctggc      840
aaagtttcat  ccattagcgt  tatgtttaaa  gcaagtgatt  gcacaaacaa  cccagctaac      900
ttcttc                                                                      906

<210> SEQ ID NO 32
<211> LENGTH: 543
<212> TYPE: DNA
<213> ORGANISM: Artificial
<220> FEATURE:
<223> OTHER INFORMATION: PCR amplicon

<400> SEQUENCE: 32
cggagtttgt  tagcgaagtt  attgagtgta  aaactgaaag  attaacagat  tccatcgaag       60
ctaggtactg  tttatcgata  aaattaaaca  actctttaga  ctcctctttt  gtttatataa      120
tgttaaatcc  aagtatggca  ggcagggata  tttctgacct  aaccataaac  aagctttgta      180
aattcagcca  cacccttaac  gaagtaggta  caatacatat  tgccaatctg  tatccctttt      240
atgaaaccaa  ttctacaatg  ttatcttctc  taattaaaaa  cttacaacac  gaaaatacaa      300
atttatttga  tacagtaatg  gcaactaatc  ggcaggtatt  gagctccctt  gtaagagact      360
caaaaaagt   cgtcttggct  tggggagatt  gccctgattt  atttgatagg  caattccata      420
aaaaacaatg  taatgacttt  atgttgttgc  ttaaagaagc  gaatcagaat  caggtttatg      480
taataaaaac  tcattttgac  aagcttctaa  ctgtgaaaaa  ctctccaaga  catccttcaa      540
gac                                                                         543

<210> SEQ ID NO 33
<211> LENGTH: 263
<212> TYPE: DNA
<213> ORGANISM: Artificial
<220> FEATURE:
<223> OTHER INFORMATION: PCR amplicon

<400> SEQUENCE: 33
catgcggaac  tccaatttct  tcttgagcaa  aaatagcatc  tttgtgagct  tggatagcat       60
catcataagt  tttaacgtgc  gctcccttaa  catataatcc  gaatttcgca  ttcattgtca      120
tcatcctttt  attttatttt  aatttctctct tcaggatagt  cagataatgc  ctaattgaat      180
gtctagcatc  cgccaattca  tgtacccact  tttcattggg  tatagaattc  cactttttat      240
aaatccttat  tgaggcatcg  cta                                                 263

<210> SEQ ID NO 34
<211> LENGTH: 273
<212> TYPE: DNA
<213> ORGANISM: Artificial
<220> FEATURE:
<223> OTHER INFORMATION: PCR amplicon

<400> SEQUENCE: 34
ccattagggt  caacatggtc  taaatggagt  ttttgattgt  taactttaaa  atggtctatc       60
tccgataatc  cacaataagc  acaactgtag  ttaaaatatg  atttacacct  gtctctctca      120
```
acctcagaaa ctttatgttt tttctctttc cttttcaact ggtaaaactt tattttttct    180
ttatttaacc tttggtattc tcttatgtaa ccgttttgag ttctcttctt ccaagcaata    240
ttgttccgtt ctcttccttt gtcactctta gca                                273

<210> SEQ ID NO 35
<211> LENGTH: 523
<212> TYPE: DNA
<213> ORGANISM: Artificial
<220> FEATURE:
<223> OTHER INFORMATION: PCR amplicon

<400> SEQUENCE: 35
caccgaactc tgctgagaaa acacatctgt atgcgcaacc tttaattttc atataagatg     60
tttggatgat atcctcttca taaatttcct tcccttcttt atccttaagc cccgtatatt    120
gcatgagaat gtttgactta caatagctaa ccgttggttg ttttaaggta aattcataaa    180
gcatctcttt tttgtcttta atccatgagc gaaatttaat ttccttcatt ttgcgcctcc    240
tgaagcttat tcttttgctc tgcaatctcc atttctgtca tgccacagtc agaacaacat    300
tcatagtcag gtatttgcaa ataatcttct cccggcatag tgcaataact catttccatg    360
tgcctatgtt cacaggattc ctgacgtttt ttctgttctt cctctttgac aactgagcaa    420
tatactcttt cgtgaagcct agccccgtgc tttgtcatca gccgctttcc acaatgttca    480
cactgataaa gtgtctgatt ctctaacact ttcattctgc cgc                      523

<210> SEQ ID NO 36
<211> LENGTH: 913
<212> TYPE: DNA
<213> ORGANISM: Artificial
<220> FEATURE:
<223> OTHER INFORMATION: PCR amplicon

<400> SEQUENCE: 36
cctctgccca agacatatca aatgtatctt gcgaactcac tagtaaaatt ttttaatat     60 ttttgaagaa agtaatatcc tttaataatt cttctctaag cttctgtttt gtcagaggca    120
aaagagggta ataattgca aaatccaaat cacttggtgt cttatcccat gtgcttctag     180
taatagtgtc aatataaact gtacttccgt tcaaattata agggactcct gttttttaaag   240 ttccagttgc cttcataaac accttagcat tatctaagct gctagttcta agtaaaattc    300
ttgatccaac aaaattctca gtaatggttt taaacacaag ttcatgtttc ttaaacatat    360
ttgttccagt cattaaagca acttttttcat ttgattcaat aaaagaaaga attttctcaa   420
ctgcttgacc tttgttattg ctcatacttt tcaccttcat ttttaatttt taaaacgtag    480
tacaattaac aatgcagatt actataaaat caactatgtt aatttagcga ttaatagtat    540
agtaatatca aacactagat gcactatgta tccaataaaa aagttccctg atcggaaaaa    600
caaaaaaact tgcattaatg taaaaggtaa gccgattaaa aaaacgcatt gaagaacatt    660
accgttatat actgccaaat gcgctagacc aaaaattaaa attgcaggga ttaaagatat    720
tatcacgaca atttttattgt taagtttcac ttttaaaaac aataaaaaga aaagtaata    780 cacagaaaag aacagaattt gctctgctat aagactaatc gataaactat aaatagtaat    840
accgattgga tcctcaactg caggatttgc acttggcttt attccttta gtaagaggcc     900 tatgtttacc gat                                                      913

<210> SEQ ID NO 37

<211> LENGTH: 750
<212> TYPE: DNA
<213> ORGANISM: Artificial
<220> FEATURE:
<223> OTHER INFORMATION: PCR amplicon

<400> SEQUENCE: 37

```
gctgtagacg actgggtact atattatagt taaatgaata aattccagtt cgttcccctt      60
taattaatcc atcatagtca aatatttttt tagttccatc gctaaactcg aaaaacactt     120
caatattatc ctttgtattc acttccaaat gcctccttgt ttttcacaac tctaatttag    180
catccattga taatttgttt tccattaata cgaaggactt ggtcatttct gatattatta    240
ttgcttcttt tttattaata ctaggagcac tggtgcttcc atgaccagct aggggttcta    300
aatttctttt tttataaata tcatggatat aatctaaaat ttcatttggc aatcttgatt    360
ctttttctgta taaatcaaaa aaagaaccaa gactttgatc tcctattgtg tccctatcaa    420
taatgtcttt tgccaatgtt tctaaaattg tcgctgaagt atgtaacact ccagaataat    480
cctgtttatc aaacaataaa ttcattcggt ctatcaacaa cctaatattt gggtgctcct    540
caatatcatt gaactgtgct tcttctgtta acgaaaatgt agttagttga aatccatcct    600
cagtttcttc aatataaaaa gaagctgaac tttcattgaa tagttttgaa acaacatcta    660
aagacagtat tccttgttcc aacaaatcaa taattatttc aataaattga atagtgtttg    720
gtattcttag aatcaactcc aactcaccaa                                     750
```

<210> SEQ ID NO 38
<211> LENGTH: 679
<212> TYPE: DNA
<213> ORGANISM: Artificial
<220> FEATURE:
<223> OTHER INFORMATION: PCR amplicon

<400> SEQUENCE: 38

```
gccatcaggc tgtttgtaga aagtaacctt tgccacaacg ctcctcctaa agttttactc      60
aacaaatcct atgtctataa ttatatcggc atctacacca aggcctgaac accccttttga    120
caaatataaa tgcaaatcct agctgatcgt aatcactttt tcgattttct ttacaaattc    180
aataaactga ttttggtctt gaagaatacc aagcttttca tattcaccgg taaagagcca    240
ttgagggttt tccccagttg tctgtatctc catgataaaa cttgttcctt ttgtgttgat    300
ctcttcatct tcctgaattt cataatgatg tgtaattaat ttttttcaaag agtggctgtc    360
ctttatttct tttgtataaa atgataatcc ctgctcctca taccgcttta gttcaaagcc    420
attatccact aaaaagttta agttgttttg atttaatgta agcaaaattt atttccccttt    480
tcattaaaaac tgctgtttta ttcagattttt aaggcattca caagcttctc cctgcactca    540
tcgcaaacgt gtattatgct tgtcgcatat ggcaaacaaa tactatatac accttttcaat    600
cttctattcc cacatccatt gcaatgttta gtttcttctg ttttatgtac actaattttta    660
tctctatcca aactgcgcc                                                  679
```

<210> SEQ ID NO 39
<211> LENGTH: 743
<212> TYPE: DNA
<213> ORGANISM: Artificial
<220> FEATURE:
<223> OTHER INFORMATION: PCR amplicon

<400> SEQUENCE: 39

```
cagatgaagt tggtggtgtt tcttcttcga tggtagactc aatgaagtaa actggagtat      60
```

```
ttgtgaatgt aacggagatg ttttcgttaa gtttgtgtgt ggtgaattga cctatatcaa      120
cgtttgattg gatgtactta tcaatatcaa gttcttttt tgtgttgtca acattcggta       180
atattgtttt gctgttagtt tcaacataat atttttgtcaa agccttttcg gtgaattcgt     240
ttttagaatt gaactgatct actgcatttt ctaattgttc ttcatcttga ggattagaga     300
tttttagtgt aactaaaagc aaatcttgat attcttgaat tgaattgatc tcattctttt    360
cgcttgcact tgctgtttta cttccagtgg caaatgtgaa agatgacaga attaacacga     420
aacccaaaat agaaaaagt gttttttaa atttccccat agtaacagct ccttttttga       480
ttgataatag agccttctat gttgattaaa cctgttgtag gcattttata atatgtccct     540
cctttcaatt agaaccataa catataatct atgtccaatt ctatacattt tagcaatttt     600
aaggtaatat tatttactca taagtgaatg acatcccaaa atcacaatag gacatataaa     660
ctattccctt tctagtgaag ggaaaataat attgatatat tagagagcca tttttataac    720
aatagatagc aggtaaaggc acg                                              743

<210> SEQ ID NO 40
<211> LENGTH: 687
<212> TYPE: DNA
<213> ORGANISM: Artificial
<220> FEATURE:
<223> OTHER INFORMATION: PCR amplicon

<400> SEQUENCE: 40
atgcggctag acatggatat gttcgtttaa caatgaaatg caactcccct tatgcataca       60
gtcgaaacac aagtacccat tcctttgata tatcatcaga aatgaaaatc attgaactcc     120
ataataaagg cgatgttgcg atttacccca ctgttgaaat tcttaaaatt ggcgatggcg     180
atgtgaaaat cgagaaccta agtgattata ctgccccctt tattttcagc aatctaaaag    240
acagagaaat tgttaaagtg aatggcgtca aagaaacaat tgaatcgtct ttatatggga    300
atgaaagata tgatgatttt aatgacaatt atattaaatt ggattacgga aaaaaccgat    360
taaaagtgac cggaaaatgc aaactgagat tcactttcag atttaagtat cgataagaag    420
gtgaaaaatt gataactatt cgcaaggaca cagaaataaa aaacatacgc ttatcccttg    480
ctaagccaga caagactaaa atagccaaca ttgatgaagt tctgaatcca actgtaactt    540
taaatcatgg aagcagcgtt cacgaactct ccttctctat tccgcttaaa gcaacctatg    600
atggcataat taaagaaac catgttgtag atttactaaa accctggtac ctaattaaaa     660
cagcgttcta tgggcttacg atttggt                                          687

<210> SEQ ID NO 41
<211> LENGTH: 954
<212> TYPE: DNA
<213> ORGANISM: Artificial
<220> FEATURE:
<223> OTHER INFORMATION: PCR amplicon

<400> SEQUENCE: 41
tgtccctctt taggtgctat tgataaaatt ttaacccaat tgtaagtcca ctcgttgtat       60
gtccaaaatt caaattgctt ttttccataa acatttttcc ccaccatcgc atatctaaac     120
caattactgc cagttttttg aggttgaaaa actttatcgt ttttatttc ctcaaatgta      180 acaggaatca aggaagaaac gtatgctaac tgatcatctt catttagtgt cttaacataa    240
ctttcaacaa gactgcttgc ttcttttgat tccattttga ttttctttgt tttaagttta    300
```

```
ttctggatgt tttgttcgat tttctttgat ggttctttag taaactctat tatcttttgt        360
ttctcgtcat cgttaaattt atcccatgaa tcaggttgag caacgaattg cttagtgagc        420
tctttagctg aatttaacga tgctgcatgc gcagttgtca tattaaaacc tgcaagagat        480
acaatcgcta acactaatga tagaatcagc ttttcatat agacacactc cttatatatc         540
ttctgttttt tattgaaaaa ccctttcat ttttcgaatt tcttctcaaa tagcagaaca         600
acctagtgaa tagttttatc cggttccaaa aaataattaa gtgtgctcct cctccctcta        660
atgattagat caaaagctat gcaaggtta tgagtcagaa gaccctcaat accatatcac         720
ctcctaacgc aaccctacca cactcttatc tttcattaaa tagcttaact tccaaatgat        780
agtttatgac taaattgaaa aaaaacagaa atccgcaat gatttacgga accttctgtc         840
ttttgaaaat tgacctaacg tcatgttttt tggataaaaa gcttcttttg atgctgatta        900
ttcgccataa ccatgtaata agaagctatc tataaacatc ggctaaagtc ctga             954

<210> SEQ ID NO 42
<211> LENGTH: 496
<212> TYPE: DNA
<213> ORGANISM: Artificial
<220> FEATURE:
<223> OTHER INFORMATION: PCR amplicon

<400> SEQUENCE: 42
ccctctagct ctttcttctt cactttccag tcgtttggag gcagtcccctt accttgtttt        60 ttgaagagca tcattttgta cctagactct aaaagctgat aataaatgat aaccttatcg       120
tcttcctcca tatgcttcaa ggattcctta gcttttttaa gaagttgctc tgccaaatct       180
atctcacatt tcttaatagc aacatgaagt tcattcagag tattagctac tacctcgtgt       240
gcgatcgtac ccatttataa cccctctttt ctaaaatgtt tcgaattatt aaacaatata       300
acagacattt gcaatatttg gaataattta aaagtggttt tcggtaagtt ttcgtcatac       360
cgcaataacc ttttggggaa ggcatgctaa aaaagtccct atttctttta atcagtcggc       420
ctactgattg cattattcgc ttgaaataaa taaaagcggg ctccgaaaat ggagtaccca       480
ctctagaaat attggc                                                      496

<210> SEQ ID NO 43
<211> LENGTH: 31841
<212> TYPE: DNA
<213> ORGANISM: Bacillus subtilis

<400> SEQUENCE: 43
gacgctcttc gcaagggtgt cttttttgc cttttttcg gttttgcgc ggtacacata           60 gtcatgtaaa gattgtaaat tgcattcagc aataaaaaaa gattgaacgc agcagtttgg       120
tttaaaaatt tttattttc tgtaaataat gtttagtgga aatgattgcg gcatcccgca       180 aaaatattg ctgtaaataa actggaatct tccggcatcc cgcatgaaac ttttcaccca       240
tttttcggtg ataaaaacat tttttcatt taaactgaac ggtagaaaga taaaaaatat       300
tgaaaacaat gaataaatag ccaaaattgg tttcttatta gggtggggtc ttgcggtctt       360
tatccgctta tgtaaacgc cgcaatgctg actgacggca gcctgcttta tagcggcca         420 tctgttttt gattggaagc actgcttttt aagtgtagta ctttgggcta tttcggctgt       480
tagttcataa gaattaaaag ctgatatgga taagaaagag aaaatgcgtt gcacatgttc       540
actgcttata aagattaggg gaggtatgac aatatgaaa taacttttta ccctttaacg       600
gatgcacaaa aacgaatttg gtacacagaa aaatttatc ctcacacgag catttcaaat       660
```

```
cttgcgggga ttggtaagct ggtttcagct gatgcgattg attatgtgct tgttgagcag    720
gcgattcaag agtttattcg cagaaatgac gccatgcgcc ttcggttgcg gctagatgaa    780 aacgggagc  ctgttcaata tattagcgag tatcggcctg ttgatataaa acatactgac    840
actactgaag atccgaatgc gatagagttt atttcacaat ggagccggga ggaaacgaag    900
aaacctttgc cgctatacga ttgtgatttg ttccgttttt ccttgttcac cataaaggaa    960
aatgaagtgt ggttttacgc aaatgttcat cacgtgattt ctgatggtat ctccatgaat   1020
attctcggga atgcgatcat gcacatttat ttagaattag ccagcggctc agagacaaaa   1080
gaaggaatct cgcattcatt tatcgatcat gtttttatctg aacaggaata tgctcaatcg   1140
aagcggtttg aaaaggacaa ggcgttttgg aacaaacaat ttgaatcggt gcctgaactt   1200
gtttccttga acggaatgc  atccgcaggg ggaagtttag atgctgagag gttctctaaa   1260
gatgtgcctg aagcgcttca tcagcagatt ctgtcgtttt gtgaggcgaa taaagtcagt   1320 gttcttcgg  tatttcaatc gctgctcgcc gcctatttgt acagggtcag cggccagaat   1380
gatgttgtga cgggaacatt tatgggcaac cggacaaatg cgaaagagaa gcagatgctt   1440
ggcatgtttt tttctacggt tccgcttcgg acaaacattg acggcgggca ggcgttttca   1500
gaatttgtca agaccggat  gaaggatctg atgaagacac ttcgccacca aaagtatccg   1560
tataatctcc taatcaacga tttgcgtgaa acaaagagct ctctgaccaa gctgttcacg   1620
gtttctcttg aatatcaagt gatgcagtgg cagaaagaag aggatcttgc cttttttgact  1680 gagccgattt tcagcggcag cggattaaat gatgtctcaa ttcatgtaaa ggatcgatgg   1740
gatactggga aactcaccat agattttgat taccgcactg atttattttc acgtgaagaa   1800
atcaacatga tttgtgagcg catgattacc atgctggaga acgcgttaac gcatccagaa   1860
catacaattg atgaattaac actgatttct gatgcggaga agagaagct  gcttgcgagg   1920 gccggcggta atctgtgag  ctaccgtaag gacatgacga taccagagct gttccaagaa   1980
aaggctgaac tgctttctga tcatccagcg gttgtatttg aagatcgcac attgtcctat   2040
cgaacgttac atgagcaatc tgcacgcatc gccaatgtgc tgaaacagaa aggggttggc   2100
ccggacagtc ctgtcgcggt tttgattgaa cgctctgaac ggatgattac agctatcatg   2160 ggaatttta  aagccggcgg agcctatgtg ccgattgatc cgggttttcc tgctgagcgc   2220
attcaatata ttttggagga ctgcggggcg gatttcatcc tgactgaatc gaaggttgcg   2280
gcgcctgaag ccgatgctga gctgattgac ttagatcagg cgattgagga aggtgcagaa   2340
gaaagcctga atgcagatgt gaacgctcgg aaccttgcct acattatta  cacatcggga   2400 acaaccggac gcccgaaagg cgttatgatc gagcatcgcc aggttcatca tttggttgaa   2460
tctctgcagc agacgattta tcaaagcggc agccaaaccc tgcggatggc attgcttgcg   2520
ccgttccact tgatgcgtc  agtgaagcag atcttcgcgt cgcttctttt gggccaaacc   2580
ctttatatcg taccgaagaa aacagtgacg aacgggccg  cccttactgc atattatcgg   2640
aagaacagca ttgaggcgac ggacggaaca ccggctcatt gcaaatgct  ggcagcagca   2700 ggcgattttg aaggcctaaa actgaagcac atgctgatcg gaggagaagg cctgtcatct   2760 gttgttgcg  acaagctgct gaagctgttt aagaagccg  gcacagcgcc gcgtttgact   2820
aatgtgtacg gccgactga  aacgtgcgtt gacgcgtctg ttcatccggt tatccctgag   2880
aatgcagttc aatcagcgta tgtgccgatc gggaaagcgc tggggaataa ccgcttatat   2940
attttggatc aaaaaggccg gctgcagcct gaaggcgtgg cgggtgagct ttatatcgcg   3000
```

```
ggagacggtg tgggccgagg ctatttacat ttgcctgaat taacggaaga gaagttttta    3060
caagatccat tcgtgccggg cgatcgcatg taccggaccg gggacgtggt gcgctggctt    3120
ccagatggaa caatcgaata tttaggcaga gaggatgacc aggtcaaagt ccgcggatac    3180
cggattgagc ttggggaaat tgaagccgtg attcagcagg cgccagacgt tgcaaaagcc    3240
gttgttttgg cacgccctga cgaacaggga aatcttgagg tttgcgcata tgttgtgcag    3300
aagcctggaa gcgaatttgc gccagccggt tgagggagc atgcggccag acagcttcct     3360
gactatatgg tgccggctta ctttacagaa gtgacagaaa ttccgcttac accaagcggc    3420
aaagtcgacc gccgcaagct gtttgcacta gaggtgaagg ctgtcagcgg cactgcctat    3480
acagcgccgc gaaatgagac tgaaaaagca atcgcagcca tttggcagga cgtgctgaac    3540
gttgagaagg cggggatctt tgacaatttc tttgaaactg gcggacattc attaaaagcc    3600
atgacccttt taacaaagat tcataaggaa acaggcattg agattccgct tcaattttg     3660
tttgagcatc cgacgattac ggctcttgca gaggaagctg atcacagaga aagcaaagct    3720
tttgcggtga ttgaacctgc tgaaaaacag gagcattacc cgctttcatt ggcacagcag    3780
cgaacatata tcgtcagcca gttcgaggat gcgggagtcg gctataacat gccagcagca    3840
gcaattctgg aagggccttt agatattcaa aagctggagc gcgcatttca gggattaatc    3900
cgacgccacg agtcattgag aacatcattt gttcttgaaa acagcacgcc gagacagaaa    3960
attcacgata gcgttgattt caacatcgaa atgattgaaa gaggcggccg ctcagatgag    4020
gcaattatgg cttcattcgt tcggacattt gatttggcga agctccgct gttcagaatc     4080
ggtttgctgg ggcttgaaga gaaccgtcat atgctgctgt ttgacatgca ccatttgatt    4140
tctgacggtg tatccattgg cattatgctg gaggagttag cacgcattta taaaggcgaa    4200
cagcttcctg atcttcgtct ccagtataag gactacgctg tatggcaaag cagacaggct    4260
gctgaagggt acaagaagga ccaggcttat tggaaggaag tctttgcagg cgagctcccg    4320
gtgcttcagc ttctgtccga ttacccaaga ccacctgttc aaagctttga aggggatcgg    4380
gtgtcaatca agctggatgc gggggtaaag gatcgcctca atcgtttggc tgaacaaaac    4440
ggcgccactt tatatatggt gatgcttttcc gcttactata cgcttttgtc aaagtatacg    4500
gggcaggatg acatcattgt cgggacaccg tcagcgggca gaaatcactc cgatacagag    4560
ggcattatcg ggatgttcgt caatacgctt gcgattcgca gtgaggtgaa gcagaatgag    4620
acgtttaccc aattgatctc gcgtgtccgc aaacgggtgc tggatgcctt ttctcatcag    4680
gactatccgt ttgagtggct tgttgaagat ttgaacatcc cgcgtgatgt tagcaggcat    4740
ccgctgtttg acacgatgtt cagccttcaa aacgcgacag agggcattcc ggctgtcggc    4800
gatctttcct tgtctgttca agagaccaat ttcaagattg ccaaatttga tttgacggtg    4860
caggcgagag aaaccgatga aggcattgag attgatgtgg attacagcac aaagctgttt    4920
aaacaaagca cggcagacag gctgcttacg cattttgcgc gtttgcttga agatgctgcg    4980
gctgatccag agaagccgat ttctgagtat aagcttcttt ctgaagagga ggctgcttcg    5040
caaattcagc agtttaaccc gggcagaaca ccttatccga agataaaac aattgttcag     5100
ctgtttgagg agcaagcggc gaatacgcca gaccacactg cgcttcaata tgaaggcgaa    5160
tcactcactt atcgtgaact gaatgaacgg gccaatcgtt tagcccgcgg cattctttct    5220
cttggagctg gcgaaggcag aactgcggct gtcttatgcg agcggtcaat ggatatgatt    5280
gtgtcgatct tggcagtatt aaaatcaggt tcggcttatg ttccgatcga tccggaacat    5340
ccgattcagc ggatgcagca tttcttccgt gacagcggag caaaggtgct tctcactcag    5400
```

```
aggaaattaa aggctttggc ggaagaagcg gaatttaagg gcgttatcgt gctagccgat    5460
gaggaagaaa gctatcatgc cgatgcgcga aatctcgcac tgcctcttga ttctgcagca    5520
atggccaacc tgacgtatac ttccggaacg actggaacac ctaaggggaa tatcgtgaca    5580
catgccaata ttctccgcac ggtgaaggaa acgaattatc tcagcattac agaacaggat    5640
acgattctcg gtctttccaa ttacgtgttt gacgcgttta tgttcgatat gttcggctct    5700
ttgttaaacg gagccaagct ggtgctgata ccgaaggaaa ccgttttgga catggctcgc    5760
ctgtcccgcg tcattgaacg ggagaacatc agcattctca tgattacaac cgctttgttc    5820
cacttgcttg tggacttgaa tccggcatgc ttgtcaacgc ttcgcaagat tatgtttggc    5880
ggggaacggg cttcggttga gcatgtcaga aaagctttgc aaacggttgg aaagggcaag    5940
ctccttcata tgtatggacc gtctgaaagc acggttttcg cgacgtatca tccggttgat    6000
gaattggagg agcacacgct gtctgttccg attggaaaac cggtcagcaa tacggaagta    6060
tacattcttg accgtacggg acacgtgcag cctgccggga ttgccggaga gctttgcgtc    6120
agcggcgaag gactcgtgaa aggctattac aaccgtccag aactgactga ggagaaattt    6180
gttccccatc cgtttacatc cggcgaacgc atgtataaaa cgggagacct tgcgagatgg    6240
ctgccgaatg gcgacatcga atttatcggg cgaatcgacc atcaggtgaa gattcgcgga    6300
cagcgcatcg agcttggaga aatcgaacat cagctgcaaa cccatgatcg tgttcaggaa    6360
agtgttgtgc ttgccgttga tcaaggagcg ggagataaac tgttgtgtgc ttactatgtc    6420
ggagaaggag acatctcatc acaagagatg agagagcatg ctgcgaagga cttgccggca    6480
tatatggttc ctgcggtgtt tatccaaatg gacgagctgc cgctgacagg gaacggaaaa    6540
attgaccgga gagcgctgcc gattcctgat gccaacgttt caagaggtgt ttcatatgtt    6600
gcgccacgca atggaacgga acaaaaagtc gcggacattt gggcacaggt acttcaggca    6660
gaacaagtcg gcgcttatga ccacttcttt gacattggcg acattcatt agcaggcatg    6720 aagatgcttg ccttggttca tcaggaactg ggcgttgagc tgtcactcaa ggatctcttc    6780
cagtcaccga cggttgaggg cttggcacag gtgattgcct ctgctgaaaa agggacagcc    6840
gcaagtatca gcccggcaga gaaacaagat acgtatcctg tttcttcacc gcaaaaacgg    6900
atgtacgtgc ttcagcagct tgaggatgcg caaacgagct ataacatgcc ggcggttctg    6960
cgcctgacag gtgagcttga tgttgaaagg cttaacagcg tcatgcagca gttaatgcag    7020
cgtcatgaag ccttgagaac cacgtttgaa ataaagatg gagaaacggt gcagcggatc    7080
tgggaagagg ctgagtgcga gatagcctat ttcgaagccc cggaagaaga gacagagcgg    7140
atcgtttctg agtttattaa gcctttcaaa atcgaccaac ttccactgtt cagaataggg    7200
cttatcaagc attcagacac tgagcatgtg ctgctgttcg atatgcatca tattatttct    7260
gatggtgcat ctgtcggtgt gctgattgag gagctttcaa agctgtacga cggagaaacc    7320
cttgagccgc tccgtattca atataaggat tatgccgtgt ggcagcagca gttcattcag    7380
tctgagcttt acaagaagca agaagagcat tggctgaagg agctggacgg agagctgccg    7440
gtgctgacgc ttccgactga ttacagtcgg cctgccgttc aaacatttga gggagaccgc    7500
attgcatttt cattagaagc aggcaaagct gatgctctgc gcaggcttgc aaaagaaacg    7560
gattccacgc tttacatggt gcttctggct tcatacagtg cgttttatc aaaaattagc    7620 gggcaagacg atatcatcgt cggttcacct gtggccggac gatctcaagc ggacgtcagc    7680
cgcgtcatcg gaatgttcgt caatacattg gcgctgcgca cgtatccgaa gggtgaaaag    7740
```

```
acgtttgctg actatcttaa cgaagtgaaa gaaacggcac tcagcgcttt tgatgcgcag   7800
gattacccac ttgaggattt gatcggaaat gttcaggttc agcgtgacac aagcagaaat   7860
ccgttattcg atgcagtttt ttcaatgcaa aatgcgaata taaaggattt aacaatgaaa   7920
gggattcagc ttgagccgca tccgtttgaa cggaaaacag ccaagtttga cctcacgctg   7980
acggctgacg aaaccgacgg agggcttaca ttcgtactcg aatacaatac agctctgttt   8040
aagcaggaaa cgattgaacg atggaagcaa tattggatgg agcttttaga tgcagttact   8100
gggaacccga accagccgct ttccagcctg tcactggtca ccgagacaga aaagcaagcg   8160
cttcttgagg catggaaggg caaagcgctg cctgtgccga cagacaaaac ggttcatcag   8220
ctattcgaag agactgccca gcgccacaaa gaccgcccgg ctgtcacata caacggccag   8280
tcttggacgt acggcgagct gaatgcgaag gcaaaccgtc tcgcgcggat tctgatggac   8340
tgcggcatca gcccggatga ccgcgtcggc gttctcacga agccgtcgct tgaaatgtcc   8400
gccgcggtgc tcggcgtctt gaaagccgga gcggcgtttg tgccgattga tcctgactat   8460
ccggatcagc ggattgagta tattttacag gacagcggcg cgaagcttct cttgaaacag   8520
gaaggcattt cagtgccgga cagctatacg ggagatgtca ttcttctcga cggaagccgc   8580
acgattctaa gcctgccgct tgatgaaaac gacgaggaaa atccagaaac cgctgtaacc   8640
gcggagaact tggcgtacat gatttacacg tctggaacga ccggacagcc gaagggtgtc   8700
atggtcgagc accatgcgct tgtgaacctg tgcttctggc accacgacgc gttcagcatg   8760
acagcggagg accgcagtgc gaagtacgcg ggctttgggt tcgacgcttc catttgggag   8820
atgttcccga cctggacgat cggtgccgaa cttcacgtca ttgaggaagc gatccgcctc   8880
gatatcgtcc gcctgaacga ttattttgaa acgaacggcg taacgatcac gttcctgccg   8940
acacagcttg cggaacagtt catggagctt gagaacacat cacttcgcgt attgcttact   9000
ggaggagaca agctgaagcg cgcagtgaaa aagccgtaca cactcgtcaa taactacggg   9060
ccgacagaga atacggtcgt tgccacaagc gcagaaatcc atccggagga aggctcgctt   9120
tccatcggaa gggccattgc caatacgaga gtatacattc tcggcgaggg caatcaggtg   9180
cagccggaag gcgtagccgg agagctttgc gtggcggggc gcggactggc acgcggctat   9240
ctgaatcgag aagacgaaac cgcgaagcgg tttgtcgctg atccgtttgt gccgggtgag   9300
cgcatgtacc gcaccggcga tttggtgaaa tggacgggcg gcggcatcga atacatcggc   9360
cggatcgacc agcaggtcaa ggtccgcggc taccggatcg agctctcaga aattgaagtc   9420
cagctcgccc agctttctga ggtgcaggat cggcggtga cagctgtcaa agataaaggc   9480
ggcaacacag cgatcgcggc gtatgtcaca ccggaatcag ctgacataga agcactgaaa   9540
tcagcactga aggaaaccct gccggattac atgatcccgg cgttctgggt gacgctgaac   9600
gagcttccgg ttacggcaaa cggcaaagtg gaccgcaaag ccttgcctga gccggacatc   9660
gaagcgggaa gcgagaata caaagcgccg acgaccgaca tggaagagct gcttgccggc   9720
atctggcagg acgtgcttgg aatgtctgaa gtcggtgtca ccgacaattt cttctcgctt   9780
ggcggagatt ccatcaaagg aattcaaatg gcgagccgct tgaaccagca cggctggaag   9840
ctggaaatga aagatctctt ccagcacccg acgatcgaag agctcaccca gtacgtagag   9900
cgtgccgaag gcaaacaggc agaccaaggc ccggtggagg gcgaagtcat cctgacgccg   9960
atccagcgct ggttctttga aaagaacttc acgaacaagc accactggaa ccaatctgtg  10020
atgcttcacg ccaagaaggg ctttgatcct gaacgggtgg agaaaacatt gcaggcgctg  10080
atcgagcatc atgacgcgct ccgcatggtc tatcgtgagg acaggaaga cgtcattcaa  10140
```

```
tacaacagag gtcttgaagc tgcttcagct caattggagg tcatccagat tgagggccaa    10200
gctgcagatt acgaagaccg aatagagaga gaagcggagc gtttgcaaag cagcatcgac    10260
ttgcaggaag gcggcttgtt aaaagcaggc ttgttccaag cggaagacgg agatcacttg    10320
cttcttgcca ttcaccactt agtggttgac ggcgtgtcgt ggcggatttt actggaggat    10380
ttcgccgcgg tatatacaca gcttgagcaa ggcaatgaac cggttctccc gcagaaaaca    10440
cattcatttg cagagtatgc agagagattg caagacttcg cgaactccaa agccttttg     10500 aaagaaaaag agtattggag acagcttgaa gaacaagctg ttgcggcaaa gcttccgaaa    10560
gaccgcgaat ctggtgatca gcgaatgaaa catacaaaga caattgaatt ctcgctgact    10620
gctgaagaga cagaacagct caccacaaag gtgcatgagg catatcacac agaaatgaat    10680
gatattttgc tgacggcatt cggattggca atgaaggagt ggacgggtca agatcgagta    10740
agtgttcatt tagaggggca tggacgtgaa gaaatcatag aagacctgac catttctcgc    10800
acagtcggct ggtttacaag tatgtaccca atggtgctcg atatgaagca tgcggatgat    10860
ctgggctacc agctgaagca aatgaaagaa gatatcagac atgtgccgaa taagggagtc    10920
ggatacggca ttctgcgcta tctgacggca ccggaacata aagaagatgt ggcgttctcg    10980
attcagccgg atgtcagctt caactattta ggtcagtttg acgaaatgtc ggatgcaggt    11040
ttgtttacga gatcagagct gccatcagga cagtcattaa gccctgaaac agaaaaaccg    11100
aatgcgctgg atgttgtcgg atatatcgaa aacggaaaac tgacgatgtc actggcctat    11160
cattctcttg aatttcatga aaaaacagta caaacattca gtgacagctt taaagcgcat    11220
cttctcagaa tcattgaaca ttgcctatct caagacggta cggaactgac cccgagtgat    11280
cttggtgacg acgatttgac gctggatgag ctggataaat taatgaaaat tttctaatag    11340
aggtggcata tgagcaaaaa atcgattcaa aaggtgtacg cactgacacc aatgcaggag    11400
ggaatgctgt atcatgcgat gcttgatccg cattcttcct cgtacttcac acaattagag    11460
cttgggattc acggcgcttt tgatcttgaa atctttgaga aaagcgtcaa tgaactgatt    11520
cggtcatacg atattctccg tacggtattt gtgcatcagc agctgcaaaa accgcgtcag    11580
gtcgtgttag cggaacgcaa aacaaaggtg cattatgagg atatcagtca tgcagacgag    11640
aaccgccaga aggagcacat tgagcgttac aaacaagacg ttcagcgcca aggctttaac    11700
ctggcaaaag acatattgtt caaggtggcg gttttccgcc ttgctgcaga tcagctgtat    11760
cttgtctgga gcaatcatca tattatgatg gacggctgga gcatggcgt cctcatgaaa    11820 agcctgttcc aaaactatga agcgctcaga gcaggaagga caccggcaaa cggtcaaggc    11880
aagccttact ccgactacat caaatggctt ggaaaacagg acaatgaaga agcggagagc    11940
tactggagcg agcgcttggc gggttttgaa cagccaagcg tgctcccggg ccgcctgcct    12000
gtgaaaaaag acgaatacgt caataaagaa tattcctta catgggacga aacactggtt     12060
gcccgtattc agcaaaccgc aaatctccat caagtgacag gcctaaccta tttcaggcc     12120 gtttggggca ttgttctcag caaatacaac tttacggatg atgtggtctt cggaacggtc    12180
gtctcgggcc gaccgtctga atcaacggc atcgaaacga tggcgggggct gtttatcaac    12240 accattccag tgcgggtgaa agttgaacga gatgctgcat tcgctgatat tttcacagct    12300
gttcagcagc atgcagtaga ggcagagcgt tacgattacg tgccgctcta tgagattcaa    12360
aaacgctcag ctcttgatgg caatctctta aaccatctgg tcgcgtttga aaattatccg    12420
cttgatcaag agcttgaaaa cggcagcatg gaagaccgcc tcgggttttc aattaaggta    12480
```

```
gaaagcgcat ttgaacaaac gagcttcgat ttcaacctga ttgtgtatcc gggcaaaacg   12540
tggaccgtca aaattaaata taacggagcc gcctttgatt ccgcttttat cgaacggaca   12600
gcggagcacc ttacccgcat gatggaagca gctgtcgatc agccggccgc ttttgtgcgt   12660
gagtacgggt tgttggaga cgaagagcag cggcaaattg tcgaggtgtt taacagcacg    12720
aaagccgaac tccctgaagg aatggctgtt caccaagtgt ttgaagagca agcgaaacgg   12780
acgccggcga gcactccgt cgtatatgaa ggaaccgagc tgacgtaccg cgagctgaat    12840
gcagcggcta accgtctggc gagaaagctt gtcgaacaag gccttcaaaa aggggaaaca   12900
gcagcgatta tgaacgatcg atcagtagaa accgttgtcg gcatgctggc tgtgttaaaa   12960
gcaggcgccg catatgtgcc gcttgatcca gcgcttccgg gggatcgtct tcgtttcatg   13020
gcagaggaca gctccgttcg aatggttttg accggaaatt cttatacagg gcaggcacat   13080
cagctgcagg tgccggttct tacactggac ataggcattg aagatggcga agctgacaat   13140
ctcaacctgc catccgcccc gtctgatttg gcgtacatca tgtacacatc cggttcaacg   13200
ggcaaaccga aaggcgtcat gatcgaacat aaaagcattc tgcgcctcgt caaaaatgcc   13260
gggtacgttc ctgttactga agaggaccgc atggcgcaaa caggggcagt cagctttgat   13320 gccgaacgt ttgaggtatt cggcgcactg ctgaatggcg cagcgcttta tccggtcaaa    13380
aaagagacac tgcttgatgc gaaacaattt gctgcattcc tgcgtgagca aagcatcaca   13440
accatgtggc tgacatcacc tttattcaac cagcttgcag caaaggatgc gggtatgttc   13500
ggcacactgc gccatttaat catcggcgga gacgcccttg tcccgcatat tgtcagcaaa   13560
gtaaaacagg catcgccgtc gctttcattg tggaacggat acggcccgac agaaaacacg   13620
acgttttcaa ccagttttct gatcgaccgc gagtatggcg gctctatccc aatcgggaag   13680
ccgatcggaa attccactgc ctacatcctg gatgagcagc aatgcctgca gccaatcggc   13740
gcgcctggtg agctttgcgt aggcggaatc ggtgtagcgc gtgggtatgt caatctccct   13800
gagctgacag agaagcaatt tctcgaagat ccgttcagac cgggtgagag aatttatcgc   13860
actggtgact tggcaagatg gctgccggac ggcaatatcg aattttttagg cagaattgac   13920 aatcaagtga aggtgcgcgg cttccgaatt gagcttggcg aaattgaaac aaaactgaac   13980
atggctgcac atgtgacaga ggctgcggtg atcatccgca agaacaaagc ggatgaaaat   14040
gaaatttgcg cgtactttac ggcggaccgt gaagtggctg tgagcgagct gagaaaaaca   14100
ctgtctcagt cttttgcctga ctatatggtc cctgcccacc tgattcaaat ggacagtctg   14160
ccgctcacgc caaacgggaa aatcaacaaa aaagaactgc ctgtaccgca atcagaagcc   14220
gtgcagccgg aatacgcagc accagaaaca gagagtgaaa agaaattagc ggagatctgg   14280
gaaggaatac tcggcgtcag agcaggcgtt accgataact tctttatgat cggcggccat   14340
tctttgaaag cgatgatgat gacggcgaaa attcaagagc attttcataa ggaagttccg   14400
ataaaagtgc tttttgaaaa gccgactatt caagaactgg cactgtattt ggaagagaac   14460
gaaagcaagg aggagcagac gtttgaaccg atcaggcaag catcttatca gcagcattat   14520
cctgtatccc cggcccagcg gagaatgtat atcctcaatc agcttggaca agcaaacaca   14580
agctacaacg tccccgctgt acttctgctg gaggagaag tagataaaga ccggcttgaa    14640
aacgcgattc agcaattaat caaccggcac gaaatcctcc gtacatcgtt tgacatgatc   14700
gacggagagg ttgtgcaaac cgttcataaa aacatatcgt tccagctgga ggctgccaag   14760
ggacgggaag aagacgcgga agagataatc aaagcatttg ttcagccgtt tgaattaaac   14820
cgcgcgccgc tcgtccgttc gaagcttgtc cagctggaag aaaaacgcca cctgctgctc   14880
```

```
attgatatgc atcatattat tactgacgga agttcaacag gcattctaat cggtgatctt    14940
gccaaaatat atcaaggcgc agatctggaa ctgccacaaa ttcactataa agattacgca    15000
gtttggcaca aagaacaaac taattatcaa aaagatgagg aatactggct cgatgtcttt    15060
aaaggcgaac tgccaatact ggatcttccc gcggatttcg agcggccagc tgaacggagc    15120
tttgcgggag agcgcgtgat gtttgggctt gataagcaaa tcacggctca aatcaaatcg    15180
ctcatggcag aaacagatac gacaatgtac atgttttgc tggcggcgtt caatgtactc     15240
ctttccaagt acgcgtcaca ggatgatatc attgtcggct cgccgacagc tggcagaaca    15300
catcctgatc tgcaaggtgt gccgggtatg tttgtcaaca cggtggcact cagaacggca    15360
ccagcgggag ataaaacctt cgcgcaattc cttgaagagg tcaaaacagc cagccttcaa    15420
gcattcgagc accagagcta tccgcttgag gagctgattg aaaagcttcc gcttacaagg    15480
gatacaagca gaagtccgct gttcagcgtg atgttcaaca tgcagaatat ggagattcct    15540
tcattaagat taggagattt gaagatttcc tcgtattcca tgcttcatca tgttgcgaaa    15600
tttgatcttt ccttggaagc ggtcgagcgt gaagaggata tcggcctaag ctttgactat    15660
gcgactgcct tgtttaagga cgagacgatc cgccgctgga gccgccactt tgtcaatatc    15720
atcaaagcgg ccgcggctaa tccgaacgtt cggctgtctg atgtagatct gctttcatct    15780
gcagaaacgc tgctttgct agaagaaaga catatgactc aaattaccga agcaaccttt     15840
gcagcacttt ttgaaaaaca ggcccagcaa acacctgacc attctgcggt gaaggctggc    15900
ggaaatctgt tgacctatcg cgagcttgat gaacaggcga accagctggc gcatcatctt    15960
cgtgcccaag gggcaggaaa tgaagacatc gtcgcgattg ttatggaccg gtcagctgaa    16020
gtcatggtat ccattctcgg tgtcatgaag gcggggcag ctttccttcc gattgatcct     16080
gatacacctg aagaacgaat ccgttattca ttagaggaca gcggagcaaa atttgcggtc    16140
gtgaatgaaa gaaacatgac ggctattggg caatatgaag ggataattgt cagccttgat    16200
gacggtaaat ggagaaatga agcaaggag cgcccatcat ccatttccgg gtctcgcaat      16260
cttgcatacg tcatttatac gtccggtacg accggaaagc caagggcgt gcagattgag      16320
catcgtaatc tgacaaacta tgtctcttgg tttagtgaag aggcgggcct gacggaaaat    16380
gataagactg tattgctttc atcttacgca tttgaccttg gctatacgag catgttccct    16440
gtacttctgg gcggggcga gctccatatc gtccagaagg aaacctatac ggcgccggat     16500
gaaatagcgc actatatcaa ggagcatggg atcacttata tcaagctgac accgtctctg    16560
ttccatacaa tagtgaacac cgccagtttt gcaaagatg cgaactttga atccttgcgc     16620
ttgatcgtct tgggaggaga aaaaatcatc ccgactgatg ttatcgcctt ccgtaagatg    16680
tatggacata ccgaatttat caatcactac ggcccgacag aagcaacgat cggcgccatc    16740
gccgggcggg ttgatctgta tgagccggat gcatttgcga acgcccgac aatcggacgc     16800
ccgattgcga atgccggtgc gcttgtctta aatgaagcat tgaagcttgt gccgcctgga    16860
gcgagcggac agctctatat cacgggacag gggctcgcga gagggtatct caacaggcct    16920
cagctgacag ccgagagatt tgtagaaaat ccatattcgc cgggaagcct catgtacaaa    16980
accggagatg tcgtacgaag actttctgac ggtacgcttg catttatcgg ccgggctgat    17040
gatcaggtga aaatccgagg ctaccgcatt gagccgaaag aaattgaaac ggtcatgctc    17100
agcctcagcg gaattcaaga agcggttgta ctagcggttt ccgagggcgg tcttcaagag    17160
ctttgcgcgt attatacgtc ggatcaagat attgaaaaag cagagctccg gtaccagctt    17220
```

```
tccctaacac tgccgtctca tatgattcct gctttctttg tgcaggttga cgcgattccg    17280
ctgacggcaa acggaaaaac cgacagaaac gctctgccga agcctaacgc ggcacaatcc    17340
ggaggcaagg ccttggccgc accggagaca gcgcttgaag aaagtttatg ccgcatttgg    17400
cagaaaacgc ttggcataga agccatcggc attgatgaca attttttcga tttaggcggc    17460
cattcattaa aagggatgat gctgattgcc aacattcagg cggaattgga gaaaagcgta    17520
ccgcttaaag cactgttcga gcagccgaca gttcgccagc tggcggctta tatggaggcg    17580
tctgctgttt caggcggcca tcaagtactc aaaccggctg acaagcagga tatgtatcca    17640
ttgtcatccg cacagaaacg aatgtacgtg ctcaatcagc ttgaccgcca gacgataagc    17700
tacaacatgc catctgttct tctaatggaa ggagagcttg atatttcgcg cctgcgcgac    17760
tcactcaatc agcttgtgaa ccgtcacgaa tcattgcgga cgtcatttat ggaagctaat    17820
ggtgagcctg ttcagcgcat cattgagaag gcggaggttg atcttcatgt gtttgaagcc    17880
aaagaagacg aagcggacca aaagattaag gaatttatcc ggccattcga cttaaacgac    17940
gcaccgctca ttcgcgcagc tttgcttcga atagaagcga aaaaacattt gctgctttta    18000
gatatgcatc atatcatcgc agacggcgtc tcaagaggca tctttgtaaa agaattggcg    18060
ctgctttaca aaggagagca gcttccggag ccgacgcttc attataaaga tttcgccgtt    18120
tggcaaaatg aagctgagca aaaagaacgg atgaaggagc atgaggcgta ctggatgtca    18180
gttctttcag gcgagctgcc agagcttgat ctcccgctcg attatgcccg tccgcctgtg    18240
caaagcttta aaggagatac gatccgtttc cgtacgggaa gtgagacggc aaaggcggta    18300
gaaaaactgc ttgccgaaac cggaacgacc ttgcacatgg tgctccatgc tgtttttccac    18360 gtcttttaa gcaaaatttc cggacagcgg gatatcgtca tcggctccgt tactgccggc    18420
cggacgaatg ctgatgttca ggacatgccg ggaatgttcg tcaatacact tgccctgaga    18480
atggaagcga aagaacagca aacatttgcg gagcttttgg agctagcaaa gcagacgaac    18540
ctgtcagccc ttgagcatca ggagtatccg tttgaagatc tggttaatca gcttgatctc    18600
cctcgggata tgagccgaaa cccattgttt aatgtgatgg tgacgacaga aaaccctgat    18660
aaagaacagc ttacattgca aaatctgagc atttcacctt atgaggctca tcagggaact    18720
tctaagtttg atctgacact gggcggattt actgatgaaa atggcattgg cttgcagctc    18780
gaatatgcga cagatctgtt cgcaaaagaa acagctgaaa aatggagcga atacgttctg    18840
cggctactaa aggctgttgc ggataacccg aaccagccgc tttccagtct gttactggtc    18900
accgagacag aaaagcaagc gcttcttgag gcatggaagg gcaaagcgct gcctgtgccg    18960
acagacaaaa cggttcatca gctattcgaa gagactgtcc agcgccacaa agaccgcccg    19020
gctgtcacat acaacggcca atcttggacg tacggcgagc tgaacgcgaa ggcaaaccgc    19080
ctcgcccgga ttctgatgga ctgcggcatc agcccggatg accgcgtcgg cgttctcacg    19140
aagccgtcgc ttgaaatgtc cgccgcgtg ctcggcgtct tgaaagccgg agcggcgttt    19200
gtgccgattg atcctgacta cccggatcag cggattgagt atattttaca ggacagcggc    19260
gcgaagcttc tcttgaaaca ggaaggcatt tcagtgccgg acagctatac gggagatgtc    19320
attcttctcg acggaagccg cacgattcta agcctgccgc ttgatgaaaa cgacgaggga    19380
aatccagaaa ccgctgtaac cgcggagaac ttggcgtaca tgatttacac gtctggaacg    19440
accggacagc cgaagggtgt catggtcgag caccatgcgc ttgtgaacct gtgcttctgg    19500
caccacgacg cgttcagcat gacagcggag gaccgcagtg cgaagtacgc gggcttcggg    19560
ttcgacgctt ccatttggga gatgttcccg acctggacga tcggcgctga acttcacgtc    19620
```

```
attgatgaag cgatccgcct cgatatcgtc cgcctgaacg attattttga aacgaacggc    19680
gtaacgatca cgttcctgcc gacacagctt gcggaacagt tcatggagct tgagaacaca    19740
tcacttcgcg tcctcttgac cggaggagac aagctgaagc gggcagtgaa aaagccgtac    19800
acactcgtca acaactacgg gccgacagaa aatacggtcg ttgccacaag cgcagaaatc    19860
catccggagg aaggctcgct ttccatcgga cgggccattg ccaatacgag agtatacatt    19920
ctcggcgagg gcaatcaggt gcagccgaaa ggcgtagccg gagagctttg cgtggcgggg    19980
cgcggactgg cacgaggcta tctgaatcga gaagacgaaa ccgcgaagcg gtttgtcgct    20040
gatccgtttg tgccgggtga acgcatgtac cgcaccggcg acttggtgaa gtgggtgaac    20100
ggcggcatcg aatacatcgg ccggatcgac cagcaggtca aggtccgcgg ctaccggatc    20160
gagctctcag aaattgaagt ccagctcgcc cagctttctg aggtgcagga tgcggcggtg    20220
acagctgtca aagataaagg cggcaataca gcgatcgcgg cgtatgtcac accggaaaca    20280
gctgacatag aagcactaaa atcaacacta aaggaaaccc tgccggatta catgatcccg    20340
gcgttctggg tgacgctgaa cgagcttccg gttacggcaa acgcaaagt cgaccgcaaa    20400 gccttgcctg agccggacat cgaagcggga agcggagaat acaaagcgcc gacgaccgac    20460
atggaagagc tgcttgccgg catctggcag gacgtgcttg gaatgtctga agtcggtgtc    20520
accgacaatt tcttctcgct tggcggagat tccatcaaag gaattcaaat ggcgagccgc    20580
ttgaatcagc acggctggaa gctggaaatg aaagatctct tccagcatcc gacgatcgaa    20640
gagctcaccc agtacgtaga gcgtgccgaa ggcaaacagg cagaccaagg cccggtggag    20700
ggcgaagtca tcctgacgcc gatccagcgc tggttctttg aaaagaactt cacgaacaag    20760
caccactgga accaatcggt gatgcttcac gccaaaaagg gctttgatcc tgaacgggtg    20820
gagaaaacat tgcaggcgct gatcgagcat catgacgcgc tccgcatggt ctaccgcgag    20880
gaaaacgggg acatcgttca ggtgtataaa ccgatcggtg agagcaaggt cagcttcgaa    20940
atcgtggatc tgtacggctc cgatgaagag atgctgagaa gccagattaa gcttctcgcg    21000
aacaagctgc aaagcagtct cgatctgcga aacgggccgc ttttaaaggc ggagcaatat    21060
cgcacagaag ctggggatca cctgctcatt gctgtacacc atctcgtggt cgacggtgtg    21120
tcatggcgga ttttgcttga agactttgct tcaggctaca tgcaggctga aaagaagag    21180 agccttgtct tcccgcaaaa aacaaactcc ttcaaggatt gggcggaaga actggcggca    21240
ttcagccaat cagcgcatct tttacagcag gctgaatact ggtcgcaaat tgccgctgaa    21300
caggtttctc ctttacctaa ggattgtgaa acagagcagc ggatcgtcaa ggatacatca    21360
tctgtcctat gtgaattaac ggcagaagac actaagcatc ttttaacaga tgttcatcag    21420
ccatatggaa ctgaaatcaa cgatattctt ctcagcgcgc tcggtttgac aatgaaagaa    21480
tggacaaagg gggccaaaat tggcattaac cttgagggac acggccggga ggacattatc    21540
ccgaatgtga atatctccag aacggtcggc tggtttacgg cacaataccc tgttgtgctc    21600
gacatatctg acgcagatgc ctcagctgtg atcaaaacag tcaaagaaaa cctgcgccgc    21660
attccggaca aaggtgttgg ctacggcatt cttcgttatt tcacagaaac agcggaaaca    21720
aagggcttca caccggagat cagcttcaac tatttgggcc aattcgacag tgaagtcaaa    21780
accgatttct ttgaaccgtc cgctttcgat atggggcgcc aagtaagcgg agaatcagag    21840
gcgctgtacg cattaagctt cagcggcatg atcagaaacg gccggtttgt gctttcctgc    21900
tcctacaatg agaaggagtt tgaaagagct acagtcgagg agcaaatgga acggtttaaa    21960
```

```
gaaaacctcc tgatgctaat ccgccattgc acggaaaaag aagacaagga attcacacca   22020
agcgacttca gcgccgaaga ccttgaaatg gacgagatgg gagatatctt tgacatgctt   22080
gaggagaatt taaaataaaa cgcaagggaa ttacagaagg cgggagcgaa acatatgagt   22140
caatttagca aggatcaggt tcaagatatg tattacctat cgccgatgca ggaagggatg   22200 cttttcatg ccatcctgaa tcccggccaa agcttttacc ttgaacaaat cacgatgaaa   22260
gtaaaaggca gcttgaatat caaatgtctt gaagaaagca tgaatgtgat catggaccgg   22320
tacgatgtat ttcgtaccgt gttcattcac gaaaaagtaa aaaggcctgt ccaagtcgta   22380
ttgaaaaaac ggcagttcca tatagaagaa atcgatctga cacacttaac gggcagcgag   22440
caaacagcca aaatcaatga gtacaaagaa caggataaga tcagggggttt tgatttgacg   22500 cgggatattc cgatgcgggc agccattttc aagaaagctg aagaaagctt gaatggggtg   22560
tggagctacc accacattat tttggacgga tggtgcttcg gcatcgtcgt acaggatcta   22620
tttaaggtat acaatgctct gcgcgaacaa aagccgtaca gcctgccgcc cgtcaaaccg   22680
tataaagact acatcaagtg gcttgaaaag caggataaac aagcatcact gcgttactgg   22740
cgcgaatatt tagagggctt tgaaggacaa acgacgtttg cggagcaaag aaagaaacaa   22800
aaggacggct atgagccgaa agagctgctc ttttcactgt cggaggcgga aacaaaggcc   22860
tttaccgagc ttgcaaaatc gcagcatacc actttgagta cggcgctgca ggcagtctgg   22920
agcgtattga tcagccgcta tcagcagtct ggcgatttgg ccttcggtac agttgtttca   22980
gggcgtcccg cggaaatcaa aggcgttgaa catatggtcg ggctgtttat caacgttgtc   23040
ccgagacgtg tgaagctgtc tgagggtatc acatttaacg gcttgctcaa gcggctgcag   23100
gagcaatcgc tgcagtccga gccgcatcaa tatgtgccgc tttatgacat ccaaagccag   23160
gccgatcagc cgaaactgat tgaccacatc attgttttg agaactatcc gcttcaggat   23220
gcgaaaaatg aagaaagcag tgaaaacggc tttgatatgg tggatgttca tgtttttgag   23280
aagtcgaatt atgatctcaa cctgatggct tccccgggag atgagatgct gattaagctt   23340
gcctataatg agaatgtgtt tgatgaggcg tttatcctgc gcttgaaatc tcagcttctt   23400
acagcaattc agcagctcat ccagaatcct gatcagcctg tcagcacgat caacctcgtt   23460
gacgacaggg agagagaatt tttgctaacc ggcttaaacc cgccggctca agctcatgaa   23520
acaaagcctc tgacgtattg gttcaaggaa gcagtgaacg ccaatccgga tgcaccggcg   23580
cttacgtatt ccggccagac cctgtcttat cgcgaattag atgaggaagc gaaccgcatt   23640
gcacgccggt gcaaaaaaca cggtgcgggc aaaggctctg ttgtagcgct gtacacgaag   23700
cgctcacttg aactggtgat cggcattctc ggtgtattaa aggcgggagc agcctatctg   23760
ccggttgatc cgaagctgcc agaggaccga atctcgtata tgctggctga cagtgcggca   23820
gcctgtcttc tgacgcatca ggagatgaaa gaacaagcgg ctgagctgcc gtatacaggc   23880
acaacgctct tcattgatga tcaaacacgg tttgaagaac aggcaagcga tcctgcaacc   23940
gcgattgatc ctaatgatcc ggcatatatc atgtacacgt ccggcacaac cggaaagcca   24000
aagggcaata tcaccactca tgccaatatt caaggattgg tcaagcatgt agactacatg   24060 gcatttctg atcaggatac gttccttgtct gtttcgaatt acgcctttga tgcatttacc   24120
tttgatttct atgcttctat gctgaatgcg gcacggctca ttatcgcaga tgaacatacg   24180
ctgcttgata cagaacggct cacagatctg atcctgcaag agaatgtcaa tgtcatgttt   24240
gcgacaaccg cactatttaa tcttctcaca gatgcgggag aggattggat gaagggctt   24300 cgctgtatat tattcggcgg agagcgcgcg tcagtgcctc atgtcagaaa agcgctgcgg   24360
```

```
atcatggggc cgggcaagct gattaactgc tacgggccga ctgagggaac agtgtttgcg   24420
acagctcacg tcgtgcatga tctgccggat tccatctcct cattgccgat cggaaagccg   24480
atcagcaatg ccagtgttta tattctgaat gagcaaagcc agctccagcc attcggggcg   24540
gtcggtgaac tgtgcatcag cggaatgggc gtgtcaaaag ggtatgtaaa tcgtgctgac   24600
ctcacgaagg aaaagtttat cgagaacccg ttcaagccgg agaaacgct  ttaccgtaca   24660 ggggatttag cgcgctggct gccggatgga acgattgaat acgccggccg tattgacgac   24720
caggtcaaaa tacgcggaca ccggattgag cttgaagaaa tcgaaaagca gctgcaggaa   24780
tacccaggtg tgaaagatgc ggtcgttgtg gcggaccgcc atgagtctgg cgatgcatca   24840
atcaatgcct accttgtgaa ccgaacgcag cttttcagctg aagacgtgaa ggcgcacctg   24900
aaaaaacagc ttcctgctta catggtgccg caaaccttta ccttcttgga tgagcttcct   24960
ttaacgacga acgggaaagt caataaacgg ctgctcccaa aacctgatca ggatcagctg   25020
gcggaagaat ggattggacc gcggaacgag atggaagaaa caatcgcaca aatatggtct   25080
gaggttctcg gcagaaagca aattggcatt catgacgatt tctttgcgct cggagggcat   25140
tccttgaagg ccatgaccgc cgcgtcccgc atcaagaaag agctcgggat tgatcttcca   25200
gtgaagcttt tgtttgaagc gccgacgatc gccggcattt cagcgtattt gaaaaacggg   25260
ggctctgatg gcttgcagga tgtaacgata atgaatcagg atcaggagca gatcattttc   25320
gcatttccgc cggttctggg ctatggcctt atgtaccaaa atctgtccag ccgcttgccg   25380
tcatacaagc tatgcgcctt tgattttatt gaggaggaag accggcttga ccgctatgcg   25440
gatttgatcc agaagctgca gccggaaggg cctttaacat tgtttggata ttcagcggga   25500
tgcagcctgg cgtttgaagc tgcgaaaaag cttgaggaac aaggccgtat tgttcagcgg   25560
atcatcatgg tggattccta taaaaaacaa ggtgtcagtg atctggacgg acgcacggtt   25620
gaaagtgatg tcgaagcgtt gatgaatgtc aatcgggaca atgaagcgct caacagcgaa   25680
gccgtcaaac acggcctcaa gcaaaaaaca catgcctttt actcatacta cgtcaacctg   25740
atcagcacag gccaggtgaa agcagatatt gatctgttga cttccggcgc tgattttgac   25800
atgccggaat ggcttgcatc atgggaagaa gctacaacag gtgtttaccg tgtgaaaaga   25860
ggcttcggaa cacacgcaga aatgctgcag ggcgaaacgc tagataggaa tgcggagatt   25920
ttgctcgaat ttcttaatac acaaaccgta acggtttcat aaatgaagtg atgaaaggag   25980
gagacagcca atgagccaac tcttcaaatc atttgatgcg tcggaaaaaa cacagctcat   26040 ctgtttttccg tttgccggcg ctattcggc  gtcgtttcgc cctctccatg ctttttttgca   26100 gggggagtgc gagatgctcg ctgccgagcc gccgggacac ggcacgaatc aaacgtcagc   26160
cattgaggat ctcgaagagc tgacggattt gtacaagcaa gaactgaacc ttcgccctga   26220
tcggccgttt gtgctgttcg gacacagtat gggcggaatg atcaccttca ggctggcgca   26280
aaagcttgag cgtgaaggca tctttccgca ggcggttatc atttctgcaa tccagccgcc   26340
tcatattcag cggaagaaag tgtcccacct gcctgatgat cagtttctcg atcatattat   26400
ccaattaggc ggaatgcccg cagagcttgt tgaaaataag gaggtcatgt cctttttcct   26460
gccttctttc cgatcagatt accgggctct tgaacaattt gagctttacg atctggccca   26520
gatccagtcg cctgttcatg tctttaacgg gcttgatgat aaaaaatgca tacgagatgc   26580
ggaagggtgg aagaagtggg caaaagacat cacattccat caatttgacg gcgggcacat   26640
gttcctgctg tcacaaacgg aagaagtcgc agaacggatt tttgcgatct tgaatcagca   26700
```

```
tccgatcatt caaccgtgat caaaagcgga cagcttcggc tgttccgctt tttttgtgtt  26760
gaatgccaat ttttgcatgg tataatagtc gaaatactca aataaaggca ggttgaaaca  26820
tgcgcacgtc tcccaggatg aaatggtttg tattgctgtt tacgtttgtt ttcgccatcg  26880
gaatgaactc attcagaaat tcctttcaat tttttatgct gccaatggca gatgccttcc  26940
atgccgacag gtcgctgatt tcggtttctg tcagcatttt tatgatcaca accggcatcg  27000
tccagttttt tgtcggtttt tttatcgacc gtttcagtgt cagaaaaatt atggcgcttg  27060
gagctgtctg catcagcgca agcttttggg tgcttcctta ttcaccgaat gttcatgtgt  27120
tttccgccat ttacggtgtg cttggcggaa tcggctattc ctgcgcgtc ggcgtgacga  27180 cccagtactt catcagccgt tggtttgaca cacataaagg tctggcgctt gctattttga  27240
ccaatgccaa ctctgcgggc ctgctgcttc tctcacccat ttgggctgcg gctccgtatc  27300
atgccggctg gcagagcacc tatacgattt tgggaatcgt catggcggct gttctgctgc  27360
cgctcctcgt ctttgggatg aagcacccgc cacatgcgca agcggaaact gtgaaaaaat  27420
cttatgattg gcgggggttt tggaacgtga tgaagcaatc ccgcctcatt catatcctgt  27480
acttcggcgt gtttacttgc ggatttacaa tgggaattat tgatgctcac ctcgtcccga  27540
tactgaagga tgcgcatgtc tctcatgtca acggaatgat ggccgcgttc ggggcgttta  27600
tcatcattgg cggattattg gcgggctggc tgtccgatct cctcgggagc agaagcgtca  27660
tgctatccat cttatttgtc attcggctgc tcagcctgat ttgcctgctc attcccattc  27720
tcggaattca tcacagcgaa ctttggtatt ttggctttat tctgttattc gggctcagtt  27780
acacaggcgt gatcccgctg accgcggcgt caatttcgga aagctatcaa acaggactga  27840
tcggatcgct gttaggcatc aatttcttta tccatcaggt tgccggagct cttagcgtgt  27900
atgcgggcgg tttgttttt gacatgactc atggttattt gctgatagtc gctgtgtgca  27960
tcgtgtttgt gggtttatcg gctgtaatag agctggtgcc gttttagat aaacagaagg  28020 caaaagaaac ccaccattca atataaaagg atcagcactg tcaatgctga tccttttaa  28080 atttgagttt ttttgtttcg gtatttttaa ggataatctc cttgaatctg ttcatctcct  28140
cttcggagtg aaaaaaatgt ttggggatcg caatatattg gctgctggat gtattgatcc  28200
gaaagatatt cttatattcg aaaacagctg tgatttcatt ccaattgaaa atgaggttat  28260
attttttaga acttatacag attccttctt gattgagggt atatgttctt ttagatttca  28320
tccgttcgtt cttcttgtat gctctggaaa acttcacata tagaagaagg aggagcagca  28380
gtgtaaacag aacggacatc acgataatca acatactgtt cataaacaag ttaagcgcgt  28440
cactgccata aacgatacgg ggccatccat taatgaagtt aactgcagca aatatggcgc  28500
aaaacaacag aaagtaaaag catgatattt ttgcgatttg ataaaaaag atttctctta  28560 catccttaaa agcgatttct cctggaagat tgatactttc attagcatat tgaatcatac  28620
ggtaaaccta cacctctaac catgttttc ctttcagtct agcataattt ctcattttt  28680 tgcaggcata ccagggcgct ttgttttttt ctccagattg atattgctcc ccaccacgcc  28740
aatcataata caaacagccc cggcaagatg ataccaggcc aggctttcgt tgagaatcat  28800
aactcctgca atcatcgtca caatggtaga tacatgatta aaagcactca ttttaaacgc  28860
ctcaattcgc gacagcgtat agttagacag aaatgaagtg acaagtgaag acagcacgcc  28920
caaatacaca atggcgagaa cgaagccggg ctccgggaac ggcagaaaat aagtgccgac  28980
tgttcccgcc gctccgtgac gcacaagggc gatggcgttg aagacgacaa agccgatggc  29040
tgacatgatg taggtgagct cggtcagctt gaaccgctgc gtcattttc tggcagcagt  29100
```

```
attgtacatc gctgaagaca aagcagacaa taggatcagc aaagacccit ttaagctggc  29160
tgattccacg tcaacgcctt tcatcacaaa aataaacatg acgccggcaa cggataaaac  29220
cgtgaacccc ttttgcgtcc acgttgggcg ttccttaaaa acataagcgg caaagaccat  29280
cgtgaaaatc ggaatggctg cttgaataat tcccgcttca gaggaggacg agtacacaag  29340
gccgaatgcc tgaaagctga aaataacgc gggatacagc agggcgagcg gcaaaatggc   29400
aatgacgtcc tttacgcgga ttgatagctt tacccagccg aataagatcg gtacagtggc  29460
cgcagcaaac gcaatggtga accgatgcgc caaaatatca aacggctctg ctgtttgcag   29520
tgcgattttt acgaatagaa aggataaacc gataatgaac gaatataaaa tagccgctat   29580
ataagcgggg gcttgctgat gtttaaccat aatgggaagg ctcctttac ctgaattgca   29640
gcgccggtcg ctcccttat tgtatggccg cggtcagaac ggtacaatga gaaaacaat    29700
gaactgtacc ggtacaaaac aggggagaa ggcatggaga aatatatgag tctattaatg   29760
aggatagagg agatgatgca aagcaccgcc tatcaagaag gagacaggct tccatctatc   29820
cgtcagctgt ccgccgcta ccaagtcagc aaaagcacag tgatccgcgc gctgcaggag   29880
ctggaaaagc gccaccttat ctattctgtt ccgaaaagcg gctattatat tgtgaaaaag  29940
acagggaaat caaaaagcgg gcagcttggc cccatcgact ttgccacatc tgcgccggat  30000
cccgatgtgt ttccgtatct tgattttcag cactgtatca acaaagcgat tgatacatac  30060
aaaaacgatt tgtttatta tgggacgcca aaggggcttc catcactcat ccgcgtactc   30120
cgaaagctct tggccactca acaggtattt gcggatgaac ggcatatttt cattacatca   30180
ggtgtccagc aggcgttatc cttgctttgt gccatgccgt tcccaaatgg gaaagagaag  30240
atcgccattg aacagccggg ctaccatttg atggtcgaac agcttgagac acttgggatt  30300
cccgccatcg gggtgaaacg aacggaagaa gggcttgata tagccgaggt tgagcggtta  30360
tttcaaacag aatcgattaa attttttat acgatgccgc gcttccataa cccgcttggc   30420
tgctcattgt cagagcgtga taaacaggag cttgtgagac tggcagaagc gtatgatgtc  30480
tatctcgttg aggatgatta cctcggtgat ctggaggaaa ataaaaaggc agatccgctg  30540
tacgcatatg atctgtcctc acatgtcatc tatttgaaaa gcttctcaaa aatgatgttc   30600
cccggccttc gcgtggggc ggctgttttg cccgaagcgc tgactgacac gttctatgcg   30660
tacaaaaagc tgaacgacat cgactgttcg atgatttctc aagcggcatt ggagatttac  30720
ctgaaaagcg gtatgtacgg caggcataag gagaaaatca gagattctta taaagagcgg  30780
tcgctgaggc tacatcaagc cattcgaact cacaggcagc tgggaagcgg acgctttacg  30840
ttctccagcg ggcaggcacc ctgtatgcac acccatctgg tgcttcctca ggatctgccc  30900
gcctcaagag tgattcatag actgaaaaaa caagggtga tccttgaggc gatagaccgt    30960
cattatttat cagattatca gaaagaaaat ctattaaaaa tcaatatttc caatgtgaaa  31020
acggaagata ttgagcgcgg tgtcaagctg ttgatgagcc atttataaaa gctcttcgta   31080
cgagaccatt gtgatatcct cggggaaatc agggtgtgcg gcgcatacag ccatttttgta 31140
gccgggatcg acctcatacg ttttgatata gcatggggaa tggctgtccg gaagctcaat  31200
ggatacttgt ccgtcctgat gcaggcgcac tgaaaaggaa tcaagcggaa gcgataagcc  31260
tttgccttcc tgtttgataa agctttcttt cattgaccat agatgataaa aatagtctgt  31320
ctgctcgtcc ttgtcttttg ctaaaaggtc gctgtactct gtttttgaaa agaagcgctt   31380
ggcgatctca agactgatcg gtttcgttttt ttcgatatct atgccgatcg gctgtgaatc  31440
```

-continued

```
aaacgcgcaa atgacccagc ggccggagtg agaaatattg aaatgagcgt cgggaagatc    31500
agggatgcac ggcttcccgt attcctgcgt gctaaagcgg atatcggatt tgtccaactg    31560
atactgcctg cttatgactg agcgaacgag cacatctccc agcagggtgc ggtgagcatc    31620
ttctttatga taaaatctcc ggcatttctc ccgtttttca ggtgatatga aagacatgaa    31680
ccgttcattt tcttcctgtg aaagcgggcg gtccatataa attccgtaaa tcttcattct    31740
agatcctccg tctgcaaaag attgtcaaaa ccatcctatc atacttccac aagactcata    31800
tagaggagaa aataaaaaaa caaagccaag gcggctttgt t                       31841
```

<210> SEQ ID NO 44
<211> LENGTH: 20
<212> TYPE: DNA
<213> ORGANISM: Artificial
<220> FEATURE:
<223> OTHER INFORMATION: primer

<400> SEQUENCE: 44

```
gcggcagaat gaaagtgtta                                                   20
```